(12) United States Patent
Miller et al.

(10) Patent No.: US 9,522,936 B2
(45) Date of Patent: Dec. 20, 2016

(54) ENGINEERED TRANSCRIPTION ACTIVATOR LIKE EFFECTOR (TALE) PROTEINS

(71) Applicant: Sangamo BioSciences, Inc., Richmond, CA (US)

(72) Inventors: Jeffrey C. Miller, Richmond, CA (US); Edward J. Rebar, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 14/695,644

(22) Filed: Apr. 24, 2015

(65) Prior Publication Data

US 2015/0307561 A1 Oct. 29, 2015

Related U.S. Application Data

(60) Provisional application No. 61/983,760, filed on Apr. 24, 2014.

(51) Int. Cl.
| | | |
|---|---|---|
| *C07K 14/195* | (2006.01) | |
| *C12N 15/90* | (2006.01) | |
| *C12N 9/22* | (2006.01) | |

(52) U.S. Cl.
CPC .............. *C07K 14/195* (2013.01); *C12N 9/22* (2013.01); *C12N 15/902* (2013.01); *C07K 2319/00* (2013.01); *C07K 2319/80* (2013.01)

(58) Field of Classification Search
CPC .......................... C07K 14/195; C12N 15/902
USPC ........................................ 435/463, 468, 471
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 6,453,242 B1 | 9/2002 | Eisenberg et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,067,317 B2 | 6/2006 | Rebar et al. | |
| 7,074,596 B2 | 7/2006 | Darzynkiewicz et al. | |
| 7,163,824 B2 | 1/2007 | Cox, III et al. | |
| 7,262,054 B2 | 8/2007 | Jamieson et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,153,773 B2 | 4/2012 | Jemiclity et al. | |
| 8,329,986 B2 | 12/2012 | Butler et al. | |
| 8,409,861 B2 | 4/2013 | Guschin et al. | |
| 8,420,782 B2 | 4/2013 | Bonas et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,470,973 B2 | 6/2013 | Bonas et al. | |
| 8,563,314 B2 | 10/2013 | Gregory et al. | |
| 8,586,363 B2 | 11/2013 | Voytas et al. | |
| 8,586,526 B2 | 11/2013 | Gregory et al. | |
| 8,623,618 B2 | 1/2014 | Doyon et al. | |
| 8,685,737 B2 | 4/2014 | Serber et al. | |
| 8,697,853 B2 | 4/2014 | Voytas et al. | |
| 8,772,008 B2 | 7/2014 | Doyon | |
| 2003/0232410 A1 | 12/2003 | Liljedahl et al. | |
| 2005/0026157 A1 | 2/2005 | Baltimore et al. | |
| 2005/0208489 A1 | 9/2005 | Carroll et al. | |
| 2006/0063231 A1 | 3/2006 | Li et al. | |
| 2008/0159996 A1 | 7/2008 | Ando et al. | |
| 2009/0068164 A1 | 3/2009 | Segal et al. | |
| 2009/0117617 A1 | 5/2009 | Holmes et al. | |
| 2010/0041028 A1 | 2/2010 | Barbas | |
| 2010/0047805 A1 | 2/2010 | Wang | |
| 2010/0218264 A1 | 8/2010 | Cui et al. | |
| 2010/0291048 A1 | 11/2010 | Holmes et al. | |
| 2011/0201055 A1 | 8/2011 | Doyon et al. | |
| 2011/0201118 A1 | 8/2011 | Yang et al. | |
| 2011/0207221 A1 | 8/2011 | Cost et al. | |
| 2011/0265198 A1 | 10/2011 | Gregory et al. | |
| 2011/0287545 A1 | 11/2011 | Cost et al. | |
| 2012/0017290 A1 | 1/2012 | Cui et al. | |
| 2012/0195936 A1 | 8/2012 | Rudolph et al. | |

(Continued)

FOREIGN PATENT DOCUMENTS

| | | |
|---|---|---|
| EP | 0242246 B1 | 11/1992 |
| EP | 2206723 A1 | 7/2010 |

(Continued)

OTHER PUBLICATIONS

Beurdeley, et al., "Compact Designer Talens for Efficient Genome Engineering," *Nature Communications* 4:1762 (2013) doi:10.10.38/ncomms2782.

Boch, et al., "Breaking the Code of DNA Binding Specificity of TAL-Type III Effectors," *Science* 326:1509-1512 (2009).

Bogdanove and Voytas, "TAL Effectors: Customizable Proteins for DNA Targeting," *Science* 333:1843-1846 (2011).

Boissel, et al., "Megatals: A Rare-Cleaving Nuclease Architecture for Therapeutic Genome Engineering," *Nucl. Acid Res.* 1-13 (2013) doi: 10.1093/nar/gkt1224.

Cermak, et al., "Efficient Design and Assembly of Custom Talen and Other TAL Effector-Based Constructs for DNA Targeting," *Nucleic Acids Research* 39:e82 (2011).

Christian, et al., "Targeting DNA Double-Strand Breaks With TAL Effector Nucleases," *Genetics* 186:757-776 (2010).

Cong, et al., "Comprehensive Interrogation of Natural Tale DNA-Binding Modules and Transcriptional Repressor Domains," *Nat. Commun.* 3:968 (2012).

(Continued)

*Primary Examiner* — Janet Epps-Smith
(74) *Attorney, Agent, or Firm* — Pasternak Patent Law; Susan Abrahamson

(57) ABSTRACT

Disclosed herein are methods and compositions for design and use of engineered TALEs.

21 Claims, 21 Drawing Sheets

(56) References Cited

U.S. PATENT DOCUMENTS

| | | |
|---|---|---|
| 2013/0122591 A1 | 5/2013 | Cost et al. |
| 2013/0137104 A1 | 5/2013 | Cost et al. |
| 2013/0171124 A1 | 7/2013 | Cong et al. |
| 2013/0177960 A1 | 7/2013 | Rebar |
| 2013/0177983 A1 | 7/2013 | Rebar |
| 2013/0196373 A1* | 8/2013 | Gregory ............... C07K 14/195 435/69.1 |
| 2013/0274129 A1 | 10/2013 | Katzen et al. |
| 2015/0056705 A1 | 2/2015 | Conway et al. |

FOREIGN PATENT DOCUMENTS

| | | |
|---|---|---|
| EP | 2392208 A1 | 12/2011 |
| GB | 2338237 A | 12/1999 |
| WO | WO 94/18313 A1 | 8/1994 |
| WO | WO 95/09233 A1 | 4/1995 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 2009/054985 A1 | 4/2001 |
| WO | WO 01/60970 A2 | 8/2001 |
| WO | WO 01/83732 A2 | 11/2001 |
| WO | WO 01/83793 A2 | 11/2001 |
| WO | WO 01/88197 A2 | 11/2001 |
| WO | WO 02/099084 A2 | 12/2002 |
| WO | WO 2007/014275 A2 | 1/2007 |
| WO | WO 2007/060495 A1 | 5/2007 |
| WO | WO 2007/139982 A2 | 12/2007 |
| WO | WO 2009/095793 A1 | 8/2009 |
| WO | WO 2010/054348 A2 | 5/2010 |
| WO | WO 2010/079430 A1 | 7/2010 |
| WO | WO 2010/143917 A2 | 12/2010 |
| WO | WO 2011/017293 A2 | 2/2011 |
| WO | WO 2011/019385 A1 | 2/2011 |
| WO | WO 2011/072246 A2 | 6/2011 |
| WO | WO 2011/100058 A1 | 8/2011 |
| WO | WO 2011/146121 A1 | 11/2011 |
| WO | WO 2011/154393 A1 | 12/2011 |
| WO | WO 2011/159369 A1 | 12/2011 |

OTHER PUBLICATIONS

Deng, et al., "Structural Basis for Sequence-Specific Recognition of DNA by TAL Effectors," Science 335:720-723 (2012) doi: 10.1126/science.1215670.

Guilinger et al., "Broad Specificity Profiling of Talens Results Methods in Engineered Nucleases With Improved DNA-Cleavage Specificity," Nat Methods 11(4):429-435 (2014).

Hockmeyer, et al., "Genetic Engineering of Human ES and IPS Cells Using Tale Nucleases," Nat. Biotechnol. 29:731-734 (2011).

Juillerat, et al., "Comprehensive Analysis of the Specificity of Transcription Activator-Like Effector Nucleases," Nucleic Acids Research 1-13 (2014).

Kim, et al., "A Library of TAL Effector Nucleases Spanning the Human Genome," Nat. Biotechnol. 31:251-258 (2013).

Kormann, et al., "Expression of Therapeutic Proteins After Delivery of Chemically Modified MRNA in Mice," Nature Biotechnology 29(2):154-157 (2011).

Li, et al., "TAL Nucleases (TALNS): Hybrid Proteins Composed of TAL Effectors and Foki DNA-Cleavage Domain," Nucleic Acids Research 39:359-372 (2011).

Li, et al., "Modularly Assembled Designer TAL Effector Nucleases for Targeted Gene Knockout and Gene Replacement in Eukaryotes," Nucleic Acids Research 39:6315-6325 (2011).

Mak, et al., "The Crystal Structure of TAL Effector PTHXO1 Bound to Its DNA Target," Science 335:716-719 (2012).

Mali, et al., "CAS9 Transcriptional Activators for Target Specificity Screening and Paired Nickases for Cooperative Genome Engineering," Nat. Biotechnol. 31(9):833-838 (2013).

Miller, et al., "A Tale Nuclease Architecture for Efficient Genome Editing," Nat. Biotechnol. 29:143-148 (2011).

Miller, et al., "Improved Specificity of Tale-Based Genome Editing Using an Expanded RVD Repertoire," Nature Methods 12:465-471(2015) doi:10.1038/nmeth.3330.

Morbitzer, et al., "Assembly of Custom Tale-Type DNA Binding Domains by Modular Cloning," Nucleic Acids Research 39:5790-5799 (2011).

Moscou, et al., "A Simple Cipher Governs DNA Recognition by TAL Effectors," Science 326:1501 (2009).

Osborn, et al., "Talen-Based Gene Correction for Epidermolysis Bullosa," Molecular Therapy.doi: 10.1038/mt.2013.56.

Reyon, et al., "Flash Assembly of Talens for High-Throughout Genome Editing," Nat. Biotechnol. 30:460-465.

Sander, et al., "Targeted Gene Disruption in Somatic Zebrafish Cells Using Engineered Talens," Nat. Biotechnol. 29:697-698 (2011).

Sanjana, et al., "A Transcription Activator-Like Effector Toolbox for Genome Engineering," Nat. Protocols 7:171-192 (2012).

Schmid-Burgk, et al., "A Ligation-Independent Cloning Technique for High-Throughput Assembly of Transcription Activator-Like Effector Genes," Nat. Biotechnol 31:76-81 (2013).

Schomacic, et al., "Gene-For-Gene-Mediated Recognition of Nuclear-Targeted AVRBS3-Like Bacterial Effector Proteins," J Plant Physiol. 163(3):256-272 (2006).

Stella, et al., "Structure of the AVRBS3-DNA Complex Provides New Insights Into the Initial Thymine-Recognition Mechanism," Acta. Crystallogr D. Biol. Crystallogr 69:1707-1716 (2013).

Streubel, et al., "TAL Effector RVD Specificities and Efficiencies," Nat. Biotechnol. 30:593-595 (2012).

Tebas, et al., "Gene Editing of CCR5 in Autologous CD4 T Cells of Persons Infected With HIV," New Eng. J Med. 370(10):901 (2014).

Tesson, et al., "Knockout Rats Generated by Embryo Microinjection of Talens," Nat. Biotechnol. 29(8):695-696 (2011) doi: 10.103.8/nbt.1940.

Zhang, et al., "Efficient Construction of Sequence-Specific TAL Effectors for Modulating Mammalian Transcription," Nat. Biotechnol. 29(2):149-153 (2011) doi: 10.1038/nbt.1775.

* cited by examiner

Fig 1A
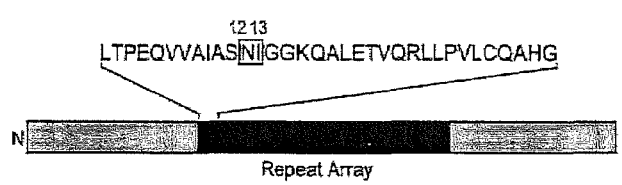
Fig 1B
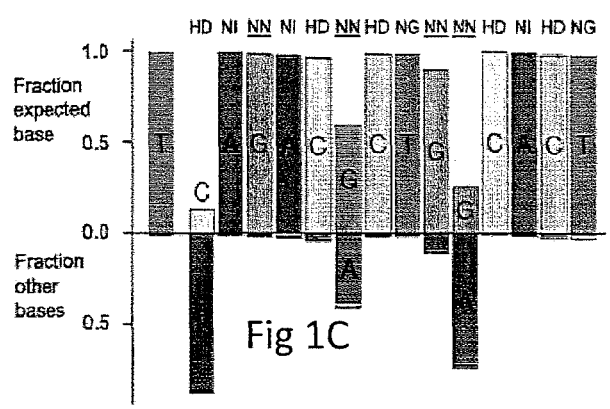
Fig 1C
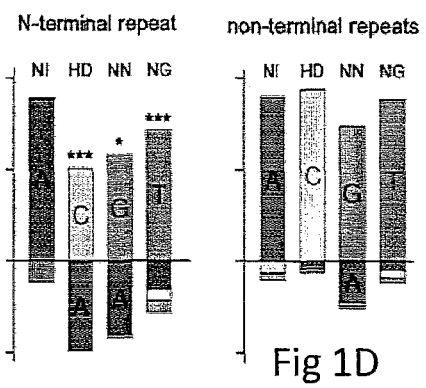
Fig 1D
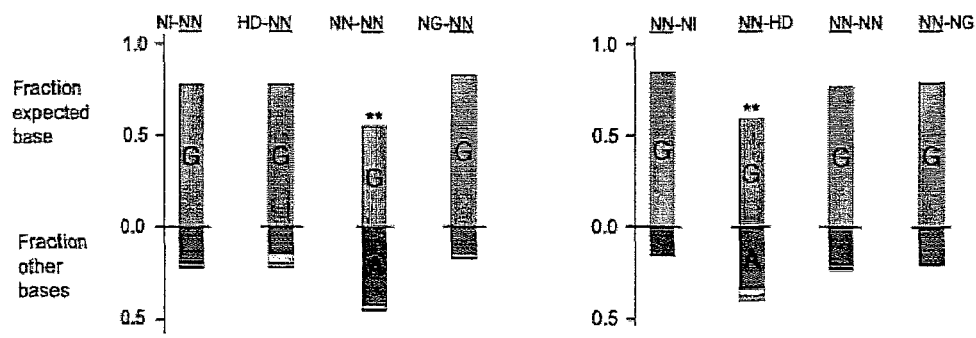
Fig 1E

Fig 2A

All 400 possible RVD sequences
↓
NG NN NI HD XX NI NG HD HD NG

| RVD | Base | | | |
|---|---|---|---|---|
| | | C | G | T |
| NI | 0.73 | 0.06 | 0.02 | 0.02 |
| HD | 0.28 | 0.96 | 0.01 | 0.12 |
| NN | 0.98 | 0.01 | 1.26 | 0.01 |
| NG | 0.59 | 0.15 | 0.15 | 0.97 |

Fig 2C

Plot

Fig 2D

| RVD | A | C | G | T |
|---|---|---|---|---|
| AA | 0.49 | 0.50 | 0.19 | 1.52 |
| CA | 0.55 | 0.55 | 0.07 | 1.05 |
| DA | 0.31 | 0.34 | 0.06 | 0.27 |
| EA | 0.72 | 0.40 | 0.07 | 0.57 |
| FA | 0.53 | 0.28 | 0.04 | 0.94 |
| GA | 0.14 | 0.12 | 0.03 | 0.36 |
| HA | 1.02 | 0.87 | 0.62 | 1.53 |
| IA | 0.30 | 0.33 | 0.02 | 0.53 |
| KA | 0.66 | 0.78 | 0.20 | 1.05 |
| LA | 0.26 | 0.16 | 0.02 | 0.57 |
| MA | 0.13 | 0.12 | 0.01 | 0.55 |
| NA | 0.90 | 0.86 | 0.46 | 1.28 |
| PA | 0.01 | 0.00 | 0.00 | 0.04 |
| QA | 0.37 | 0.34 | 0.08 | 1.22 |
| RA | 0.95 | 1.01 | 0.67 | 1.27 |
| SA | 0.66 | 0.48 | 0.19 | 0.58 |
| TA | 0.34 | 0.29 | 0.05 | 0.79 |
| VA | 0.37 | 0.42 | 0.02 | 1.72 |
| WA | 0.31 | 0.20 | 0.06 | 0.56 |
| YA | 0.37 | 0.30 | 0.06 | 1.09 |
| AC | 0.64 | 0.43 | 0.24 | 0.11 |
| CC | 0.36 | 0.41 | 0.19 | 0.30 |
| DC | 0.19 | 0.13 | 0.02 | 0.01 |
| EC | 0.37 | 0.41 | 0.10 | 0.08 |
| FC | 0.41 | 0.20 | 0.12 | 0.09 |
| GC | 0.24 | 0.09 | 0.02 | 0.05 |
| HC | 0.80 | 0.77 | 0.71 | 0.44 |
| IC | 0.10 | 0.21 | 0.04 | 0.14 |
| KC | 0.71 | 0.53 | 0.56 | 0.12 |
| LC | 0.13 | 0.06 | 0.01 | 0.04 |
| MC | 0.10 | 0.06 | 0.00 | 0.02 |
| NC | 0.66 | 0.52 | 0.43 | 0.17 |
| PC | 0.02 | 0.01 | 0.00 | 0.00 |
| QC | 0.12 | 0.15 | 0.06 | 0.03 |
| RC | 0.00 | 0.00 | 0.00 | 0.00 |
| SC | 0.54 | 0.50 | 0.12 | 0.23 |
| TC | 0.17 | 0.20 | 0.05 | 0.12 |
| VC | 0.23 | 0.34 | 0.05 | 0.30 |
| WC | 0.16 | 0.11 | 0.01 | 0.04 |
| YC | 0.36 | 0.28 | 0.06 | 0.07 |
| AD | 0.08 | 0.47 | 0.00 | 0.02 |
| CD | 0.01 | 0.23 | 0.00 | 0.00 |
| DD | 0.00 | 0.13 | 0.00 | 0.00 |
| ED | 0.02 | 0.32 | 0.00 | 0.02 |
| FD | 0.00 | 0.16 | 0.00 | 0.01 |
| GD | 0.00 | 0.05 | 0.00 | 0.01 |
| HD | 0.29 | 0.98 | 0.01 | 0.12 |
| ID | 0.01 | 0.19 | 0.01 | 0.02 |
| KD | 0.11 | 0.73 | 0.00 | 0.07 |
| LD | 0.00 | 0.03 | 0.00 | 0.00 |
| MD | 0.01 | 0.07 | 0.00 | 0.00 |
| ND | 0.09 | 0.77 | 0.00 | 0.03 |
| PD | 0.00 | 0.01 | 0.00 | 0.01 |
| QD | 0.00 | 0.19 | 0.00 | 0.02 |
| RD | 0.27 | 0.89 | 0.00 | 0.04 |
| SD | 0.09 | 0.46 | 0.00 | 0.03 |
| TD | 0.03 | 0.11 | 0.03 | 0.02 |
| VD | 0.00 | 0.13 | 0.00 | 0.03 |
| WD | 0.00 | 0.13 | 0.00 | 0.01 |
| YD | 0.01 | 0.20 | 0.00 | 0.01 |
| AE | 0.02 | 0.02 | 0.00 | 0.01 |
| CE | 0.01 | 0.03 | 0.00 | 0.03 |
| DE | 0.00 | 0.01 | 0.00 | 0.01 |
| EE | 0.00 | 0.01 | 0.00 | 0.01 |
| FE | 0.00 | 0.00 | 0.00 | 0.02 |
| GE | 0.01 | 0.01 | 0.01 | 0.02 |
| HE | 0.15 | 0.18 | 0.01 | 0.12 |
| IE | 0.01 | 0.00 | 0.01 | 0.02 |
| KE | 0.06 | 0.07 | 0.00 | 0.10 |
| LE | 0.01 | 0.00 | 0.01 | 0.02 |
| ME | 0.01 | 0.15 | 0.00 | 0.01 |
| NE | 0.07 | 0.04 | 0.00 | 0.02 |
| PE | 0.00 | 0.01 | 0.00 | 0.00 |
| QE | 0.01 | 0.01 | 0.00 | 0.00 |
| RE | 0.09 | 0.08 | 0.00 | 0.08 |
| SE | 0.03 | 0.04 | 0.00 | 0.02 |
| TE | 0.00 | 0.01 | 0.00 | 0.02 |
| VE | 0.01 | 0.01 | 0.00 | 0.01 |
| WE | 0.01 | 0.00 | 0.00 | 0.00 |
| YE | 0.00 | 0.01 | 0.01 | 0.01 |
| AF | 0.03 | 0.00 | 0.00 | 0.00 |
| CF | 0.08 | 0.00 | 0.05 | 0.01 |
| DF | 0.00 | 0.00 | 0.01 | 0.01 |
| EF | 0.01 | 0.00 | 0.00 | 0.00 |
| FF | 0.00 | 0.00 | 0.00 | 0.01 |
| GF | 0.02 | 0.00 | 0.00 | 0.01 |
| HF | 0.11 | 0.00 | 0.00 | 0.01 |
| IF | 0.00 | 0.01 | 0.00 | 0.00 |
| KF | 0.03 | 0.01 | 0.00 | 0.01 |
| LF | 0.00 | 0.00 | 0.00 | 0.00 |
| MF | 0.00 | 0.01 | 0.01 | 0.01 |
| NF | 0.10 | 0.01 | 0.01 | 0.01 |
| PF | 0.00 | 0.00 | 0.00 | 0.00 |
| QF | 0.02 | 0.00 | 0.03 | 0.00 |
| RF | 0.13 | 0.00 | 0.00 | 0.00 |
| SF | 0.04 | 0.01 | 0.00 | 0.02 |
| TF | 0.03 | 0.00 | 0.00 | 0.03 |
| VF | 0.00 | 0.00 | 0.01 | 0.00 |
| WF | 0.00 | 0.00 | 0.00 | 0.00 |
| YF | 0.00 | 0.00 | 0.00 | 0.00 |
| AG | 0.60 | 0.28 | 0.16 | 0.57 |
| CG | 0.35 | 0.10 | 0.12 | 0.67 |
| DG | 0.03 | 0.01 | 0.00 | 0.09 |
| EG | 0.07 | 0.02 | 0.01 | 0.51 |
| FG | 0.07 | 0.00 | 0.01 | 0.33 |
| GG | 0.59 | 0.46 | 0.30 | 1.03 |
| HG | 0.55 | 0.27 | 0.34 | 2.08 |
| IG | 0.07 | 0.02 | 0.00 | 0.70 |
| KG | 0.67 | 0.34 | 0.37 | 1.04 |
| LG | 0.06 | 0.02 | 0.00 | 0.32 |
| MG | 0.12 | 0.06 | 0.02 | 0.72 |
| NG | 0.60 | 0.15 | 0.15 | 0.99 |
| PG | 0.01 | 0.00 | 0.06 | 0.04 |
| QG | 0.35 | 0.11 | 0.06 | 0.98 |
| RG | 0.63 | 0.37 | 0.35 | 1.10 |
| SG | 0.71 | 0.54 | 0.26 | 0.89 |
| TG | 0.24 | 0.07 | 0.08 | 0.34 |
| VG | 0.08 | 0.02 | 0.00 | 0.67 |
| WG | 0.03 | 0.00 | 0.00 | 0.35 |
| YG | 0.09 | 0.01 | 0.00 | 0.74 |

FIGURE 2E

| RVD | A | C | G | T |
|---|---|---|---|---|
| AH | 0.05 | 0.02 | 0.24 | 0.04 |
| CH | 0.02 | 0.01 | 0.05 | 0.06 |
| DH | 0.00 | 0.01 | 0.38 | 0.01 |
| EH | 0.01 | 0.01 | 0.18 | 0.02 |
| FH | 0.01 | 0.00 | 0.02 | 0.01 |
| GH | 0.00 | 0.00 | 0.06 | 0.01 |
| HH | 0.33 | 0.09 | 0.89 | 0.21 |
| IH | 0.01 | 0.00 | 0.01 | 0.02 |
| KH | 0.07 | 0.01 | 0.12 | 0.09 |
| LH | 0.00 | 0.01 | 0.00 | 0.00 |
| MH | 0.01 | 0.00 | 0.00 | 0.00 |
| NH | 0.30 | 0.12 | 0.59 | 0.18 |
| PH | 0.01 | 0.00 | 0.00 | 0.00 |
| QH | 0.01 | 0.01 | 0.06 | 0.05 |
| RH | 0.05 | 0.01 | 0.71 | 0.03 |
| SH | 0.00 | 0.00 | 0.01 | 0.00 |
| TH | 0.02 | 0.01 | 0.13 | 0.06 |
| VH | 0.01 | 0.01 | 0.02 | 0.14 |
| WH | 0.00 | 0.00 | 0.01 | 0.00 |
| YH | 0.01 | 0.01 | 0.01 | 0.02 |
| AI | 0.35 | 0.04 | 0.01 | 0.07 |
| CI | 0.97 | 0.14 | 0.02 | 0.10 |
| DI | 0.41 | 0.01 | 0.01 | 0.01 |
| EI | 0.38 | 0.03 | 0.00 | 0.01 |
| FI | 0.33 | 0.02 | 0.00 | 0.00 |
| GI | 0.18 | 0.01 | 0.01 | 0.00 |
| HI | 0.72 | 0.18 | 0.09 | 0.02 |
| II | 0.10 | 0.02 | 0.00 | 0.01 |
| KI | 0.54 | 0.16 | 0.04 | 0.07 |
| LI | 0.07 | 0.01 | 0.00 | 0.00 |
| MI | 0.18 | 0.01 | 0.00 | 0.00 |
| NI | 0.74 | 0.06 | 0.02 | 0.02 |
| PI | 0.01 | 0.00 | 0.00 | 0.00 |
| QI | 0.37 | 0.04 | 0.01 | 0.02 |
| RI | 0.84 | 0.10 | 0.05 | 0.02 |
| SI | 0.46 | 0.07 | 0.01 | 0.06 |
| TI | 0.37 | 0.07 | 0.00 | 0.07 |
| VI | 0.29 | 0.03 | 0.00 | 0.03 |
| WI | 0.15 | 0.01 | 0.01 | 0.01 |
| YI | 0.46 | 0.02 | 0.00 | 0.01 |

| RVD | A | C | G | T |
|---|---|---|---|---|
| AK | 0.03 | 0.00 | 0.31 | 0.00 |
| CK | 0.01 | 0.00 | 0.36 | 0.03 |
| DK | 0.00 | 0.00 | 0.17 | 0.00 |
| EK | 0.00 | 0.00 | 0.27 | 0.00 |
| FK | 0.00 | 0.01 | 0.05 | 0.01 |
| GK | 0.02 | 0.01 | 0.08 | 0.08 |
| HK | 0.01 | 0.00 | 0.23 | 0.00 |
| IK | 0.01 | 0.00 | 0.19 | 0.04 |
| KK | 0.01 | 0.00 | 0.37 | 0.01 |
| LK | 0.00 | 0.01 | 0.02 | 0.01 |
| MK | 0.00 | 0.00 | 0.05 | 0.00 |
| NK | 0.01 | 0.00 | 0.43 | 0.00 |
| PK | 0.00 | 0.00 | 0.00 | 0.00 |
| QK | 0.00 | 0.00 | 0.31 | 0.02 |
| RK | 0.02 | 0.00 | 0.30 | 0.01 |
| SK | 0.03 | 0.02 | 0.16 | 0.04 |
| TK | 0.00 | 0.00 | 0.13 | 0.01 |
| VK | 0.00 | 0.00 | 0.07 | 0.01 |
| WK | 0.00 | 0.00 | 0.02 | 0.00 |
| YK | 0.00 | 0.00 | 0.15 | 0.01 |
| AL | 0.03 | 0.00 | 0.00 | 0.01 |
| CL | 0.04 | 0.00 | 0.01 | 0.01 |
| DL | 0.01 | 0.01 | 0.00 | 0.01 |
| EL | 0.02 | 0.01 | 0.00 | 0.01 |
| FL | 0.01 | 0.00 | 0.00 | 0.00 |
| GL | 0.01 | 0.00 | 0.00 | 0.02 |
| HL | 0.31 | 0.00 | 0.00 | 0.01 |
| IL | 0.01 | 0.00 | 0.00 | 0.01 |
| KL | 0.23 | 0.00 | 0.00 | 0.01 |
| LL | 0.00 | 0.00 | 0.00 | 0.01 |
| ML | 0.01 | 0.00 | 0.00 | 0.03 |
| NL | 0.12 | 0.01 | 0.00 | 0.06 |
| PL | 0.00 | 0.00 | 0.00 | 0.00 |
| QL | 0.04 | 0.00 | 0.00 | 0.01 |
| RL | 0.26 | 0.00 | 0.00 | 0.01 |
| SL | 0.03 | 0.01 | 0.03 | 0.06 |
| TL | 0.03 | 0.00 | 0.00 | 0.02 |
| VL | 0.03 | 0.00 | 0.00 | 0.01 |
| WL | 0.01 | 0.01 | 0.00 | 0.01 |
| YL | 0.01 | 0.00 | 0.00 | 0.00 |

| RVD | A | C | G | T |
|---|---|---|---|---|
| AM | 0.05 | 0.03 | 0.00 | 0.00 |
| CM | 0.13 | 0.09 | 0.00 | 0.02 |
| DM | 0.03 | 0.01 | 0.00 | 0.01 |
| EM | 0.02 | 0.04 | 0.00 | 0.00 |
| FM | 0.01 | 0.02 | 0.01 | 0.01 |
| GM | 0.01 | 0.01 | 0.00 | 0.01 |
| HM | 0.38 | 0.26 | 0.00 | 0.02 |
| IM | 0.03 | 0.02 | 0.00 | 0.00 |
| KM | 0.22 | 0.13 | 0.00 | 0.01 |
| LM | 0.01 | 0.01 | 0.00 | 0.00 |
| MM | 0.01 | 0.01 | 0.00 | 0.02 |
| NM | 0.43 | 0.22 | 0.01 | 0.03 |
| PM | 0.01 | 0.00 | 0.01 | 0.01 |
| QM | 0.13 | 0.07 | 0.01 | 0.04 |
| RM | 0.38 | 0.19 | 0.05 | 0.02 |
| SM | 0.07 | 0.07 | 0.00 | 0.05 |
| TM | 0.02 | 0.01 | 0.00 | 0.00 |
| VM | 0.07 | 0.04 | 0.00 | 0.02 |
| WM | 0.01 | 0.01 | 0.00 | 0.01 |
| YM | 0.04 | 0.03 | 0.00 | 0.01 |
| AN | 0.82 | 0.00 | 0.88 | 0.00 |
| CN | 0.52 | 0.01 | 0.74 | 0.02 |
| DN | 0.36 | 0.00 | 1.30 | 0.00 |
| EN | 0.44 | 0.00 | 1.37 | 0.01 |
| FN | 0.60 | 0.00 | 0.74 | 0.02 |
| GN | 0.23 | 0.00 | 0.86 | 0.01 |
| HN | 1.05 | 0.01 | 1.11 | 0.02 |
| IN | 0.22 | 0.00 | 0.54 | 0.05 |
| KN | 0.96 | 0.02 | 1.02 | 0.05 |
| LN | 0.12 | 0.00 | 0.55 | 0.00 |
| MN | 0.13 | 0.00 | 0.27 | 0.02 |
| NN | 1.00 | 0.01 | 1.29 | 0.01 |
| PN | 0.00 | 0.00 | 0.02 | 0.00 |
| QN | 0.20 | 0.00 | 0.66 | 0.00 |
| RN | 0.89 | 0.00 | 1.10 | 0.01 |
| SN | 0.44 | 0.01 | 0.99 | 0.01 |
| TN | 0.34 | 0.00 | 0.57 | 0.01 |
| VN | 0.22 | 0.00 | 0.58 | 0.03 |
| WN | 0.41 | 0.00 | 0.73 | 0.02 |
| YN | 0.61 | 0.00 | 0.84 | 0.00 |

FIGURE 2F

| RVD | A | C | G | T |
|---|---|---|---|---|
| AP | 0.35 | 0.33 | 0.09 | 0.55 |
| CP | 0.20 | 0.36 | 0.08 | 1.17 |
| DP | 0.08 | 0.09 | 0.00 | 0.26 |
| EP | 0.07 | 0.13 | 0.01 | 0.58 |
| FP | 0.10 | 0.15 | 0.01 | 0.19 |
| GP | 0.10 | 0.12 | 0.00 | 0.28 |
| HP | 0.58 | 0.82 | 0.20 | 0.84 |
| IP | 0.12 | 0.19 | 0.01 | 0.57 |
| KP | 0.63 | 0.67 | 0.17 | 0.98 |
| LP | 0.09 | 0.14 | 0.02 | 0.38 |
| MP | 0.06 | 0.07 | 0.01 | 0.46 |
| NP | 0.48 | 0.45 | 0.12 | 0.61 |
| PP | 0.01 | 0.01 | 0.00 | 0.07 |
| QP | 0.12 | 0.18 | 0.01 | 0.60 |
| RP | 0.83 | 0.58 | 0.56 | 0.97 |
| SP | 0.32 | 0.27 | 0.02 | 0.56 |
| TP | 0.11 | 0.15 | 0.02 | 0.58 |
| VP | 0.09 | 0.16 | 0.01 | 0.61 |
| WP | 0.05 | 0.08 | 0.00 | 0.29 |
| YP | 0.12 | 0.27 | 0.01 | 0.83 |
| AQ | 0.08 | 0.04 | 0.15 | 0.05 |
| CQ | 0.04 | 0.03 | 0.39 | 0.05 |
| DQ | 0.01 | 0.03 | 0.03 | 0.02 |
| EQ | 0.01 | 0.06 | 0.07 | 0.01 |
| FQ | 0.01 | 0.00 | 0.08 | 0.01 |
| GQ | 0.03 | 0.02 | 0.04 | 0.02 |
| HQ | 1.00 | 0.49 | 1.09 | 0.39 |
| IQ | 0.02 | 0.03 | 0.11 | 0.12 |
| KQ | 0.19 | 0.13 | 0.52 | 0.14 |
| LQ | 0.00 | 0.00 | 0.01 | 0.01 |
| MQ | 0.01 | 0.00 | 0.02 | 0.00 |
| NQ | 0.12 | 0.10 | 0.35 | 0.02 |
| PQ | 0.00 | 0.00 | 0.00 | 0.00 |
| QQ | 0.02 | 0.02 | 0.08 | 0.02 |
| RQ | 0.28 | 0.11 | 0.69 | 0.17 |
| SQ | 0.03 | 0.04 | 0.09 | 0.05 |
| TQ | 0.02 | 0.01 | 0.09 | 0.08 |
| VQ | 0.02 | 0.02 | 0.09 | 0.12 |
| WQ | 0.01 | 0.01 | 0.04 | 0.00 |
| YQ | 0.01 | 0.02 | 0.06 | 0.02 |

| RVD | A | C | G | T |
|---|---|---|---|---|
| AR | 0.03 | 0.00 | 0.04 | 0.02 |
| CR | 0.00 | 0.00 | 0.05 | 0.02 |
| DR | 0.03 | 0.00 | 0.01 | 0.01 |
| ER | 0.03 | 0.01 | 0.03 | 0.03 |
| FR | 0.05 | 0.00 | 0.03 | 0.02 |
| GR | 0.02 | 0.01 | 0.01 | 0.07 |
| HR | 0.04 | 0.00 | 0.14 | 0.02 |
| IR | 0.00 | 0.00 | 0.00 | 0.04 |
| KR | 0.02 | 0.00 | 0.07 | 0.01 |
| LR | 0.00 | 0.00 | 0.00 | 0.00 |
| MR | 0.00 | 0.00 | 0.00 | 0.01 |
| NR | 0.02 | 0.00 | 0.08 | 0.01 |
| PR | 0.00 | 0.00 | 0.00 | 0.00 |
| QR | 0.01 | 0.00 | 0.01 | 0.02 |
| RR | 0.04 | 0.00 | 0.22 | 0.04 |
| SR | 0.05 | 0.01 | 0.04 | 0.04 |
| TR | 0.02 | 0.00 | 0.03 | 0.06 |
| VR | 0.04 | 0.02 | 0.03 | 0.07 |
| WR | 0.00 | 0.00 | 0.01 | 0.00 |
| YR | 0.01 | 0.00 | 0.01 | 0.02 |
| AS | 0.87 | 0.49 | 0.77 | 0.44 |
| CS | 0.44 | 0.38 | 0.43 | 0.85 |
| DS | 0.43 | 0.17 | 0.26 | 0.09 |
| ES | 0.43 | 0.46 | 0.17 | 0.32 |
| FS | 0.33 | 0.16 | 0.13 | 0.20 |
| GS | 0.51 | 0.11 | 0.23 | 0.12 |
| HS | 1.06 | 0.95 | 1.14 | 1.06 |
| IS | 0.22 | 0.27 | 0.10 | 0.94 |
| KS | 0.83 | 0.73 | 0.72 | 1.04 |
| LS | 0.28 | 0.12 | 0.11 | 0.21 |
| MS | 0.21 | 0.15 | 0.10 | 0.20 |
| NS | 1.76 | 0.61 | 1.14 | 0.77 |
| PS | 0.04 | 0.00 | 0.00 | 0.01 |
| QS | 0.40 | 0.30 | 0.13 | 0.19 |
| RS | 0.78 | 0.77 | 0.76 | 0.72 |
| SS | 0.62 | 0.38 | 0.66 | 0.56 |
| TS | 0.34 | 0.22 | 0.10 | 0.41 |
| VS | 0.41 | 0.28 | 0.15 | 0.45 |
| WS | 0.20 | 0.09 | 0.05 | 0.15 |
| YS | 0.40 | 0.21 | 0.11 | 0.37 |

| RVD | A | C | G | T |
|---|---|---|---|---|
| AT | 1.13 | 0.66 | 0.49 | 0.70 |
| CT | 0.73 | 0.64 | 0.59 | 1.27 |
| DT | 0.96 | 0.14 | 0.30 | 0.00 |
| ET | 1.05 | 0.49 | 0.44 | 0.21 |
| FT | 0.52 | 0.29 | 0.14 | 0.19 |
| GT | 0.37 | 0.10 | 0.16 | 0.15 |
| HT | 1.02 | 1.14 | 1.69 | 0.87 |
| IT | 0.59 | 0.38 | 0.08 | 0.81 |
| KT | 0.89 | 0.87 | 0.77 | 0.72 |
| LT | 0.32 | 0.10 | 0.07 | 0.06 |
| MT | 0.53 | 0.15 | 0.21 | 0.10 |
| NT | 0.84 | 0.69 | 1.29 | 0.40 |
| PT | 0.05 | 0.01 | 0.00 | 0.03 |
| QT | 0.73 | 0.39 | 0.30 | 0.36 |
| RT | 0.92 | 0.51 | 1.41 | 0.40 |
| ST | 0.81 | 0.47 | 0.47 | 0.63 |
| TT | 0.41 | 0.22 | 0.21 | 0.82 |
| VT | 0.61 | 0.47 | 0.24 | 1.13 |
| WT | 0.55 | 0.20 | 0.09 | 0.14 |
| YT | 0.90 | 0.48 | 0.05 | 0.28 |
| AV | 0.45 | 0.23 | 0.11 | 0.12 |
| CV | 0.51 | 0.52 | 0.20 | 0.14 |
| DV | 0.35 | 0.08 | 0.01 | 0.00 |
| EV | 0.42 | 0.24 | 0.08 | 0.02 |
| FV | 0.29 | 0.13 | 0.08 | 0.02 |
| GV | 0.13 | 0.05 | 0.03 | 0.00 |
| HV | 0.79 | 0.60 | 0.83 | 0.11 |
| IV | 0.10 | 0.20 | 0.03 | 0.07 |
| KV | 0.77 | 0.52 | 0.62 | 0.10 |
| LV | 0.08 | 0.04 | 0.00 | 0.01 |
| MV | 0.09 | 0.07 | 0.02 | 0.01 |
| NV | 0.84 | 0.26 | 0.37 | 0.01 |
| PV | 0.01 | 0.00 | 0.00 | 0.02 |
| QV | 0.39 | 0.24 | 0.10 | 0.04 |
| RV | 0.69 | 0.54 | 0.68 | 0.05 |
| SV | 0.46 | 0.23 | 0.18 | 0.13 |
| TV | 0.01 | 0.00 | 0.00 | 0.00 |
| VV | 0.18 | 0.23 | 0.07 | 0.17 |
| WV | 0.12 | 0.08 | 0.02 | 0.01 |
| YV | 0.34 | 0.12 | 0.10 | 0.00 |

| RVD | A | C | G | T |
|---|---|---|---|---|
| AW | 0.00 | 0.00 | 0.00 | 0.00 |
| CW | 0.00 | 0.00 | 0.00 | 0.00 |
| DW | 0.00 | 0.00 | 0.00 | 0.01 |
| EW | 0.00 | 0.00 | 0.00 | 0.00 |
| FW | 0.00 | 0.00 | 0.00 | 0.01 |
| GW | 0.01 | 0.01 | 0.00 | 0.02 |
| HW | 0.00 | 0.00 | 0.00 | 0.01 |
| IW | 0.00 | 0.01 | 0.00 | 0.01 |
| KW | 0.00 | 0.00 | 0.00 | 0.01 |
| LW | 0.00 | 0.00 | 0.00 | 0.01 |
| MW | 0.00 | 0.00 | 0.00 | 0.02 |
| NW | 0.01 | 0.00 | 0.02 | 0.00 |
| PW | 0.01 | 0.00 | 0.00 | 0.01 |

| RVD | A | C | G | T |
|---|---|---|---|---|
| AY | 0.02 | 0.00 | 0.00 | 0.01 |
| CY | 0.01 | 0.00 | 0.00 | 0.01 |
| DY | 0.00 | 0.00 | 0.00 | 0.01 |
| EY | 0.00 | 0.00 | 0.00 | 0.01 |
| FY | 0.00 | 0.00 | 0.00 | 0.01 |
| GY | 0.02 | 0.00 | 0.00 | 0.01 |
| HY | 0.14 | 0.00 | 0.00 | 0.01 |
| IY | 0.00 | 0.00 | 0.00 | 0.00 |
| KY | 0.07 | 0.01 | 0.00 | 0.01 |
| LY | 0.00 | 0.00 | 0.00 | 0.01 |
| MY | 0.00 | 0.00 | 0.00 | 0.00 |
| NY | 0.09 | 0.01 | 0.00 | 0.00 |
| PY | 0.04 | 0.00 | 0.00 | 0.00 |

FIGURE 2G

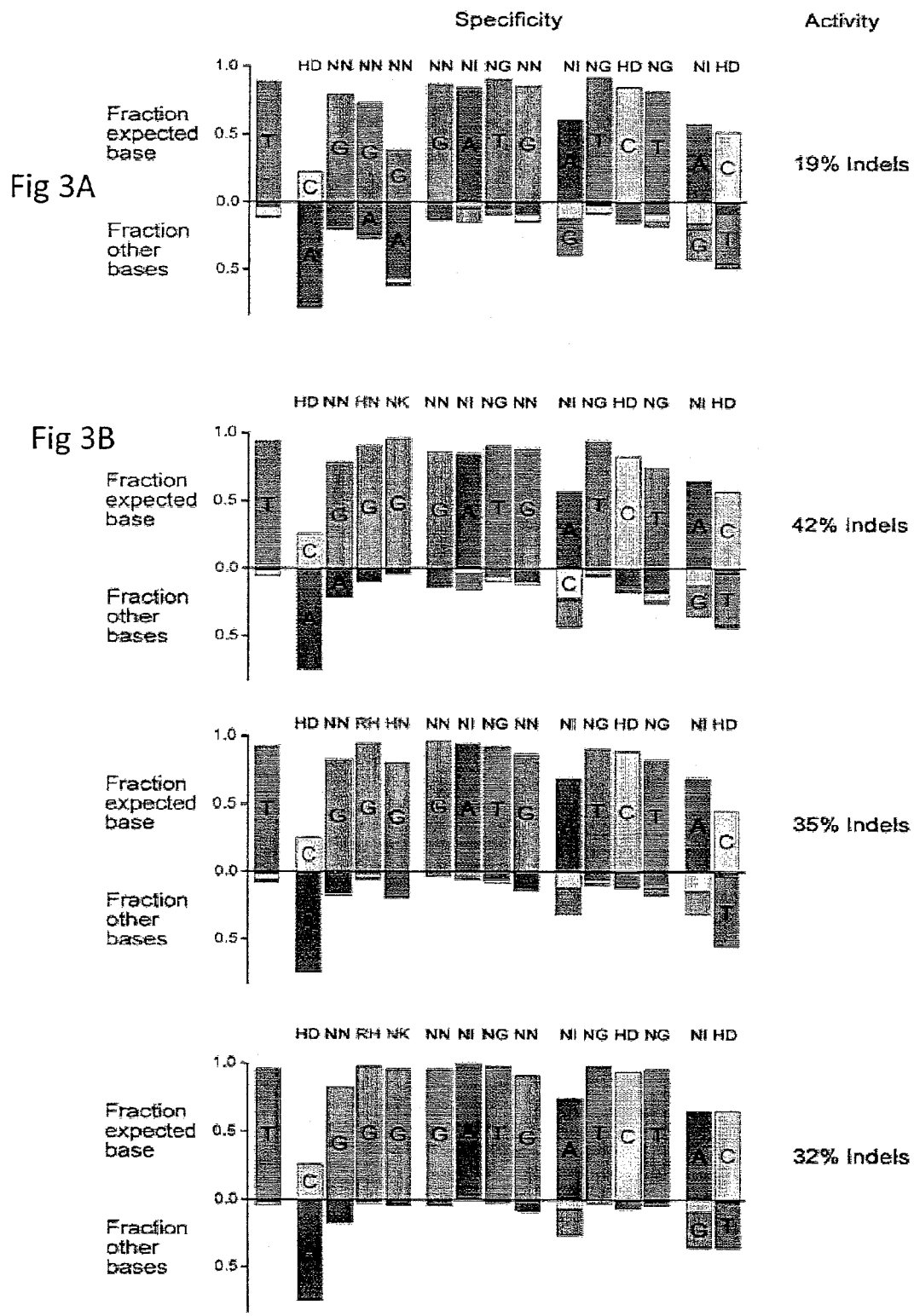

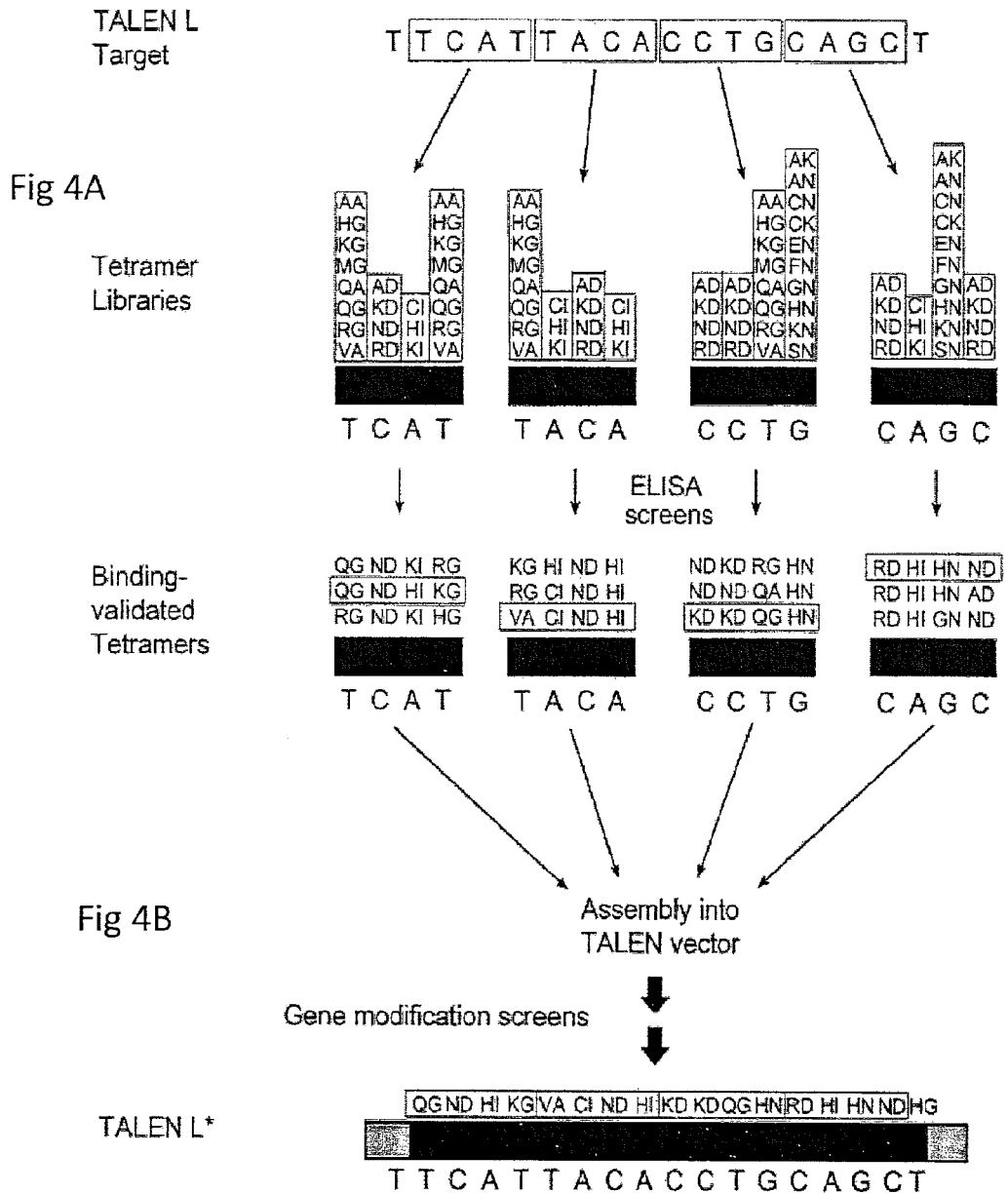

| RVD | N | Score | SE |
|---|---|---|---|
| \multicolumn{4}{c}{TCAT} | | | |
| KI | 14 | 1.51 | 0.42 |
| HI | 15 | 1.15 | 0.44 |
| CI | 15 | 0.37 | 0.15 |

| RVD | N | Score | SE |
|---|---|---|---|
| ATAC | | | |
| HI | 15 | 1.45 | 0.14 |
| CI | 15 | 0.88 | 0.20 |
| KI | 13 | 0.61 | 0.14 |

| TACA | | | |
|---|---|---|---|
| RD | 17 | 1.17 | 0.24 |
| KD | 26 | 1.13 | 0.20 |
| ND | 24 | 1.07 | 0.28 |
| AD | 18 | 0.57 | 0.20 |

| CCTG | | | |
|---|---|---|---|
| ND | 22 | 1.86 | 0.39 |
| KD | 29 | 0.91 | 0.21 |
| AD | 18 | 0.89 | 0.31 |
| RD | 21 | 0.32 | 0.16 |

| ATTG | | | |
|---|---|---|---|
| CN | 8 | 1.84 | 1.19 |
| HN | 16 | 1.83 | 0.31 |
| FN | 12 | 1.68 | 0.77 |
| CK | 15 | 0.91 | 0.20 |
| GN | 7 | 0.76 | 0.39 |
| AN | 11 | 0.74 | 0.28 |
| KN | 20 | 0.69 | 0.15 |
| AK | 10 | 0.68 | 0.32 |
| SN | 19 | 0.61 | 0.16 |
| EN | 13 | 0.57 | 0.21 |

| CAGA | | | |
|---|---|---|---|
| HN | 26 | 2.54 | 0.43 |
| KN | 17 | 1.41 | 0.42 |
| SN | 30 | 0.80 | 0.29 |
| AN | 8 | 0.78 | 0.38 |
| FN | 10 | 0.66 | 0.48 |
| EN | 27 | 0.64 | 0.17 |
| CN | 5 | 0.25 | 0.18 |
| GN | 7 | 0.07 | 0.05 |
| CK | 7 | 0.02 | 0.02 |
| AK | 9 | 0.01 | 0.01 |

| TCAT | | | |
|---|---|---|---|
| QG | 8 | 2.22 | 0.76 |
| HG | 4 | 1.95 | 0.83 |
| RG | 5 | 1.87 | 0.60 |
| KG | 4 | 1.50 | 0.40 |
| VA | 11 | 0.20 | 0.09 |
| AA | 5 | 0.10 | 0.04 |
| MG | 3 | 0.07 | 0.03 |
| QA | 4 | 0.02 | 0.01 |

| TACA | | | |
|---|---|---|---|
| KG | 11 | 2.08 | 0.39 |
| RG | 12 | 1.60 | 0.28 |
| HG | 10 | 1.52 | 0.38 |
| VA | 10 | 1.19 | 0.30 |
| AA | 10 | 0.83 | 0.30 |
| QA | 14 | 0.37 | 0.16 |
| QG | 8 | 0.21 | 0.07 |
| MG | 10 | 0.08 | 0.04 |

FIGURE 4D

| T | C | A | T | Signal |
|---|---|---|---|---|
| QG | ND | KI | RG | 5.32 |
| QG | ND | HI | KG | 4.96 |
| RG | ND | KI | HG | 4.14 |
| QG | AD | HI | KG | 4.13 |
| HG | RD | HI | HG | 3.90 |
| HG | KD | KI | MG | 2.94 |
| KG | ND | KI | QA | 2.36 |
| RG | RD | HI | AA | 2.25 |
| KG | AD | CI | HG | 2.14 |
| QG | KD | KI | AA | 1.82 |
| RG | ND | KI | QA | 1.53 |
| QG | RD | HI | QG | 1.47 |
| VA | RD | KI | HG | 1.11 |
| HG | AD | CI | QG | 1.07 |
| RG | KD | KI | KG | 1.06 |
| KG | KD | KI | VA | 0.94 |
| KG | KD | CI | AA | 0.75 |
| RG | ND | CI | MG | 0.66 |
| QG | RD | CI | QG | 0.49 |
| VA | KD | HI | RG | 0.42 |
| VA | ND | HI | HG | 0.25 |
| AA | KD | KI | MG | 0.21 |
| VA | KD | CI | RG | 0.20 |
| AA | ND | HI | RG | 0.17 |
| MG | AD | KI | AA | 0.14 |
| HG | KD | CI | QA | 0.13 |
| AA | ND | KI | KG | 0.11 |
| VA | AD | KI | VA | 0.10 |
| VA | KD | HI | AA | 0.09 |
| QG | RD | CI | VA | 0.07 |
| VA | ND | HI | VA | 0.06 |
| MG | AD | CI | MG | 0.05 |
| VA | AD | HI | QA | 0.04 |
| AA | ND | KI | VA | 0.03 |
| VA | AD | HI | AA | 0.03 |
| QA | KD | HI | VA | 0.03 |
| QA | ND | CI | QG | 0.03 |
| MG | AD | CI | AA | 0.03 |
| AA | AD | CI | HG | 0.02 |
| VA | AD | HI | QA | 0.01 |
| QA | AD | HI | HG | 0.01 |
| QG | AD | CI | AA | 0.01 |
| VA | AD | CI | MG | 0.01 |
| QA | KD | CI | MG | 0.01 |

| T | A | C | A | signal |
|---|---|---|---|---|
| KG | HI | ND | HI | 2.13 |
| RG | CI | ND | HI | 1.88 |
| HG | HI | RD | HI | 1.82 |
| KG | HI | KD | HI | 1.75 |
| HG | HI | ND | HI | 1.43 |
| KG | CI | KD | HI | 1.39 |
| KG | CI | ND | KI | 1.27 |
| AA | HI | AD | HI | 1.25 |
| RG | KI | ND | KI | 1.25 |
| KG | CI | KD | HI | 1.24 |
| VA | HI | ND | KI | 1.20 |
| VA | CI | ND | HI | 1.19 |
| HG | KI | KD | KI | 1.18 |
| KG | KI | KD | KI | 1.18 |
| RG | HI | RD | KI | 1.15 |
| RG | KI | AD | HI | 1.10 |
| KG | HI | RD | CI | 1.08 |
| HG | KI | KD | KI | 1.01 |
| RG | KI | ND | KI | 0.99 |
| QA | HI | AD | HI | 0.98 |
| AA | HI | KD | KI | 0.95 |
| VA | KI | KD | KI | 0.94 |
| VA | KI | RD | HI | 0.93 |
| AA | HI | RD | KI | 0.85 |
| VA | HI | RD | HI | 0.84 |
| KG | KI | KD | CI | 0.83 |
| AA | HI | AD | HI | 0.80 |
| HG | HI | RD | HI | 0.72 |
| RG | CI | KD | HI | 0.71 |
| RG | KI | RD | KI | 0.65 |
| HG | CI | RD | HI | 0.59 |
| HG | CI | KD | CI | 0.59 |
| RG | CI | KD | KI | 0.55 |
| KG | KI | ND | CI | 0.54 |
| RG | KI | RD | CI | 0.49 |
| QA | KI | KD | HI | 0.49 |
| QA | HI | KD | CI | 0.47 |
| RG | CI | RD | KI | 0.44 |
| QA | KI | KD | HI | 0.41 |
| VA | HI | AD | KI | 0.38 |
| VA | HI | RD | CI | 0.31 |
| RG | CI | AD | HI | 0.30 |
| QG | CI | KD | HI | 0.24 |
| QG | CI | KD | HI | 0.23 |

| T | A | C | A | Signal |
|---|---|---|---|---|
| AA | KI | KD | CI | 0.18 |
| HG | KI | ND | HI | 0.17 |
| MG | HI | ND | CI | 0.16 |
| QG | HI | ND | CI | 0.15 |
| RG | KI | AD | KI | 0.13 |
| MG | HI | KD | KI | 0.13 |
| HG | CI | KD | CI | 0.12 |
| AA | HI | AD | KI | 0.11 |
| QG | CI | ND | KI | 0.11 |
| QA | KI | ND | KI | 0.09 |
| VA | CI | ND | CI | 0.09 |
| QG | CI | ND | KI | 0.09 |
| QA | CI | RD | HI | 0.08 |
| VA | CI | ND | CI | 0.07 |
| MG | CI | KD | HI | 0.06 |
| KG | KI | AD | KI | 0.06 |
| KG | CI | RD | CI | 0.04 |
| QA | CI | KD | CI | 0.03 |
| QG | KI | KD | CI | 0.03 |
| VA | CI | ND | HI | 0.03 |
| AA | KI | AD | HI | 0.02 |
| AA | HI | AD | CI | 0.02 |
| MG | KI | ND | HI | 0.02 |
| AA | KI | RD | HI | 0.01 |
| QA | CI | KD | CI | 0.01 |
| QG | CI | ND | CI | 0.01 |
| MG | KI | ND | KI | 0.01 |
| QA | CI | AD | HI | 0.01 |
| QA | KI | AD | HI | 0.01 |
| HG | KI | ND | KI | 0.00 |
| QA | KI | AD | HI | 0.00 |
| QA | CI | KD | CI | 0.00 |
| MG | HI | AD | CI | 0.00 |
| AA | CI | RD | CI | 0.00 |
| QA | KI | KD | CI | 0.00 |
| QG | KI | AD | CI | 0.00 |
| MG | CI | AD | HI | 0.00 |
| MG | CI | ND | CI | 0.00 |
| MG | CI | ND | CI | 0.00 |
| QA | CI | AD | KI | 0.00 |
| MG | KI | RD | CI | 0.00 |

FIGURE 4F

| C | C | T | G | signal |
|---|---|---|---|---|
| ND | KD | RG | HN | 1.13 |
| ND | ND | QA | HN | 0.99 |
| ND | ND | HG | KN | 0.89 |
| ND | KD | KG | HN | 0.88 |
| AD | RD | HG | HN | 0.88 |
| KD | ND | QG | HN | 0.81 |
| AD | KD | RG | HN | 0.77 |
| ND | KD | HG | AN | 0.75 |
| ND | RD | KG | CN | 0.70 |
| KD | RD | RG | CN | 0.62 |
| RD | RD | KG | HN | 0.60 |
| KD | KD | KG | FN | 0.56 |
| ND | RD | VA | HN | 0.55 |
| KD | KD | KG | CN | 0.53 |
| ND | KD | HG | HN | 0.52 |
| KD | KD | QG | HN | 0.49 |
| KD | KD | QA | HN | 0.48 |
| ND | AD | KG | HN | 0.43 |
| AD | KD | QA | HN | 0.41 |
| RD | ND | KG | KN | 0.38 |
| ND | ND | KG | SN | 0.37 |
| KD | KD | QG | HN | 0.36 |
| KD | ND | KG | CK | 0.34 |
| AD | RD | KG | SN | 0.31 |
| ND | AD | QG | HN | 0.29 |
| ND | KD | KG | CK | 0.26 |
| AD | ND | AA | HN | 0.26 |
| AD | KD | RG | CN | 0.26 |
| ND | RD | VA | CK | 0.24 |
| ND | RD | QA | KN | 0.20 |
| KD | ND | AA | KN | 0.19 |
| KD | ND | HG | CK | 0.17 |
| AD | ND | MG | HN | 0.16 |
| KD | KD | QA | AK | 0.14 |
| KD | KD | VA | CN | 0.13 |
| KD | ND | AA | FN | 0.10 |
| AD | AD | RG | KN | 0.10 |
| KD | AD | QG | HN | 0.09 |
| KD | RD | QA | CK | 0.09 |
| KD | RD | QG | CN | 0.08 |
| RD | ND | RG | SN | 0.08 |
| RD | AD | KG | AK | 0.07 |
| AD | KD | RG | CK | 0.05 |
| ND | AD | QA | KN | 0.05 |
| KD | ND | QA | FN | 0.05 |

| C | C | T | G | signal |
|---|---|---|---|---|
| RD | KD | AA | EN | 0.04 |
| RD | RD | AA | CK | 0.03 |
| ND | RD | VA | AN | 0.03 |
| RD | AD | QA | HN | 0.03 |
| RD | AD | KG | FN | 0.03 |
| KD | AD | HG | SN | 0.03 |
| KD | AD | HG | SN | 0.02 |
| AD | KD | QA | SN | 0.02 |
| KD | ND | AA | EN | 0.02 |
| RD | KD | QG | EN | 0.02 |
| KD | KD | AA | GN | 0.02 |
| RD | KD | QG | SN | 0.01 |
| AD | RD | VA | FN | 0.01 |
| RD | RD | AA | EN | 0.01 |
| RD | KD | QG | EN | 0.01 |
| KD | KD | QA | GN | 0.01 |
| RD | AD | KG | SN | 0.01 |
| ND | AD | MG | KN | 0.01 |
| AD | RD | MG | SN | 0.01 |
| KD | AD | QA | CK | 0.01 |
| RD | KD | QG | EN | 0.01 |
| ND | RD | QA | GN | 0.01 |
| RD | KD | QA | GN | 0.01 |
| KD | AD | QA | KN | 0.01 |
| KD | AD | QA | CK | 0.00 |
| AD | KD | QG | AN | 0.00 |
| ND | AD | QG | AK | 0.00 |
| AD | AD | KG | CK | 0.00 |
| RD | AD | KG | SN | 0.00 |
| KD | AD | RG | GN | 0.00 |
| RD | ND | VA | SN | 0.00 |
| ND | AD | AA | GN | 0.00 |
| ND | AD | MG | AN | 0.00 |
| AD | KD | QG | SN | 0.00 |
| AD | RD | QA | GN | 0.00 |
| RD | ND | QA | EN | 0.00 |
| RC | AD | VA | CN | 0.00 |
| AD | AD | AA | AN | 0.00 |
| ND | AD | VA | SN | 0.00 |
| AD | AD | MG | EN | 0.00 |
| KD | AD | AA | GN | 0.00 |
| KD | AD | QG | FN | 0.00 |
| RD | AD | MG | CN | 0.00 |
| RD | AD | MG | EN | 0.00 |
| KD | AD | QG | KN | 0.00 |

| C | A | G | C | signal |
|---|---|---|---|---|
| RD | HI | HN | ND | 2.05 |
| RD | HI | HN | AD | 0.46 |
| RD | HI | GN | ND | 0.34 |
| ND | HI | CN | ND | 0.31 |
| RD | HI | CN | KD | 0.16 |
| RD | HI | GN | ND | 0.14 |
| KD | KI | CK | ND | 0.08 |
| KD | HI | CK | ND | 0.08 |
| RD | HI | CN | RD | 0.06 |
| AD | HI | HN | RD | 0.05 |
| AD | HI | CK | ND | 0.05 |
| KD | KI | CK | ND | 0.05 |
| KD | KI | CN | ND | 0.03 |
| KD | HI | CN | KD | 0.02 |
| AD | HI | SN | KD | 0.02 |
| ND | KI | KN | ND | 0.02 |
| ND | AI | KN | ND | 0.02 |
| AD | HI | SN | RD | 0.02 |
| RD | KI | SN | KD | 0.02 |
| AD | HI | AN | ND | 0.02 |
| KD | HI | AN | RD | 0.02 |
| KD | HI | AK | ND | 0.01 |
| KD | CI | AN | KD | 0.01 |
| ND | KI | FN | AD | 0.01 |
| RD | KI | SN | RD | 0.01 |
| KD | HI | GN | RD | 0.01 |
| KD | HI | GN | RD | 0.01 |
| ND | CI | CN | KD | 0.01 |
| KD | CI | CN | ND | 0.01 |
| RD | KI | AK | KD | 0.01 |
| ND | CI | KN | ND | 0.01 |
| RD | KI | CN | KD | 0.01 |
| RD | KI | AK | RD | 0.01 |
| ND | HI | GN | RD | 0.01 |
| RD | KI | CK | RD | 0.01 |
| RD | HI | AK | RD | 0.01 |
| AD | HI | AK | ND | 0.01 |
| RD | HI | FN | KD | 0.01 |
| AD | HI | AK | ND | 0.01 |
| AD | KI | CK | ND | 0.01 |
| RD | CI | CK | ND | 0.01 |
| RD | KI | CN | RD | 0.01 |
| ND | HI | AN | RD | 0.01 |
| KD | HI | AK | KD | 0.00 |
| RD | KI | AK | KD | 0.00 |
| RD | KI | CN | RD | 0.00 |
| KD | CI | AK | AD | 0.00 |
| AD | HI | AK | KD | 0.00 |
| AD | KI | CK | RD | 0.00 |
| AD | KI | AK | RD | 0.00 |
| RD | KI | AK | AD | 0.00 |
| KD | CI | AK | ND | 0.00 |
| ND | CI | CN | RD | 0.00 |
| AD | CI | FN | ND | 0.00 |
| KD | HI | GN | AD | 0.00 |
| KD | KI | GN | RD | 0.00 |
| KD | HI | GN | AD | 0.00 |
| AD | KI | GN | AD | 0.00 |
| AD | CI | CN | KD | 0.00 |
| ND | KI | FN | AD | 0.00 |
| AD | HI | CN | RD | 0.00 |
| AD | HI | FN | RD | 0.00 |
| AD | CI | FN | AD | 0.00 |
| RD | CI | AN | KD | 0.00 |
| RD | CI | AN | KD | 0.00 |
| KD | HI | GN | AD | 0.00 |
| KD | KI | GN | RD | 0.00 |
| ND | KI | GN | RD | 0.00 |
| AD | HI | AN | KD | 0.00 |

| C | A | G | C | signal |
|---|---|---|---|---|
| AD | CI | CK | KD | 0.00 |
| ND | CI | AK | KD | 0.00 |
| RD | HI | CN | AD | 0.00 |
| AD | CI | FN | RD | 0.00 |
| AD | KI | AK | RD | 0.00 |
| KD | CI | AN | ND | 0.00 |
| ND | HI | CN | AD | 0.00 |
| AD | CI | HN | RD | 0.00 |
| AD | CI | AN | ND | 0.00 |
| KD | HI | AK | AD | 0.00 |
| RD | CI | AN | RD | 0.00 |
| ND | HI | FN | KD | 0.00 |
| KD | CI | GN | ND | 0.00 |
| RD | CI | AN | RD | 0.00 |
| ND | KI | CN | RD | 0.00 |
| RD | HI | CK | AD | 0.00 |
| RD | CI | FN | KD | 0.00 |
| AD | KI | CN | KD | 0.00 |
| RD | CI | FN | KD | 0.00 |
| AD | HI | GN | RD | 0.00 |
| AD | CI | AK | AD | 0.00 |
| AD | CI | GN | RD | 0.00 |
| KD | CI | AK | KD | 0.00 |
| KD | HI | CN | AD | 0.00 |
| RD | CI | FN | RD | 0.00 |
| RD | CI | GN | AD | 0.00 |
| AD | CI | GN | ND | 0.00 |
| KD | CI | CN | KD | 0.00 |
| AD | HI | CN | AD | 0.00 |
| AD | CI | GN | ND | 0.00 |
| AD | CI | AN | RD | 0.00 |
| KD | CI | AK | AD | 0.00 |
| AD | CI | FN | ND | 0.00 |
| ND | HI | KN | RD | 0.00 |
| KD | CI | SN | KD | 0.00 |
| AD | KI | CN | RD | 0.00 |
| AD | KI | SN | RD | 0.00 |
| KD | KI | AK | RD | 0.00 |
| AD | CI | CN | AD | 0.00 |
| RD | KI | SN | KD | 0.00 |
| KD | KI | GN | RD | 0.00 |
| RD | HI | FN | KD | 0.00 |
| KD | CI | GN | RD | 0.00 |
| RD | KI | KN | AD | 0.00 |
| AD | KI | FN | ND | 0.00 |
| AD | HI | FN | ND | 0.00 |
| ND | HI | EN | RD | 0.00 |
| RD | HI | AK | AD | 0.00 |
| AD | CI | HN | RD | 0.00 |
| RD | HI | EN | RD | 0.00 |
| RD | CI | CN | KD | 0.00 |
| KD | KI | EN | RD | 0.00 |
| AD | CI | GN | RD | 0.00 |
| KD | CI | EN | RD | 0.00 |
| AD | CI | AK | RD | 0.00 |
| ND | KI | EN | RD | 0.00 |
| ND | CI | GN | KD | 0.00 |
| RD | CI | AK | ND | 0.00 |
| RD | CI | CN | RD | 0.00 |
| KD | CI | KN | AD | 0.00 |
| ND | KI | AN | RD | 0.00 |
| RD | HI | EN | RD | 0.00 |
| ND | CI | AN | KD | 0.00 |
| ND | CI | GN | AD | 0.00 |
| AD | CI | AK | ND | 0.00 |
| RD | KI | FN | AD | 0.00 |
| KD | HI | EN | AD | 0.00 |
| KD | CI | AN | AD | 0.00 |

FIGURE 4G

| C | T | T | C | signal |
|---|---|---|---|---|
| ND | KG | HG | KD | 3.05 |
| RD | AA | HG | RD | 3.01 |
| ND | KG | HG | ND | 3.00 |
| RD | RG | KG | ND | 2.87 |
| ND | RG | KG | ND | 2.55 |
| RD | HG | RG | KD | 2.51 |
| KD | QG | HG | ND | 2.48 |
| ND | AA | QG | ND | 2.42 |
| KD | QA | HG | RD | 2.14 |
| RD | MG | KG | ND | 2.13 |
| KD | AA | QG | ND | 1.99 |
| ND | VA | KG | RD | 1.97 |
| RD | AA | QG | AD | 1.89 |
| KD | AA | QG | ND | 1.77 |
| ND | KG | QG | RD | 1.73 |
| RD | RG | RG | KD | 1.64 |
| RD | KG | KG | AD | 1.58 |
| ND | RG | AA | ND | 1.54 |
| AD | AA | RG | ND | 1.39 |
| RD | RG | KG | AD | 1.38 |
| RD | RG | MG | ND | 1.21 |
| AD | MG | HG | KD | 1.14 |
| ND | HG | QA | ND | 1.14 |
| AD | AA | RG | AD | 1.12 |
| ND | HG | RG | ND | 1.12 |
| AD | VA | RG | ND | 1.12 |
| ND | AA | RG | AD | 1.04 |
| RD | QG | MG | ND | 1.00 |
| ND | VA | KG | RD | 0.93 |
| KD | QG | QG | ND | 0.92 |
| RD | HG | RG | ND | 0.89 |
| KD | QG | HG | RD | 0.85 |
| ND | VA | KG | RD | 0.83 |
| ND | KG | AA | ND | 0.80 |
| ND | KG | VA | ND | 0.75 |
| RD | VA | RG | RD | 0.71 |
| RD | HG | KG | ND | 0.66 |
| AD | QG | RG | RD | 0.62 |
| KD | KG | AA | ND | 0.59 |
| RD | QG | MG | ND | 0.56 |
| RD | QG | QG | RD | 0.55 |
| ND | RG | KG | RD | 0.51 |
| KD | KG | AA | RD | 0.50 |
| AD | AA | HG | KD | 0.44 |
| KD | RG | MG | RD | 0.43 |
| RD | RG | KG | ND | 0.42 |
| RD | KG | RG | AD | 0.42 |
| KD | QA | MG | RD | 0.38 |
| RD | QA | KG | RD | 0.37 |
| AD | MG | RG | KD | 0.36 |
| KD | VA | MG | AD | 0.36 |
| KD | AA | KG | AD | 0.36 |
| ND | VA | MG | AD | 0.33 |
| AD | HG | MG | RD | 0.32 |
| RD | HG | QA | RD | 0.31 |
| KD | QG | MG | ND | 0.30 |
| RD | QG | RG | ND | 0.30 |
| AD | QG | MG | RD | 0.28 |
| KD | MG | QG | ND | 0.28 |
| RD | KG | VA | ND | 0.25 |
| ND | MG | AA | ND | 0.25 |
| AD | KG | QG | ND | 0.23 |
| RD | KG | VA | ND | 0.20 |
| AD | MG | KG | AD | 0.19 |
| RD | AA | MG | ND | 0.19 |
| AD | KG | QG | AD | 0.19 |

| C | T | T | C | signal |
|---|---|---|---|---|
| ND | MG | AA | KD | 0.17 |
| AD | KG | RG | ND | 0.17 |
| KD | QA | MG | RD | 0.17 |
| RD | HG | AA | AD | 0.17 |
| AD | KG | QA | KD | 0.16 |
| AD | QG | KG | AD | 0.16 |
| ND | KG | VA | AD | 0.15 |
| ND | QA | MG | AD | 0.15 |
| KD | RG | VA | ND | 0.14 |
| RD | HG | KG | RD | 0.13 |
| RD | AA | MG | ND | 0.11 |
| AD | HG | QA | KD | 0.08 |
| ND | QG | AA | AD | 0.08 |
| ND | AA | MG | RD | 0.07 |
| AD | QG | AA | KD | 0.06 |
| KD | RG | VA | ND | 0.06 |
| KD | QA | VA | AD | 0.05 |
| RD | QA | MG | AD | 0.05 |
| AD | QA | RG | AD | 0.05 |
| RD | VA | QG | AD | 0.05 |
| RD | RG | VA | AD | 0.05 |
| RD | QG | QA | KD | 0.04 |
| AD | HG | RG | RD | 0.04 |
| RD | QA | QA | ND | 0.03 |
| AD | MG | QG | AD | 0.03 |
| KD | RG | VA | ND | 0.03 |
| AD | HG | AA | AD | 0.02 |
| AD | QA | HG | RD | 0.02 |
| RD | KG | RG | RD | 0.02 |
| AD | MG | RG | AD | 0.02 |
| AD | RG | QG | ND | 0.02 |
| ND | QG | VA | KD | 0.02 |
| AD | HG | MG | ND | 0.01 |
| RD | MG | AA | AD | 0.01 |
| KD | QG | QA | ND | 0.01 |
| AD | AA | QA | KD | 0.01 |
| KD | QA | QA | RD | 0.01 |
| AD | RG | VA | AD | 0.01 |
| ND | QA | VA | KD | 0.00 |
| RD | RG | KG | AD | 0.00 |
| ND | QA | VA | RD | 0.00 |
| AD | MG | QG | AD | 0.00 |
| AD | QA | AA | ND | 0.00 |
| AD | HG | AA | KD | 0.00 |
| RD | MG | VA | KD | 0.00 |
| RD | VA | QA | AD | 0.00 |
| AD | KG | VA | AD | 0.00 |
| AD | VA | AA | ND | 0.00 |
| AD | MG | QA | RD | 0.00 |
| ND | KG | VA | AD | 0.00 |
| KD | QG | MG | RD | 0.00 |
| AD | VA | VA | RD | 0.00 |
| ND | MG | MG | KD | 0.00 |
| AD | AA | AA | AD | 0.00 |
| AD | QA | AA | KD | 0.00 |
| RD | QA | MG | AD | 0.00 |
| ND | VA | RG | ND | 0.00 |
| RD | AA | AA | ND | 0.00 |
| AD | QA | VA | KD | 0.00 |
| RD | AA | AA | ND | 0.00 |
| KD | MG | VA | ND | 0.00 |
| KD | VA | AA | AD | 0.00 |
| AD | MG | AA | ND | 0.00 |
| AD | VA | AA | AD | 0.00 |
| AD | VA | QA | AD | 0.00 |

| C | A | G | A | signal |
|---|---|---|---|---|
| RD | HI | HN | HI | 1.33 |
| KD | HI | HN | KI | 1.30 |
| RD | HI | SN | KI | 1.08 |
| ND | HI | HN | KI | 1.08 |
| KD | HI | HN | KI | 1.03 |
| KD | HI | SN | KI | 1.03 |
| KD | HI | HN | KI | 1.01 |
| KD | HI | KN | CI | 0.95 |
| KD | HI | FN | HI | 0.84 |
| KD | HI | KN | CI | 0.82 |
| KD | CI | HN | HI | 0.81 |
| KD | HI | HN | KI | 0.75 |
| KD | KI | KN | HI | 0.62 |
| RD | KI | HN | KI | 0.60 |
| KD | CI | HN | HI | 0.59 |
| ND | KI | KN | HI | 0.57 |
| KD | HI | SN | HI | 0.57 |
| RD | HI | HN | HI | 0.55 |
| KD | CI | AN | KI | 0.55 |
| AD | KI | HN | HI | 0.51 |
| RD | HI | EN | HI | 0.51 |
| AD | HI | SN | HI | 0.47 |
| KD | HI | KN | CI | 0.44 |
| RD | CI | HN | KI | 0.42 |
| RD | CI | HN | CI | 0.42 |
| ND | KI | HN | CI | 0.39 |
| KD | HI | EN | HI | 0.38 |
| ND | HI | EN | HI | 0.36 |
| KD | HI | EN | KI | 0.34 |
| RD | HI | EN | KI | 0.33 |
| KD | HI | HN | KI | 0.31 |
| RD | HI | SN | CI | 0.29 |
| ND | KI | FN | HI | 0.29 |
| AD | CI | HN | HI | 0.28 |
| RD | HI | KN | KI | 0.28 |
| RD | CI | HN | CI | 0.27 |
| RD | HI | EN | CI | 0.27 |
| KD | HI | SN | HI | 0.25 |
| RD | HI | EN | HI | 0.23 |
| KD | HI | AN | CI | 0.22 |
| KD | HI | AN | CI | 0.22 |
| RD | HI | EN | KI | 0.21 |
| KD | CI | HN | HI | 0.20 |
| RD | HI | HN | HI | 0.19 |
| KD | CI | HN | HI | 0.17 |
| ND | HI | CN | KI | 0.17 |
| KD | KI | HN | KI | 0.15 |
| ND | KI | SN | HI | 0.15 |
| RD | HI | EN | CI | 0.14 |
| KD | CI | HN | CI | 0.14 |
| RD | KI | KN | CI | 0.14 |
| RD | HI | EN | CI | 0.12 |
| KD | CI | HN | CI | 0.12 |
| AD | KI | SN | HI | 0.10 |
| RD | CI | HN | CI | 0.10 |
| RD | CI | KN | KI | 0.09 |
| AD | KI | SN | HI | 0.08 |
| RD | KI | AN | KI | 0.08 |
| RD | KI | SN | KI | 0.08 |
| RD | CI | KN | KI | 0.08 |
| KD | HI | EN | CI | 0.07 |
| AD | HI | GN | HI | 0.06 |
| ND | HI | EN | KI | 0.06 |
| AD | HI | KN | CI | 0.05 |
| KD | KI | SN | KI | 0.05 |
| RD | HI | CN | CI | 0.05 |
| AD | KI | SN | HI | 0.05 |
| AD | CI | KN | HI | 0.04 |
| RD | CI | KN | CI | 0.04 |
| RD | HI | KN | HI | 0.04 |
| KD | CI | KN | KI | 0.04 |
| AD | KI | SN | HI | 0.03 |
| AD | CI | KN | HI | 0.03 |

| C | A | G | A | signal |
|---|---|---|---|---|
| RD | HI | FN | CI | 0.03 |
| RD | CI | KN | HI | 0.03 |
| RD | HI | GN | CI | 0.03 |
| AD | KI | CK | HI | 0.02 |
| KD | KI | AN | KI | 0.02 |
| RD | KI | EN | CI | 0.02 |
| ND | HI | FN | CI | 0.02 |
| RD | KI | SN | KI | 0.02 |
| AD | HI | EN | HI | 0.02 |
| RD | KI | SN | KI | 0.01 |
| AD | HI | AN | CI | 0.01 |
| ND | KI | SN | KI | 0.01 |
| ND | KI | EN | KI | 0.01 |
| AD | HI | AN | CI | 0.01 |
| KD | CI | SN | KI | 0.01 |
| KD | HI | KN | KI | 0.01 |
| RD | CI | EN | HI | 0.01 |
| KD | CI | SN | CI | 0.01 |
| RD | HI | AK | KI | 0.01 |
| KD | KI | EN | KI | 0.01 |
| KD | CI | HN | HI | 0.00 |
| AD | CI | EN | CI | 0.00 |
| AD | KI | EN | HI | 0.00 |
| AD | HI | SN | KI | 0.00 |
| ND | CI | SN | CI | 0.00 |
| AD | CI | SN | KI | 0.00 |
| AD | CI | EN | HI | 0.00 |
| AD | CI | SN | KI | 0.00 |
| KD | KI | AK | KI | 0.00 |
| AD | CI | AK | CI | 0.00 |
| RD | KI | AK | CI | 0.00 |
| ND | CI | CK | HI | 0.00 |
| RD | CI | HN | CI | 0.00 |
| KD | KI | GN | KI | 0.00 |
| KD | HI | CK | KI | 0.00 |
| RD | CI | CN | CI | 0.00 |
| ND | CI | AK | HI | 0.00 |
| AD | CI | FN | HI | 0.00 |
| ND | KI | FN | CI | 0.00 |
| AD | KI | EN | KI | 0.00 |
| ND | KI | GN | KI | 0.00 |
| RD | CI | AK | HI | 0.00 |
| RD | CI | SN | CI | 0.00 |
| RD | CI | AK | HI | 0.00 |
| RD | CI | CK | CI | 0.00 |
| ND | KI | EN | CI | 0.00 |
| KD | KI | FN | CI | 0.00 |
| AD | KI | CN | KI | 0.00 |
| AD | HI | CK | KI | 0.00 |
| AD | CI | FN | HI | 0.00 |
| RD | CI | CN | CI | 0.00 |
| AD | HI | FN | CI | 0.00 |
| RD | CI | AK | KI | 0.00 |
| KD | CI | EN | HI | 0.00 |
| RD | HI | CK | CI | 0.00 |
| AD | CI | SN | HI | 0.00 |
| AD | CI | GN | CI | 0.00 |
| AD | CI | GN | HI | 0.00 |
| AD | HI | CK | CI | 0.00 |
| RD | HI | SN | KI | 0.00 |
| AD | CI | EN | KI | 0.00 |
| AD | CI | SN | CI | 0.00 |
| AD | CI | FN | HI | 0.00 |
| AD | KI | SN | CI | 0.00 |
| AD | CI | EN | CI | 0.00 |
| KD | CI | AK | KI | 0.00 |
| RD | KI | GN | CI | 0.00 |
| RD | CI | EN | KI | 0.00 |
| AD | KI | AN | CI | 0.00 |
| RD | CI | EN | CI | 0.00 |
| AD | CI | SN | CI | 0.00 |
| RD | KI | SN | CI | 0.00 |
| RD | CI | SN | CI | 0.00 |

FIGURE 4H

| A | T | T | G | signal |
|---|---|---|---|---|
| CI | HG | HG | CN | 3.77 |
| CI | KG | HG | FN | 3.47 |
| KI | HG | QA | HN | 1.59 |
| KI | RG | RG | FN | 1.35 |
| CI | KG | QG | HN | 1.27 |
| HI | KG | VA | AK | 1.26 |
| CI | MG | KG | HN | 1.24 |
| HI | AA | RG | GN | 1.09 |
| CI | KG | HG | FN | 1.06 |
| KI | QA | MG | AN | 1.00 |
| CI | KG | MG | HN | 0.94 |
| HI | RG | MG | HN | 0.93 |
| KI | RG | KG | EN | 0.91 |
| KI | KG | HG | CK | 0.90 |
| HI | KG | QA | SN | 0.86 |
| CI | HG | RG | KN | 0.83 |
| CI | KG | AA | HN | 0.82 |
| HI | AA | VA | HN | 0.80 |
| CI | RG | HG | CK | 0.76 |
| HI | MG | KG | HN | 0.76 |
| KI | RG | QG | AN | 0.75 |
| KI | AA | KG | HN | 0.73 |
| KI | MG | HG | HN | 0.72 |
| HI | HG | QG | SN | 0.67 |
| KI | QG | RG | KN | 0.67 |
| HI | QA | HG | FN | 0.66 |
| CI | RG | HG | CK | 0.65 |
| HI | HG | QG | CK | 0.61 |
| KI | QG | VA | CN | 0.59 |
| HI | HG | RG | SN | 0.57 |
| KI | AA | KG | CK | 0.54 |
| KI | QG | KG | EN | 0.53 |
| CI | RG | AA | KN | 0.51 |
| CI | VA | HG | KN | 0.50 |
| KI | KG | MG | AN | 0.47 |
| KI | QG | RG | EN | 0.46 |
| HI | QA | RG | GN | 0.43 |
| KI | KG | QA | EN | 0.43 |
| CI | VA | HG | KN | 0.42 |
| HI | HG | QG | SN | 0.40 |
| KI | QG | QG | CK | 0.39 |
| KI | HG | QG | SN | 0.39 |
| KI | AA | RG | SN | 0.38 |
| KI | VA | VA | HN | 0.38 |
| KI | KG | KG | KN | 0.37 |
| CI | KG | QG | AN | 0.37 |
| KI | HG | KG | KN | 0.36 |
| HI | AA | RG | CK | 0.35 |
| CI | MG | RG | AK | 0.35 |
| KI | HG | QG | SN | 0.35 |
| KI | HG | KG | KN | 0.34 |
| HI | KG | KG | CK | 0.33 |
| CI | RG | QA | FN | 0.33 |
| KI | MG | QG | KN | 0.32 |
| HI | RG | VA | AN | 0.31 |
| KI | QG | QG | AK | 0.31 |
| CI | HG | RG | SN | 0.30 |
| CI | AA | QG | HN | 0.29 |
| CI | KG | VA | CN | 0.28 |
| CI | KG | VA | CN | 0.27 |
| CI | KG | MG | AK | 0.25 |
| HI | QA | AA | FN | 0.24 |
| CI | QG | QA | HN | 0.24 |
| KI | RG | AA | KN | 0.24 |
| CI | RG | AA | FN | 0.23 |
| HI | AA | QG | GN | 0.23 |

| A | T | T | G | signal |
|---|---|---|---|---|
| CI | QA | VA | HN | 0.20 |
| KI | MG | VA | CN | 0.20 |
| KI | RG | QA | EN | 0.20 |
| KI | QA | HG | CN | 0.20 |
| KI | QG | VA | CK | 0.15 |
| KI | MG | VA | KN | 0.14 |
| KI | VA | AA | KN | 0.14 |
| KI | AA | QG | EN | 0.14 |
| KI | QA | VA | GN | 0.14 |
| CI | HG | RG | SN | 0.13 |
| CI | RG | MG | FN | 0.13 |
| HI | QA | KG | CN | 0.13 |
| HI | MG | QA | AK | 0.12 |
| CI | HG | AA | CK | 0.11 |
| HI | VA | VA | KN | 0.11 |
| CI | KG | VA | KN | 0.10 |
| HI | QG | VA | SN | 0.10 |
| KI | VA | QA | CK | 0.10 |
| KI | AA | MG | EN | 0.09 |
| CI | AA | RG | AN | 0.09 |
| KI | MG | RG | GN | 0.09 |
| KI | VA | VA | CK | 0.08 |
| CI | HG | VA | CK | 0.07 |
| CI | HG | MG | SN | 0.06 |
| KI | QG | MG | AK | 0.06 |
| CI | VA | MG | AK | 0.06 |
| CI | QG | QA | AK | 0.05 |
| CI | QA | QA | AK | 0.05 |
| CI | AA | AA | CN | 0.04 |
| KI | HG | MG | CK | 0.04 |
| HI | QG | RG | FN | 0.03 |
| CI | QA | AA | KN | 0.03 |
| HI | QA | HG | KN | 0.03 |
| HI | KG | AA | AN | 0.03 |
| HI | AA | AA | SN | 0.03 |
| KI | VA | QA | SN | 0.02 |
| CI | MG | KG | KN | 0.02 |
| KI | AA | QG | SN | 0.02 |
| CI | RG | AA | SN | 0.02 |
| CI | HG | AA | EN | 0.02 |
| HI | VA | VA | AN | 0.01 |
| CI | VA | VA | AK | 0.01 |
| CI | AA | QG | FN | 0.01 |
| KI | AA | AA | SN | 0.01 |
| CI | QG | MG | HN | 0.01 |
| CI | QA | KG | SN | 0.01 |
| CI | QG | AA | SN | 0.01 |
| CI | QA | QG | AN | 0.01 |
| HI | HG | QA | FN | 0.00 |
| CI | HG | RG | EN | 0.00 |
| CI | HG | QA | EN | 0.00 |
| KI | AA | MG | KN | 0.00 |
| CI | QA | QA | AN | 0.00 |
| HI | QG | QG | HN | 0.00 |
| CI | QA | QG | SN | 0.00 |
| CI | QA | QA | EN | 0.00 |
| CI | VA | VA | GN | 0.00 |
| HI | HG | HG | KN | 0.00 |
| KI | HG | KG | FN | 0.00 |
| CI | RG | RG | KN | 0.00 |
| CI | QA | AA | EN | 0.00 |
| HI | AA | VA | EN | 0.00 |
| HI | HG | VA | CK | 0.00 |
| CI | MG | QA | GN | 0.00 |
| HI | RG | AA | AN | 0.00 |

| A | T | A | C | signal |
|---|---|---|---|---|
| CI | KG | CI | ND | 1.29 |
| CI | VA | HI | ND | 1.26 |
| KI | HG | HI | ND | 1.17 |
| HI | VA | CI | ND | 1.13 |
| CI | KG | HI | RD | 1.04 |
| KI | RG | HI | ND | 1.01 |
| CI | KG | HI | AD | 0.98 |
| HI | KG | HI | KD | 0.94 |
| CI | QG | CI | ND | 0.88 |
| CI | HG | HI | AD | 0.87 |
| CI | HG | HI | AD | 0.87 |
| KI | QA | CI | ND | 0.82 |
| KI | RG | CI | KD | 0.81 |
| KI | RG | CI | KD | 0.81 |
| HI | HG | HI | ND | 0.81 |
| KI | RG | KI | ND | 0.79 |
| KI | VA | HI | KD | 0.78 |
| CI | RG | HI | KD | 0.74 |
| KI | RG | KI | KD | 0.73 |
| KI | AA | HI | AD | 0.60 |
| HI | KG | KI | AD | 0.56 |
| CI | HG | CI | KD | 0.55 |
| KI | MG | HI | RD | 0.53 |
| CI | HG | KI | ND | 0.50 |
| HI | QA | KI | ND | 0.48 |
| KI | KG | CI | AD | 0.45 |
| KI | QG | HI | AD | 0.44 |
| KI | HG | KI | KD | 0.44 |
| KI | RG | CI | KD | 0.36 |
| HI | KG | KI | AD | 0.36 |
| KI | VA | KI | KD | 0.31 |
| CI | KG | CI | ND | 0.13 |
| KI | VA | HI | ND | 0.10 |
| HI | VA | CI | RD | 0.09 |
| HI | AA | KI | AD | 0.09 |
| CI | HG | KI | AD | 0.08 |
| CI | HG | KI | AD | 0.08 |
| HI | AA | CI | AD | 0.05 |
| CI | VA | CI | RD | 0.01 |
| CI | MG | KI | AD | 0.00 |
| CI | VA | KI | AD | 0.00 |
| CI | QA | CI | AD | 0.00 |
| CI | QA | CI | AD | 0.00 |

FIGURE 4I

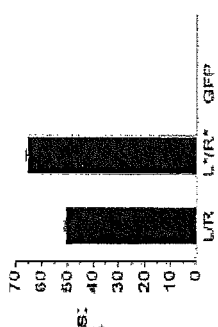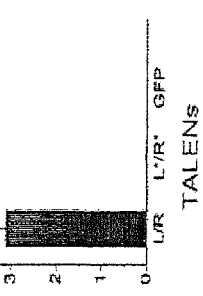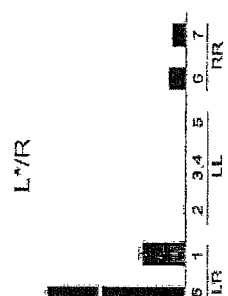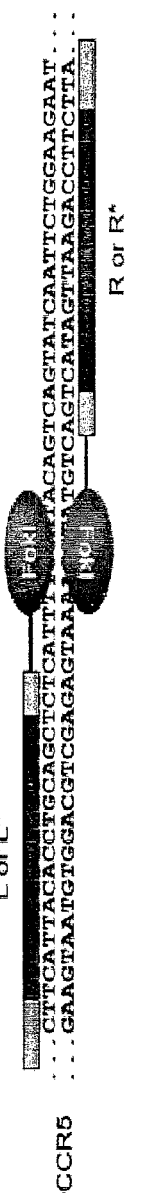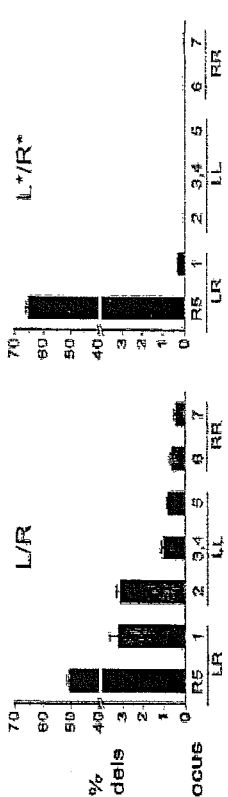
FIG 5A
FIG 5B
FIG 5C
FIG 5D

| TALEN ID | RVD Code | | | | % Gene Modification | RVDs used for base recognition (red highlights differences from TALEN L) | | | | | | | | | | | | | | | |
|---|---|---|---|---|---|---|---|---|---|---|---|---|---|---|---|---|---|---|---|---|---|
| | A | C | G | T | (37C) | T | C | A | T | T | A | C | A | C | C | T | G | C | A | G | C | T |
| TALEN L | NI | HD | NN | NG | 29.7 +/- 5.9 | NG | HD | NI | NG | NG | NI | HD | NI | HD | HD | NG | NN | HD | NI | NN | HD | NG |
| 101860 | HI | ND | KN | SG | 12.4 +/- 1.7 | SG | ND | HI | SG | SG | HI | ND | HI | ND | ND | SG | KN | ND | HI | KN | ND | SG |
| 101865 | HI | ND | KN | QG | 10.5 +/- 1.9 | QG | ND | HI | QG | QG | HI | ND | HI | ND | ND | QG | KN | ND | HI | KN | ND | QG |
| 101866 | HI | ND | KN | KG | 19.8 +/- 2.2 | KG | ND | HI | KG | KG | HI | ND | HI | ND | ND | KG | KN | ND | HI | KN | ND | KG |
| 101869 | HI | ND | KN | HG | 20.7 +/- 2.3 | HG | ND | HI | HG | HG | HI | ND | HI | ND | ND | HG | KN | ND | HI | KN | ND | HG |
| 101870 | HI | ND | KN | RG | 13.4 +/- 1.6 | RG | ND | HI | RG | RG | HI | ND | HI | ND | ND | RG | KN | ND | HI | KN | ND | RG |

ENGINEERED TRANSCRIPTION ACTIVATOR LIKE EFFECTOR (TALE) PROTEINS

CROSS-REFERENCE TO RELATED APPLICATIONS

The present application claims the benefit of U.S. Provisional Application No. 61/983,760, filed Apr. 24, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 27, 2015, is named 83250120_SL.txt and is 43,366 bytes in size.

TECHNICAL FIELD

The present disclosure is in the field of genome engineering, particularly targeted modification of the genome of a cell.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 8,623,618; 8,034,598; 8,586,526; 6,534,261; 6,599, 692; 6,503,717; 6,689,558; 7,067,317; 7,262,054; 7,888, 121; 7,972,854; 7,914,796; 7,951,925; 8,110,379; 8,409, 861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705, the disclosures of which are incorporated by reference in their entireties for all purposes.

These methods often involve the use of engineered cleavage systems to induce a double strand break (DSB) or a nick in a target DNA sequence such that repair of the break by an error prone process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. Clinical trials using cells modified using engineered nucleases have demonstrated therapeutic utility (see, e.g. Tebas et al (2014) New Eng J Med 370(10):901). Targeted cleavage using one of the above mentioned nuclease systems can be exploited to insert a nucleic acid into a specific target location using either HDR or NHEJ-mediated processes.

In particular, transcription activator-like effector (TALE) proteins have gained broad appeal as a platform for targeted DNA recognition due in large measure to their simple, code-like rules for design. See, e.g., U.S. Pat. Nos. 8,586, 526; 8,697,853; 8,685,737; 8,586,363; 8,470,973; 8,450, 471; 8,440,432; 8,440,431; 8,420,782 and U.S. Patent Publication No. 20130196373. These design rules relate the DNA base specified by a single TALE repeat to the identity of residues at two key positions (repeat variable diresidue residues or "RVD"), and allow for the design for new sequence targets via simple modular shuffling of these units. When bound to DNA, TALE proteins identify base sequences via contacts from a central array of TALE repeat units with each unit specifying one base. Moscou et al. (2009) Science 326:1501 ; Boch et al. (2009) Science 326:1509-1512 (2009); Deng et al. (2012) Science 335:720-723 ; Mak et al. (2012) Science 335:716-719. Repeats exhibit little diversity except at their RVD (positions 12 and 13) that recognizes the targeted base. Critically, the base preference of a TALE repeat is substantially determined by the identity of its resident RVD. Natural TALEs typically employ just four RVD sequences—NI, HD, NG, or NN—to recognize target bases of A, C, T or G/A, respectively, which four RVDs are known as canonical RVDs.

However, a key limitation of these rules is that their very simplicity precludes options for enhancing activity and/or specificity. For instance, as created using the natural code, TALENs can specify unintended bases in their binding sites and, in addition, also cleave non-targeted cellular sequence. See, e.g., Miller et al. (2011) Nat Biotechnol 29:143-148 ; Hockemeyer et al. (2011) Nat Biotechnol 29:731-734 ; Tesson et al. (2011) Nat Biotechnol 29:95-696; Mali et al. (2013) Nat Biotechnol 31(9): doi:10.1038/nbt.2675. Juillerat et al. (2014) Nucleic Acids Res (2014); Guilinger et al. (2014) Nat Methods 11(4):429-35 ; Osborn et al.(2013) Mol Ther 21, 1151-1159 (2013).

Thus, there remains a need for additional TALE protein compositions and methods, particularly for TALEs that exhibit enhanced specificity and/or activity.

SUMMARY

The present invention describes TALE compositions and methods for use in gene therapy and genome engineering. Specifically, the methods and compositions described relate to TALE proteins with RVDs that show enhanced activity and/or specificity as compared to previously-described TALEs using exclusively canonical RVDs, for example, by substantially reducing off-target genome cleavage. By providing novel RVDs and novel strategies for design of engineered TALEs, the present disclosure establishes options for developing novel TALEs with broader application across medicine and biotechnology.

In one aspect, described herein is an isolated, non-naturally occurring TALE DNA-binding protein comprising a plurality of TALE-repeat units, each TALE-repeat unit comprising a repeat variable di-residue region (RVD), and wherein (i) at least one RVD comprises EG or EP; and/or (ii) the RVD in the first repeat recognizes adenine (A); and/or (iii) the TALE DNA-binding protein recognizes a target site that does not comprise a 3' adenine (A); and/or (iv) the TALE DNA-binding protein recognizes a target site comprising 2 or fewer consecutive thymines (Ts); and/or (v) the TALE DNA-binding protein recognizes a target site that does not contain 5'-GG-3' or 5'-GC-3' dinucleotides. In certain embodiments, at least one RVD is non-canonical. In other embodiments, all the RVDs are non-canonical. In still further embodiments, at least 2, 3, 4 or 5 features as set forth in (i) to (v) are present in the TALE DNA-binding protein. Also disclosed herein is a fusion protein comprising the TALE DNA-binding protein as described herein and a functional domain (e.g., a transcriptional activator, a transcriptional repressor, methyltransferase and/or a nuclease cleavage domain such as a FokI cleavage domain).

In another aspect, described herein is a polynucleotide encoding any of the TALE DNA-binding proteins and/or fusion proteins as described herein. Host cells, for example, isolated host cells comprising any of TALE-DNA binding proteins, fusion proteins and/or polynucleotides described herein also provided. The host cell may be a eukaryotic cell (e.g., mammalian, for example, stem cell), fungal (e.g. yeast) or plant cell.

In yet another aspect, provided herein is an isolated cell comprising a target site and a non-naturally occurring TALE DNA-binding protein that binds to the target site, the TALE DNA-binding protein comprising a plurality of TALE-repeat units, each TALE-repeat unit comprising a repeat variable di-residue region (RVD), and wherein (i) the RVD in the first repeat recognizes adenine (A); (ii) the target site that does not comprise a 3' adenine (A); (iii) the target site comprises 2 or fewer consecutive thymines (Ts); and/or (iv) the target site does not contain 5'-GG-3' or 5'-GC-3' dinucleotides. In certain embodiments, the TALE DNA-binding protein further comprises a functional domain (e.g., a transcriptional activator, a transcriptional repressor, methyltransferase and/or a nuclease cleavage domain such as a FokI cleavage domain). In any of the cells described herein, the TALE DNA-binding domain and/or fusion protein may be introduced into the cell as a polynucleotide encoding the TALE DNA-binding domain and/or a fusion protein comprising the TALE DNA-binding domain. In certain embodiments, the cell is a eukaryotic cell (e.g., fungal, mammalian (e.g., stem cell) or plant cell). In another aspect, described herein is a method of making a TALE DNA-binding protein with enhanced binding specificity, the method comprising: generating a sequence encoding any of the TALE DNA-binding proteins as described herein that bind to a target DNA sequence, wherein the TALE DNA-binding protein and the target DNA sequence comprise one or more of these features: (i) the RVD in the first repeat recognizes adenine (A); and (ii) the target site does not comprise a 3' adenine (A); and (iii) the target site comprises 2 or fewer consecutive thymines (Ts); and (iv) the target site does not contain 5'-GG-3' or 5'-GC-3' dinucleotides, wherein the TALE DNA binding protein exhibits enhanced specificity or activity as compared to a second TALE DNA binding protein that binds to a second target DNA sequence, wherein the second TALE DNA binding protein and the second target DNA sequence do not comprise the features. The first and second target sites may be the same target site, overlapping target sites, different target sites in the same gene or target sites in different genes. In certain embodiments, at least 2, 3, or 4 features as set forth in (i) to (iv) are present in the TALE DNA-binding protein that exhibits enhanced specificity or activity.

In yet another aspect, described herein is a method of making a cell comprising a first TALE DNA-binding protein that binds to a first target DNA with enhanced binding activity or specificity for the target site, the method comprising: providing a cell, and contacting the cell with a first TALE DNA-binding protein comprising a plurality of TALE-repeat units, each TALE-repeat unit comprising a repeat variable di-residue region (RVD) that binds to a first target DNA wherein the first TALE DNA binding protein and the first target sequence comprise the following features: (i) the RVD in the first repeat recognizes adenine (A); and (ii) the target site does not comprise a 3' adenine (A); and (iii) the target site comprises 2 or fewer consecutive thymines (Ts); and (iv) the target site does not contain 5'-GG-3' or 5'-GC-3' dinucleotides, wherein said first TALE DNA binding protein exhibits enhanced specificity or activity for the first target DNA as compared to a second TALE DNA binding protein that binds to a second target DNA wherein the second TALE DNA binding protein and the second target DNA do not comprise the features.

In yet another aspect, described herein is a method of modulating expression of an endogenous gene in a cell, the method comprising: introducing into the cell a fusion protein as described herein, wherein the TALE DNA-binding protein binds to a target site in the endogenous gene and further wherein expression of the endogenous gene is modulated by the fusion protein. The modulation may be gene activation, gene repression and/or gene inactivation. In certain embodiments, the endogenous gene is inactivated by cleavage of gene (e.g., where the TALE is fused to a nuclease cleavage domain).

In a still further aspect, provided herein is a method of modulating expression of an endogenous gene in a cell, the method comprising: providing a cell as described herein, wherein the target site is in the endogenous gene and further wherein expression of the endogenous gene is modulated. The modulation may be gene activation, gene repression and/or gene inactivation. In certain embodiments, the endogenous gene is inactivated by cleavage of gene (e.g., where the TALE is fused to a nuclease cleavage domain).

In a still further aspect, described herein is a method of modifying a region of interest in the genome of a cell, the method comprising: introducing into the cell at least one fusion protein as described herein, wherein the TALE DNA-binding protein binds to a target site in the genome of the cell and the fusion protein cleaves the genome in the region of interest. The modifying may comprise introducing an insertion or deletion (indel) in the region of interest and/or introducing an exogenous nucleic acid into the region of interest. The cell may be a eukaryotic cell selected from the selected from the group consisting of a plant cell, an animal cell, a fish cell and a yeast cell.

In a still further aspect, described herein is a method of modifying a region of interest in the genome of a cell, the method comprising: providing a cell as described herein (e.g., a cell comprising a fusion protein comprising a TALE-DNA binding domain and a nuclease cleavage domain), wherein the target site is in the genome of the cell the genome is cleaved in the region of interest. The modifying may comprise introducing a deletion in the region of interest and/or introducing an exogenous nucleic acid into the region of interest. The cell may be a eukaryotic cell selected from the selected from the group consisting of a plant cell, an animal cell, a fish cell and a yeast cell.

In any of the compositions (e.g., cells) and/or methods described herein, the TALE-DNA binding proteins and/or fusion proteins may be introduced as polynucleotides (e.g. DNA or RNA). In some aspects, the mRNA may be chemically modified (See e.g. Kormann et al, (2011) Nature Biotechnology 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012-0195936).

A kit comprising any of the TALE DNA-binding proteins, fusion proteins, polynucleotides and/or cells as described herein is also provided.

In one aspect, described herein are polypeptides comprising a cleavage competent TALEN dimer, each TALEN comprising a plurality of TALE repeat units (e.g., 3, 4, 5, 6, 7, 8, 9, 10, 11, 12, 13, 14, 15, 16, 17, 18, 19, 20 or more repeat unit(s)), in which three of more of the repeat units comprise RVDs that differ from each other and from the canonical RVD set (NN, NI, HD, NG). In certain embodiments, the TALE protein does not comprise any canonical RVDs. In still further embodiments, the TALE proteins as described herein exhibit enhanced affinity and/or specificity as compared to a TALE protein comprising exclusively canonical RVDs. In certain embodiments, the TALE protein comprises a non-canonical RVD of VG, IG, MG, EG, EP, VA or QG, which specify thymine (T). In other embodiments, the TALE protein comprises a non-canonical RVD of GN, VN, LN, DN, QN, EN, RH, AN or FN which specify guanine (G). In other embodiments, the TALE protein comprises a non-canonical RVD of CI or KI that specifies adenine (A). In other embodiments, the TALE protein comprises a non-canonical RVD of RD, KD or AD, which specifies cytosine (C). The polypeptides described herein may also include a C-cap sequence (polypeptide), for example a C-cap sequence of less than approximately 250 amino acids (C+230 C-cap; from residue C−20 to residue C+230) and/or an N-cap sequence (polypeptide), for example an N-cap sequence of less than approximately 140 amino acids (e.g., N+1 to N+136). The TALE repeat unit may be a wild-type domain isolated from *Xanthomonas, Ralstonia* or other organism and altered to comprise only non-canonical RVDs.

In another aspect, provided herein are TALEs that target DNA sequences that enable optimal recognition. In one embodiment, the TALE protein targets a sequence in which the first repeat recognizes adenine (A). In another embodiment, the TALE protein target a sequence in which the C-terminal half repeat recognizes a base other than adenine (A). In another embodiment, the TALE protein targets a sequence that does not contain the dinucleotide: guanine-guanine (GG). In another embodiment, the TALE protein targets a sequence that does not contain the dinucleotide: guanine-cytosine (GC). In another embodiment, the TALE protein targets a sequence that does not contain the trinucleotide thymine-thymine-thymine (TTT).

In another aspect, provided herein are fusion proteins comprising any of the TALE proteins described herein operatively linked to one or more heterologous polypeptide domains, for example functional (regulatory or cleavage) domains. Libraries comprising modules of TALE repeats are provided as are optional structured or flexible linkers for connecting the engineered TALE repeats to the functional protein domain of interest. The functional protein domain (e.g., transcriptional activator, repressor, or nuclease) may be positioned at the C- or N-terminus of the fusion protein. In certain embodiments, the fusion protein comprises an inactive cleavage domain, which when dimerizes with an active cleavage domain produces a single-stranded break (nick) in a double-stranded target. Methods of making fusion proteins as described herein are also provided.

Polynucleotides (e.g., DNA, RNA such as mRNA) encoding the proteins (e.g., TALEs and fusion proteins comprising these TALEs) as described herein are also provided, as are pharmaceutical compositions comprising the proteins and/or polynucleotides. In addition, the invention includes host cells, cell lines and transgenic organisms (e.g., plants, fungi, animals) comprising these proteins/polynucleotides and/or modified by these proteins (e.g., genomic modification that is passed onto the progeny).

In another aspect, described herein are compositions comprising one or more of the TALE-fusion proteins and/or polynucleotides described herein. In certain embodiments, the composition comprises one or more TALE-fusion proteins in combination with a pharmaceutically acceptable excipient. In some embodiments, the composition comprises a polynucleotide (e.g., DNA and/or RNA) encoding the TALE fusion protein and a pharmaceutically acceptable excipient. In some aspects, the mRNA may be chemically modified (See e.g. Kormann et al, (2011) Nature Biotechnology 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012-0195936). In certain embodiments, the compositions further comprise a nucleic acid donor molecule.

In another aspect, described herein is a TALE-fusion protein expression vector comprising a polynucleotide, encoding one or more enhanced TALE-fusion proteins described herein, operably linked to a promoter (e.g., constitutive, inducible, tissue-specific or the like).

In another aspect, described herein is a cell comprising a protein and/or polynucleotide as described herein; and/or a genetically modified cell produced using a protein and/or polynucleotide as described herein, including progeny or descendants of such cells. The cell may be a prokaryotic cell or a eukaryotic cell. Exemplary cells and cell lines include animal cells (e.g., mammalian, including human, cells such as stem cells), plant cells, bacterial cells, protozoan cells, fish cells, or fungal cells. In another embodiment, the cell is a mammalian cell. In any of the methods and compositions (e.g., cells) described herein, the cell can be any eukaryotic cells, for example a plant cell or a mammalian cell or cell line, including COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells (e.g., CD34+), neuronal stem cells and mesenchymal stem cells. In certain embodiments, the cell is a genetically modified animal or plant cell that is modified using a TALEN as described herein. In any of the compositions or methods described herein, the plant cell can comprise a monocotyledonous or dicotyledonous plant cell. In certain embodiments, the plant cell is a crop plant, for example, tomato (or other fruit crop), potato, maize, soy, alfalfa, etc. In certain embodiments, provided herein is a seed and/or a fruit from a plant comprising the genetically modified plant cell that is obtained as described herein.

In some embodiments, the transgenic cell, plant and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In some aspects, stem cells or embryo cells are used in the development of transgenic animals, including for example animals with TALE-mediated genomic modifications that are integrated into the germline such that the mutations are heritable. In further aspects, these transgenic animals are used for research purposes, i.e. mice, rats, rabbits; while in other aspects, the transgenic animals are livestock animals, i.e. cows, chickens, pigs, sheep etc. In still further aspects, the transgenic animals are those used for therapeutic purposes, i.e. goats, cows, chickens, pigs; and in other aspects, the transgenic animals are companion animals, i.e. cats, dogs, horses, birds or fish.

In yet another aspect, a method of designing a TALE protein is provided, the method comprising selecting a target site of interest, generating a TALE protein that binds to the target site, the TALE protein comprising a plurality of TALE repeats in which three or more repeat units comprise RVDs that differ from each other and from the canonical RVD set (NN, NI, HD, NG). In certain embodiments, the TALE protein does not comprise any canonical RVDs. In further embodiments, the TALE proteins as described herein exhibit enhanced affinity and/or specificity as compared to a TALE protein comprising exclusively canonical RVDs. In certain embodiments, the TALE protein comprises a non-canonical RVD of VG, IG, MG, EG, EP, EP, VA, or QG which specify thymine (T). In other embodiments, the TALE protein comprises a non-canonical RVD of GN, VN, LN, DN, QN, EN, RH, AN or FN which specify guanine (G). In other embodiments, the TALE protein comprises a non-canonical RVD of CI or KI that specifies adenine (A). In other embodiments, the TALE protein comprises a non-canonical RVD of RD, KD or AD, which specifies cytosine (C). In certain embodiments, all the TALE repeat units comprise a non-canonical RVD. In other embodiments, one or more of the TALE repeat units in the TALE protein comprise a non-canonical RVD. In further embodiments, two or more of the TALE repeat units in the TALE protein comprise a non-canonical RVD. In still further embodiments, three or more of the TALE repeat units in the TALE protein comprise a non-canonical RVD. In further embodiments, the first (N-terminal) repeat of the TALE protein recognizes adenine (A). In still further embodiments, the target site bound by the TALE does not comprise a 3' adenine (A) and/or comprises 2 or fewer consecutive thymines (Ts) (i.e., the target site does not include any runs of 3 or more thymines) and/or does not contain 5'-GG-3' or 5'-GC-3' dinucleotides. In certain embodiments, the TALE designed as described herein exhibit enhanced specificity.

In another aspect, described are methods of increasing the specificity and/or activity of a TALEN, the method comprising designing a TALE protein as described herein, and generating a TALEN comprising the designed TALE, such that the TALEN exhibits increased specificity and/or activity as compared to a TALE comprising canonical RVDs.

In another aspect, described herein is a method for cleaving one or more genes of interest in a cell, the method comprising: (a) introducing, into the cell, one or more one or more TALEN protein(s) as described herein (or polynucleotides encoding the TALENs) that bind to a target site in the one or more genes under conditions such that the TALEN protein(s) is (are) expressed and the one or more genes are cleaved. In embodiments in which two or more TALEN proteins are introduced, one, some or all can be introduced as polynucleotides or as polypeptides. In some aspects, said gene cleavage results in the functional disruption of the targeted gene. Cleavage of the targeted DNA may be followed by NHEJ wherein small insertions and/or deletions (indels) are inserted at the site of cleavage. These indels then cause functional disruption through introduction of non-specific mutations at the cleavage location.

In yet another aspect, described herein is a method for introducing an exogenous sequence into the genome of a cell, the method comprising the steps of: (a) introducing, into the cell, one or more TALEN protein(s) as described herein (or polynucleotides encoding the TALEN protein(s)) that bind to a target site in a target gene under conditions such that the TALEN protein(s) is (are) expressed and the one or more target sites within the genes are cleaved; and (b) contacting the cell with an exogenous sequence; such that cleavage of the DNA target site(s) stimulates integration of the exogenous sequence into the genome by homologous recombination. In certain embodiments, the exogenous sequence is integrated physically into the genome. In other embodiments, the exogenous sequence is integrated into the genome by copying of the exogenous sequence into the host cell genome via specialized nucleic acid replication processes associated with homology-directed repair (HDR) of the double strand break. In yet other embodiments, integration into the genome occurs through non-homology dependent targeted integration (e.g. "end-capture").

A kit, comprising the TALEs of the invention, is also provided. The kit may comprise DNA encoding the nucleases comprising TALENs as described herein(e.g. RNA molecules and/or TALEN-encoding genes contained in a suitable expression vector), or aliquots of the nuclease proteins, donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIGS. 1A through 1E show the design and specificities of TALEs generated using the natural TALE code. FIG. 1A is a sketch of a natural TALE highlighting the central repeat array that mediates DNA recognition (dark gray boxes). A typical repeat sequence (SEQ ID NO:1) is provided above in single-letter amino acid code, with a square enclosing the RVD that determines base preference (positions 12 and 13). Flanking protein segments are shaded in light gray. "N" denotes the amino terminus. FIG. 1B depicts RVD:base correspondences that constitute the natural TALE code. FIG. 1C is a graphical depiction of a SELEX-derived base frequency matrix for a synthetic TALE designed using the natural RVD code. At each matrix position, the frequency of the intended target base is projected above the x-axis, whereas the remaining base frequencies are plotted below the x-axis. Matrix positions are arranged in 5' to 3' order (left to right) with corresponding RVDs listed above (14 total). The four examples of the "NN" RVD (underlined) manifest a range of base preferences while "HD" unexpectedly specifies adenine within the first repeat. The N-terminal flanking segment specifies the 5' thymine base. FIG. 1D shows average base preference for each natural code RVD when used within either the amino terminal repeat (left panel) or other repeat positions (right panel) from a large scale SELEX study of 76 engineered TALES. HD, NN and NG exhibit substantially enhanced binding to adenine in the context of the amino terminal repeat (***: $p<10-6$; *: $p<0.002$). FIG. 1E shows average base preferences for NN when flanked by each possible canonical RVD, showing that neighbor identity affects selectivity for guanine vs. adenine. A double asterisk (**) indicates a statistically significant difference in guanine preference (p<0.0002) for the indicated context vs. each other context in the panel. Values in (d) and (e) are derived from the large scale SELEX study of 76 TALEs. All p values were Mann-Whitney test corrected for false discovery rate.

FIGS. 2A through 2G show a comprehensive survey of RVD-DNA binding properties. FIG. 2A (top) shows a diagram of proteins generated for this study. A 10-repeat host TALE was diversified into 400 proteins bearing each possible RVD in its fifth repeat (shaded box; "XX" denotes varied RVD composition). The remaining nine repeats were held constant (lighter gray boxes; two-letter codes indicate each RVD). The C-terminal repeat was truncated as found in all TALEs studied and the bottom panel shows targets (SEQ ID NO:2) used for the study. See, also, U.S. Pat. No. 8,586,526. Each TALE was assayed for binding to four variants of the host target in which the base contacted by the fifth repeat (underscore) was "A", "C", "G" or "T". FIG. 2B shows exemplary assay data for the four natural code RVDs. Four proteins, each bearing the indicated natural code RVD in its fifth repeat, were screened by ELISA for binding to the "A", "C", "G" or "T" variants of the host target (indicated by the shaded letters). ELISA signals were normalized to the average value obtained for the interaction of each code RVD with its preferred base (i.e. values on the diagonal, highlighted by boxes). FIG. 2C shows a graphical depiction of binding data. The size of each circular plot is proportional to the ELISA signal of the indicated RVD with its preferred base (i.e. affinity), while the areas of each shaded wedge indicate relative binding activities for each base target (i.e. specificity). Arrows relate each plot to the row of four ELISA values used to construct it. FIG. 2D is a graphical summary of binding data for all RVDs and targets. RVDs are identified by residue type at position 12 (at left) and 13 (at top), with residues listed in order of increasing volume. ELISA data for each RVD are summarized by a circular plot at the corresponding location in the 20×20 matrix. Boxes highlight data corresponding to the natural code RVDs (NG, NI, NN, and HD). FIGS. 2E, 2F and 2G shows normalized ELISA scores for all 1600 pairings of RVD and base type. Highlighted data entries denote canonical RVDs, with boxes indicating RVD:base correspondences specified by the natural TALE code.

FIGS. 3A and 3B depict the improvement of TALE properties via substitution of key RVDs. FIG. 3A depicts SELEX-derived base frequency matrix and gene modification activity of an all-canonical TALEN targeted to the human PitX3 locus. The base frequency matrix is presented graphically as described in FIG. 1C, with each RVD listed above its corresponding matrix column. "Activity" indicates % indels induced upon delivery to K562 cells with its partner TALEN. FIG. 3B shows SELEX profiles and gene modification activities of variant TALENs in which key repeats bear non-canonical RVDs (HN, RH, and NK). Each variant shown manifests improved specificity and activity.

FIGS. 4A through 4I depict assembly and gene modification activity of TALENs that use an expanded set of RVDs. FIG. 4A depicts the first stage of assembly in which four TALE tetramer libraries were created via combinatorial gene assembly, each targeting a distinct quartet base sequence from the TALEN L binding site (shown at top with quartets boxed, SEQ ID NO:3). RVD mixtures encoded during gene synthesis are listed above each tetramer library repeat. A panel of constructs was then screened via ELISA to identify binding-validated tetramers (three shown for each quartet). The tetramer libraries were assembled in the context of longer host TALE proteins in order to provide sufficient affinity for ELISA screens. FIG. 4B shows the second stage of assembly in which DNA segments encoding binding-validated tetramers were randomly linked with each other and with a degenerate 17th repeat (encoding HG or KG) via combinatorial gene assembly. The resulting 17-repeat library was cloned into a TALEN vector, and 72 randomly chosen constructs, along with 16 discretely assembled TALENs, were screened for gene modification activity when introduced into K562 cells in combination with the partner TALEN R. These studies yielded TALEN L* as the most active variant (at bottom, boxes highlight component tetramers). FIG. 4C shows TALEN R*, which was generated via a similar two-stage process (whose binding site is shown in SEQ ID NO:4). FIG. 4D shows context-dependent behavior of the same RVDs in two different contexts are shown in each pair of grids. The score is the average normalized DNA binding score for all tetramers with the indicated RVD in position to contact the underlined base in the 4 base pair subsite. In this case, binding values were normalized to average DNA binding value for all clones in the library. SE indicates the standard error of the score. N indicates the number of observations. Each grid is sorted by score. RVDs that show large differences in score between the two contexts are highlighted in gray. FIG. 4E shows gene modification activity of the new TALENs. The L*/R* dimer or its canonical parent (L/R) were delivered to K562 cells followed by assessment of gene modification activity via the Surveyor assay (left panel) and by deep sequencing (right panel). FIGS. 4F to 4I show normalized ELISA scores of tetramer units screened during development of noncanonical TALENs. In each panel, the target DNA quartet is provided at top, with RVD designs and ELISA scores listed beneath and ordered by activity.

FIGS. 5A through 5E show reduced modification of off-target loci in cells exposed to RVD-diversified TALENs. FIG. 5A is a sketch of the TALENs used for this study in complex with the intended cleavage target in the CCR5 gene (SEQ ID NOs:5 and 6). The L and R TALENs recognize DNA using canonical RVDs, while L* and R* use a more diverse set of alternative RVDs (FIGS. 5B, C). CCR5 modification levels induced by L/R, L*/R*, or a GFP negative control are plotted at right. FIG. 5B is a sketch of TALENs in complex with the two most active off-target loci examined in this study (OT1 and OT2, SEQ ID NOs:7-10). Lower case letters indicate bases that diverge from the intended target sequence. Note that OT2 is a cleavage target for a homodimer of "left" TALENs (i.e. L/L or L*/L*). Modification levels observed at each locus are plotted at right. FIG. 5C shows modification levels at seven of the more active off-target sites (OT1-OT7; labeled 1-7) and the intended CCR5 target (R5) in cells exposed to L/R and L*/R*. "LR", "LL" and "RR" indicate the hetero- or homodimer TALEN species predicted to cleave each target. Note that data for OT3 and OT4 were merged since these loci differ by a single SNP and frequently cannot be distinguished after acquisition of an indel. FIG. 5D shows modification levels at OT1-OT7 in cells exposed to the mixed dimers L/R* and L*/R. In all panels error bars indicate the standard deviation of three determinations of modification level via deep sequencing of genomic DNA pooled from 12 replicate transfections. FIG. 5E shows exemplary SELEX results for the indicated TALENs.

FIG. 6A is a graphical representation of SELEX-derived base frequency matrices for 10 TALEs characterized in large scale SELEX studies. At each matrix position, the frequency of the intended target base is projected above the x-axis, whereas the remaining base frequencies are plotted below the x-axis. Matrix positions are arranged in 5' to 3' order (left to right) with corresponding RVDs listed above. As shown, base preferences for each RVD can vary over a wide quantitative range. Numerical identifiers are shown adjacent to each plot. FIG. 6B shows average base preference for three of the natural code RVDs when deployed within the carboxy terminal repeat of an engineered TALE. NI and HD exhibit substantially reduced average preference for their target bases in this context as compared with non-terminal repeats (compare with FIG. 1D: *: $p<10^{-6}$; : $p<10^{-4}$). NN was not tested in the carboxy-terminal repeat in these studies. FIG. 6C shows average base preference of NG observed in successively longer arrays of this RVD. Thymine is highly specified when neither flanking RVD is NG (left bar; 131 examples in this study), or when NG is deployed in two adjacent repeats (second panel from left; 27 examples of an NG-NG pair). However average thymine preference is substantially reduced for NG RVDs that are centrally located within longer runs of this RVD (three rightmost panels; 7 examples of $(NG)_3$ and 2 examples each of $(NG)_4$ and $(NG)_5$; *: $p<10^{-4}$ for indicated context compared with the left-most bar). Plotted values are derived from the large scale SELEX study of 76 synthetic TALEs, and were calculated using the base preferences of every non-terminal repeat from that study. All p values are Mann-Whitney test corrected for false discovery rate.

FIGS. 7A through 7C show RVD usage and gene modification activity of TALEN variants that employ progressively higher fractions of alternative RVDs for DNA recognition without allowing different RVD choices for different contexts. FIG. 7A shows variants of TALEN "L" that were generated using the indicated RVD sets (columns "A", "C", "G" and "T"; RVDs that differ from the natural code are underlined). Constructs expressing each protein were introduced into K562 cells in combination with the partner TALEN "R" (the "R557" protein from Miller et al. (ibid. Cells were harvested after three days of culture at 37° C. or with an intervening 30° C. cold shock, and gene modification levels were determined using the Surveyor assay. FIG. 7B shows variants of TALEN "L" that were generated using the indicated RVD sets that include a higher fraction of noncanonical RVDs (columns "A", "C", "G" and "T"; RVDs that differ from the natural code are underlined). Constructs expressing each protein were introduced into K562 cells in combination with the partner TALEN "R" (the "R557" protein from and cellular studies were replicated either 6 times (TALEN L) or 3 times (remaining variants) without a cold shock arm. Gene modification levels were quantified via high throughput sequencing with average values and standard deviations shown. FIG. 7C shows results with TALENs that use exclusively RVDs that differ from the natural code. Note that repeats targeting guanine with a new RVD bear one additional residue substitution (N11S) relative to the parent "NN" repeat. FIGS. 7A-7C disclose SEQ ID NO: 59.

FIG. 8A is a sketch of the TALEN pairs examined in this study (L+17/R2+17 and L*+17/R2+17) bound to their intended target in the CCR5 locus. On-target activity for L+17/R2+17, L*+17/R2+17, or eGFP is plotted at right. Human K562 cells were treated with 400 ng of each plasmid encoding the indicated constructs and subjected to a cold shock protocol (U.S. Pat. No. 8,772,008). Genomic DNA was harvested 3 days post transfection and genomic DNA from 12 separate replicate transfections was pooled prior to measuring indels by Illumina MiSeq sequencing. Error bars indicate standard deviation of two technical replicates of the same genomic DNA pools. FIG. 8B is a diagram showing homodimers of L+17 or L*+17 bound to the off-target site "+17_OT1". Activity of L+17/R2+17, L*+17/R2+17, or eGFP at this off-target site is plotted at right. FIGS. 8A-8B disclose SEQ ID NOS 60-63, respectively, in order of appearance.

FIGS. 9A and 9B show on- and off-target activity of the TALEN dimers L/R and L*/R*. FIG. 9A shows analysis of 20 off-target loci that had been previously validated as detectably modified by L/R, in either Miller et al. (2015) Nature Methods Mar 23. doi: 10.1038/nmeth.3330 (OT1-9, OT11-13;) or Guilinger et al., infra (off C–5, –15, –16, –36, –38, –49, –69, and –76). Experimental conditions, data processing, and table entries are as described in FIG. 8. FIG. 9B shows on- and off-target activity of the L/R and L*/R* TALEN dimers further modified to include the "Q3" mutations (modification denoted by "_Q3" appendage). As shown in the rightmost columns (L*$_{13}$Q3/R*_Q3), use of the novel RVDs in combination with the Q3 mutations yields the lowest aggregate levels of off-target cleavage.

DETAILED DESCRIPTION

Figure 4E:
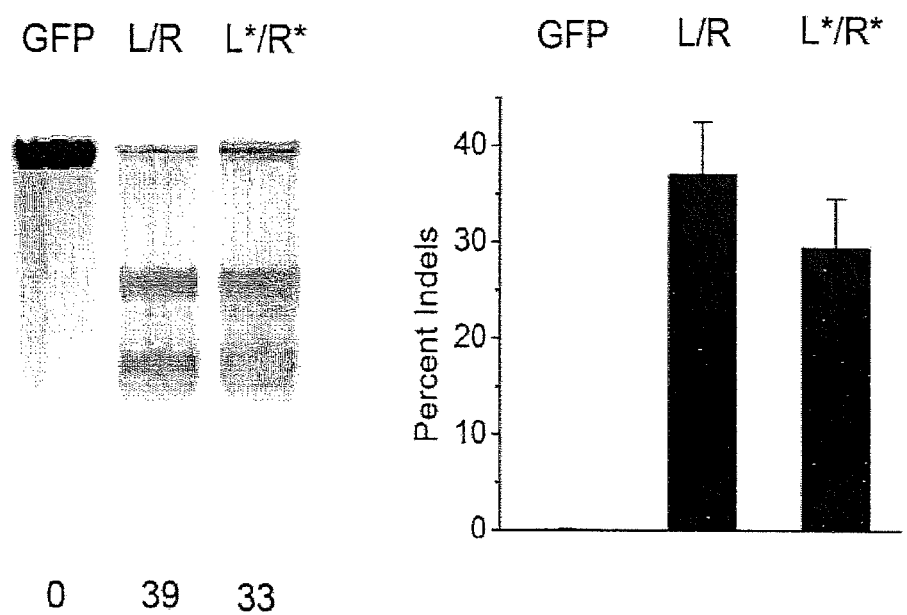

The present application describes TALE DNA-binding polypeptides, fusion proteins comprising these TALE DNA-binding polypeptides and methods of using these fusion proteins, including enhancing one or more of the functions (e.g., DNA binding activity, nuclease cleavage activity and/or DNA binding specificity) of these proteins. In some embodiments, the TALE DNA-binding polypeptides (and/or polynucleotide encoding same) comprise non-canonical RVDs (e.g., EG or EP RVDs to recognize thymine (T)). In other embodiments, described herein is an isolated, non-naturally occurring TALE DNA-binding protein (and/or polynucleotide encoding same) comprising a plurality of TALE-repeat units, each TALE-repeat unit comprising a repeat variable di-residue region (RVD), and wherein (i) at least one RVD comprises EG or EP; and/or (ii) the RVD in the first repeat recognizes adenine (A); and/or (iii) the TALE DNA-binding protein recognizes a target site that does not comprise a 3' adenine (A); and/or (iv) the TALE DNA-binding protein recognizes a target site comprising 2 or fewer consecutive thymines (Ts); and/or (v) the TALE DNA-binding protein recognizes a target site that does not contain 5'-GG-3' or 5'-GC-3' dinucleotides. In some embodiments, all RVDs are canonical. In certain embodiments, at least one RVD is non-canonical. In other embodiments, all the RVDs are non-canonical. In still further embodiments, at least 2, 3, 4 or 5 features as set forth in (i) to (v) are present in the TALE DNA-binding protein. Also provided herein is an isolated cell comprising a target site and a non-naturally occurring TALE DNA-binding protein (and/or polynucleotide encoding same) that binds to the target site, the TALE DNA-binding protein comprising a plurality of TALE-repeat units, each TALE-repeat unit comprising a repeat variable di-residue region (RVD), and wherein (i) the RVD in the first repeat recognizes adenine (A); (ii) the target site that does not comprise a 3' adenine (A); (iii) the target site comprises 2 or fewer consecutive thymines (Ts); and/or (iv) the target site does not contain 5'-GG-3' or 5'-GC-3' dinucleotides. The TALE DNA-binding protein may further comprise a functional domain (e.g., a transcriptional activator, a transcriptional repressor, methyltransferase and/or a nuclease cleavage domain such as a FokI cleavage domain).

Thus, the invention provides TALE fusion proteins that bind with increased specificity and/or affinity (or both) to a target site relative to their canonical counterparts. These proteins, when fused to a nuclease cleavage domain, exhibit increased specificity and/or activity in comparison with TALE fusion proteins made using exclusively canonical RVDs.

In some embodiments, the invention comprises methods for increasing the specificity and/or activity of TALE-fusion proteins, for example TALE-nuclease fusion proteins (TALENs). Methods to enhance TALE specificity and/or activity contemplated by this invention include use of TALEs as described herein (e.g., lacking any NN RVDs). In addition, by using RVDs in favorable contexts, binding specificity and/or activity can be increased. This can be achieved, for example, by (i) choosing a target site that does not comprise 3 or more contiguous thymines (Ts), (ii) choosing a target site where the base recognized by the amino-terminal repeat is an adenine (A), (iii) choosing a target site where the C-terminal "half repeat" does not target an adenine, (iv) choosing a target site that does not contain the dinucleotide 5'-GG-3', or (v) choosing a target site that does not contain the dinucldotide 5'-GC-3' or any combination of (i)-(v) thereof The methods and compositions of the invention can be used to create a TALEN protein that acts as a "nickase" on the DNA, i.e., cleaves one strand of double-stranded DNA. In such "nicking" embodiments, one half of the nuclease dimer comprises a nuclease fusion partner that is inactive such that pairing of the inactive cleavage domain with another active domain results in a cleavage protein that is only able to "nick" the DNA by cleaving only one strand. See, e.g., U.S. Publication No. 20100047805. In some embodiments, two pairs of nickases are used to create dual DNA nicks on either strand of the target double-stranded DNA molecule. Use of the two nickase proteins enhances cleavage specificity at any chosen site, and also allows the user to design optimal overhangs on the DNA following cleavage.

The methods and compositions described herein allow for the development of TALENs and TALE TFs with increased specificity and/or activity for novel human and mammalian therapeutic applications, e.g., treatment of genetic diseases, cancer, fungal, protozoal, bacterial, and viral infection, ischemia, vascular disease, arthritis, immunological disorders, etc., as well as providing for functional genomics assays, and generating engineered cell lines for research and drug screening, and generate restriction enzymes to cleave DNA at any desired sites as a tool, and means for developing plants with altered phenotypes, including but not limited to, increased disease resistance, and altering fruit ripening characteristics, sugar and oil composition, yield, and color.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526 and U.S. Patent Publication No. 20130196373.

A "TALE-repeat domain" (also "repeat array") is a sequence that is involved in the binding of the TALE to its cognate target DNA sequence and that comprises one or more TALE "repeat units." A single "repeat unit" (also referred to as a "repeat") is typically 33-35 amino acids in length and exhibits at least some sequence homology with other TALE repeat sequences within a naturally occurring TALE protein. A TALE repeat unit as described herein is generally of the form $(X)^{1\ to\ 11}$-$(X^{RVD})_2$-$(X)_{20-22}$ (SEQ ID NO:11) where $X^{RVD}$ (positions 12 and 13, where "RVD" refers to the repeat divariable residues at these positions) exhibit hypervariability in naturally occurring TALE proteins. Altering the identity of the RVD of each repeat (amino acids at positions 12 and 13) can alter the preference for the identity of the DNA nucleotide (or pair of complementary nucleotides in double-stranded DNA) with which the repeat unit interacts. There are four "canonical" RVDs (positions 12 and 13): NI (for binding to A), HD (for binding to C), NN (for binding to G) or NG (for binding to T). A "non-canonical" RVD includes any diresidue sequence other than the canonical NI, HD, NN, or NG. An "atypical" RVD is an RVD sequence (positions 12 and 13) that occurs infrequently or never in nature, for example, in less than 5% of naturally occurring TALE proteins, preferably in less than 2% of naturally occurring TALE proteins and even more preferably less than 1% of naturally occurring TALE proteins. An atypical RVD can also be non-naturally occurring. See, e.g., U.S. Pat. No. 8,586,526 and U.S. Patent Publication No. 20130196373.

The terms "N-cap" polypeptide and "N-terminal sequence" are used to refer to an amino acid sequence (polypeptide) that flanks the N-terminal portion of the TALE repeat domain. The N-cap sequence can be of any length (including no amino acids), so long as the TALE-repeat domain(s) function to bind DNA. Thus, an N-cap sequence may be involved in supplying proper structural stabilization for the TALE repeat domain and/or nonspecific contacts with DNA. An N-cap sequence may be naturally occurring or non-naturally occurring, for example it may be derived from the N-terminal region of any full length TALE protein. The N-cap sequence is preferably a fragment (truncation) of a polypeptide found in full-length TALE proteins, for example any truncation of a N-terminal region flanking the TALE repeat domain in a naturally occurring TALE protein that is sufficient to support DNA-binding function of the TALE-repeat domain or provide support for TALE fusion protein activity. When each TALE-repeat unit comprises a typical RVD and/or when the C-cap comprises a full-length naturally occurring C-terminal region of a TALE protein, the N-cap sequence does not comprise a full-length N-terminal region of a naturally occurring TALE protein. Thus, as noted above, this sequence is not necessarily involved in DNA recognition, but may enhance efficient and specific function at endogenous target DNA or efficient activity of the TALE fusion protein. The portion of the N-cap sequence closest to the N-terminal portion of the TALE repeat domain may bear some homology to a TALE repeat unit and is referred to as the "R0 repeat." Typically, the preferred nucleotide to the position immediately 5' of the target site is thymidine (T). It may be that the R0 repeat portion of the N-cap prefers to interact with a T (or the A base-paired to the T in double-stranded DNA) adjacent to the target sequence specified by the TALE repeats. See, e.g., U.S. Pat. No. 8,586,526 and U.S. Patent Publication No. 20130196373.

The region that is located adjacent to the R0 repeat on the N-terminal side can be referred to as the "R-1" region (or sequence) and the region located adjacent to the R0 repeat on the C-terminal side is referred to as the "R1" region (or sequence). Thus, both the R-1 and R0 repeats are within the N-cap. The R-1 region comprises a sequence of amino acids that display some characteristics resembling a regular TALE repeat unit, and thus may interact with the R0 repeat in a stabilizing manner or interact with a T (or the A base-paired to the T in double-stranded DNA) adjacent to the target sequence specified by the TALE repeats. See, e.g., U.S. Pat. No. 8,586,526 and U.S. Patent Publication No. 20130196373.

The term "C-cap" or "C-terminal region" refers to optionally present amino acid sequences (polypeptides) that may be flanking the C-terminal portion of the TALE repeat domain. The C-cap can also comprise any part of a terminal C-terminal TALE repeat, including 0 residues, truncations of a TALE repeat or a full TALE repeat. The first 20 residues of the C-terminal region are typically homologous to the first 20 residues of a TALE repeat unit and may contain an RVD sequence capable of specifying the preference of nucleotides 3' of the DNA sequence specified by the TALE repeat domain. When present, this portion of the C-terminal region homologous to the first 20 residues of a TALE repeat is also referred to as the "half repeat." The numbering scheme of residues in the C-terminal region reflects this typical partial homology where the number scheme starts at C−20, increments to C−19, C−18, C−17, C−16, C−15, C−14, C−13, C−12, C−11, C−10, C−9, C−8, C−7, C−6, C−5, C−4, C−3, C−2, C−1, increments to C+1, and then increments to C+2, C+3, etc. towards the C-terminus of the polypeptide. A C+28 C-cap refers to the sequence from residue C−20 to residue C+28 (inclusive) and thus has a length of 48 residues. The C-cap sequences may be naturally occurring (e.g., fragments of naturally occurring proteins) or non-naturally occurring (e.g., a fragment of a naturally occurring protein comprising one or more amino acid deletions, substitutions and/or additions), or any other natural or non-natural sequence with the ability to act as a C cap. The C-terminal region is not absolutely required for the DNA-binding function of the TALE repeat domain(s), but, in some embodiments, a C-cap may interact with DNA and also may enhance the activity of functional domains, for example in a fusion protein comprising a nuclease at the C-terminal to the TALE repeat domain. See, e.g., U.S. Pat. No. 8,586,526 and U.S. Patent Publication No. 20130196373.

TALE binding domains can be "engineered" to bind to a predetermined nucleotide sequence, for example via engineering (altering one or more amino acids) of the RVD of the repeat units of the TALE protein. Therefore, engineered DNA binding proteins (TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing TALE designs and binding data. See, for example, U.S. Pat. No. 8,586,526 and U.S. Patent Publication No. 20130196373.

A "selected" TALE is a protein not found in nature whose production results primarily from an empirical process such as phage display, interaction trap or hybrid selection. See e.g., U.S. Pat. No. 8,586,526 and U.S. Patent Publication No. 20130196373.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional nucleases (e.g., zinc-finger nucleases, TALEN and/or CRISPR/Cas) can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cells and cell lines with partially or completely inactivated genes (e.g., using TALENs as described herein) are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present. In other embodiments, targeted alteration is via non-homology dependent mechanisms, for example, non-homologous end joining (NHEJ). See, e.g., U.S. Patent Publication Nos. 20110207221 and 20110287545.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+and-cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween). The donor sequence may be single- and/or double-stranded.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity using standard techniques. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods known in the art. Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a TALE as described herein. Thus, gene inactivation may be partial or complete.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soy, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells andanimal cells, including mammalian cells and human cells (e.g., stem cells).

"The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a TALE is fused to an activation domain, the TALE DNA-binding domain and the activation domain are in operative linkage if, in the fusion polypeptide, the TALE DNA-binding domain portion is able to bind its target site and/or its binding site, while the activation domain is able to upregulate gene expression. When a fusion polypeptide in which a TALE is fused to a cleavage domain, the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples safe harbor loci in mammalian cells include, for example, a CCR5 gene, a CXCR4 gene, a PPP1R12C (also known as AAVS1) gene, an albumin gene or a *Rosa* gene. See, e.g., U.S. Pat. Nos. 7,951,925 and 8,110,379; U.S. Publication Nos. 201000218264; 20100291048; 20120017290; 20110265198; 20130137104; 20130122591; 20130177983 and 20130177960. An exemplary safe harbor in a plant cell is the ZP15 locus (U.S. Pat. No. 8,329,986).

The terms "subject" and "patient" are used interchangeably and refer to mammals such as human patients and non-human primates, as well as experimental animals such as rabbits, dogs, cats, rats, mice, rabbits and other animals. Accordingly, the term "subject" or "patient" as used herein means any mammalian patient or subject to which the or stem cells of the invention can be administered.

TALE DNA Binding Domains

TALEs contain a central repeat domain that mediates DNA recognition, with each repeat unit containing approximately 33-35 amino acids specifying one target base. Repeat sequences are generally of the form: $X^1$-$X^2$-$X^3$-$X^4$-$X^5$-$X^6$-$X^7$-$X^8$-$X^9$-$X^{10}$-$X^{11}$-$(X^{RVD})_2$-$(X)_{20\text{-}22}$ (SEQ ID NO:12), where X is any amino acid and $X^{RVD}$ (positions 12 and 13) is involved in DNA binding. TALEs may also contain nuclear localization sequences and several acidic transcriptional activation domains (see, e.g., Schornack S, et al (2006) *J Plant Physiol* 163(3): 256-272). DNA-binding specificity of these TALEs depends on the sequences found in the tandem TALE repeat units. The repeated sequence comprises approximately 33-35 amino acids and the repeats are typically 91-100% homologous with each other (Bonas et al, ibid). There appears to be a one-to-one correspondence between the identity of the hypervariable diresidues at positions 12 and 13 with the identity of the contiguous nucleotides in the TALE's target sequence (see Moscou and Bogdanove, ibid and Boch et at ibid). These two adjacent amino acids are referred to as the Repeat Variable Diresidue (RVD). Experimentally, the natural code for DNA recognition of these TALEs has been determined such that an HD sequence at positions 12 and 13 leads to a binding to cytosine (C), NI to A, NN binds to G or A, and NG binds to T.

Designed TALE proteins have been used for targeting user-chosen DNA sequences and design principles, assembly methods, and a structural framework for engineering these proteins using canonical RVDs have been described. See. e.g., Moscou et al. (2009) *Science* 326:1501; Boch et al. (2009) Science 326:1509-1512 (2009); Cermak et al. (2011) *Nucleic Acids Res* 39: e82; Streubel et al. (2012) *Nat Biotechnol* 30:593-595; Sanjana et al. (2012) *Nat Protoc* 7:171-192; Reyon et al. (2012) *Nat Biotechnol* 30:460-465; Zhang et al. (2011) *Nat Biotechnol* 29:149-153; Sander et al. (2011) *Nat Biotechnol* 29:697-698; Morbitzer et al. (2011) *Nucleic Acids Res* 39:5790-5799; Li et al. (2011) *Nucleic Acids Res* 39:6315-6325; Schmid-Burgk et al. (2013) *Nat Biotechnol* 31:76-81; Kim et al. (2013) *Nat Biotechnol* 31:251-258; Deng et al. (2012) *Science* 335:720-723; Mak et al. (2012) *Science* 335:716-719; Stella et al. (2013) *Acta Crystallogr D Biol Crystallogr* 69:1707-1716. In addition, TALEs comprising certain non-canonical RVDs have also been described. See, e.g., U.S. Pat. No. 8,586,526 and U.S. Patent Publication 20130196373.

Described herein are TALEs comprising one or more non-canonical RVDs. The polypeptides described herein comprise one or more (e.g., 1, 2, 3, 4, 5, 6, 7, 8, 9, 10, 11, 12, 13, 14, 15, 16, 17, 18, 19, 20 or even more) TALE-repeat units. In certain embodiments, none of the repeat units include any canonical RVDs. In certain embodiments, the TALE protein comprises a non-canonical RVD of VG, IG, MG, EG, EP, EP, VA, or QG which specify thymine (T). In other embodiments, the TALE protein comprises a non-canonical RVD of GN, VN, LN, DN, QN, EN, RH, AN or FN which specify guanine (G). In other embodiments, the TALE protein comprises a non-canonical RVD of CI or KI that specifies adenine (A). In other embodiments, the TALE protein comprises a non-canonical RVD of RD, KD or AD, which specifies cytosine (C).

In still further embodiments, the first repeat of the TALE recognizes an adenine (A) (e.g., at the 5' end of the target site). Furthermore, any of the TALE proteins described herein may bind to a target site that (i) does not have a 3' adenine and/or (ii) runs of 3 or more successive thymines. In another embodiment, the TALE protein targets a sequence that does not contain the dinucleotide: guanine-guanine (GG). In another embodiment, the TALE protein targets a sequence that does not contain the dinucleotide: guanine-cytosine (GC). In another embodiment, the TALE protein targets a sequence that does not contain the trinucleotide thymine-thymine-thymine (TTT).

TALE proteins designed using these methods are also provided.

The TALE-repeat units of the compositions and methods described herein may be derived from any suitable TALE-protein. Non-limiting examples of TALE proteins include TALE proteins derived from *Ralstonia spp.* or *Xanthamonas spp.* Thus, in some embodiments, the DNA-binding domain comprises one or more naturally occurring and/or engineered TALE-repeat units derived from the plant pathogen *Xanthomonas* (see Boch et al, ibid and Moscou and Bogdanove, ibid). In other embodiments, the DNA-binding domain comprises one or more naturally occurring and/or engineered TALE-repeat units derived from the plant pathogen *Ralstonia solanacearum*, or other TALE DNA binding domain from the TALE protein family. The TALE DNA binding domains as described herein (comprising at least one TALE repeat unit) can include (i) one or more TALE repeat units not found in nature; (ii) one or more naturally occurring TALE repeat units; (iii) one or more TALE repeat units with atypical RVDs; and combinations of (i), (ii) and/or (iii). In some embodiments, a TALE DNA binding domain of the invention includes only non-naturally occurring or atypical repeat units. Furthermore, in polypeptides as described herein comprising two or more TALE-repeat units, the TALE-repeat units (naturally occurring or engineered) may be derived from the same species or alternatively, may be derived from different species.

The DNA-binding polypeptides comprising TALE-repeat domains as described herein may also include additional TALE polypeptide sequences, for example N-terminal (N-cap) sequences and, optionally, C-terminal (C-cap) sequences flanking the repeat domains. See, e.g., U.S. Pat. No. 8,586,526 and U.S. Patent Publication No. 20130196373. N-cap sequences may be naturally or non-naturally occurring sequences of any length sufficient to support the function (e.g., DNA-binding, cleavage, activation, etc.) of the DNA-binding polypeptide and fusion proteins comprising these TALE-repeat domain-containing DNA-binding polypeptides. In certain embodiments, the protein comprises an N-cap sequence comprising a fragment (truncation) of a region of a TALE protein N-terminal to the repeat domain (e.g., an N-cap sequence comprising at least 130 to 140 residues (e.g., 131, 132, 133, 134, 135, 136, 137, 138, 139 or 140 residues) of a TALE polypeptide N-terminal of the repeat domain). In other embodiments, the TALE-repeat domain polypeptides as described herein comprises a C-cap sequence comprising a fragment (truncated) region of a TALE protein C-terminal to the repeat domain (e.g., an C-cap sequence comprising C−20 to C+28, C−20 to C+55, or C−20 to C+63). In certain embodiments, the C-cap sequence comprises a half-repeat (C−20 to C−1). The TALE DNA-binding polypeptides as described herein may include N-cap, C-cap sequences or both N-cap and C-cap sequences.

Multi TALE repeat modules may also be useful not only for assembling the DNA binding domains (comprising at least one TALE repeat unit) as described above, but also may be useful for the assembly of mini-TALE multimers (i.e. 3 or more repeat units, including trimers, tetramers, pentamers, hexamers etc.), wherein spanning linkers that also functioned as capping regions between the mini-TALE DNA binding domains would allow for base skipping and may result in higher DNA binding specificity. The use of linked mini-TALE DNA binding domains would relax the requirement for strict functional modularity at the level of individual TALE repeats and allows for the development of more complex and/or specific DNA recognition schemes wherein amino acids from adjacent motifs within a given module might be free to interact with each other for cooperative recognition of a desired DNA target sequence. Mini-TALE DNA binding domains could be linked and expressed using a suitable selection system (i.e. phage display) with randomized dipeptide motifs (or any other identified key positions) and selected based on their nucleic acid binding characteristics. Alternatively, multi-TALE repeat modules may be used to create an archive of repeat modules to allow for rapid construction of any specific desired TALE-fusion protein.

Fusion Molecules

Any of the TALE proteins described herein may be fused to one or more additional molecules. In certain embodiments, the TALE domains as described herein are fused to one or more heterologous peptide domains, for example a functional domain.

Common domains include, e.g., transcription factor domains (activators, repressors, co-activators, co-repressors), nuclease domains, silencer domains, oncogene domains (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e g kinases, acetylases and deacetylases); and DNA modifying enzymes (e.g., methyltransferases, topoisomerases, helicases, ligases, kinases, phosphatases, polymerases, endonucleases), DNA targeting enzymes such as transposons, integrases, recombinases and resolvases and their associated factors and modifiers, nuclear hormone receptors, nucleases (cleavage domains or half-domains) and ligand binding domains.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Bark *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci.* USA 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) Gene 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains include, but are not limited to, KRAB A/B, KOX, TGF-beta-inducible early gene (TIEG), v-crbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

The fusion molecule may be formulated with a pharmaceutically acceptable carrier, as is known to those of skill in the art. See, for example, Remington's Pharmaceutical Sciences, 17th ed., 1985; and co-owned WO 00/42219.

In certain embodiments, the TALE DNA-binding proteins, or fragments thereof, are used as nucleases via fusion (N- and/or C-terminal to the TALE-repeat domain, N-cap and/or C-cap sequences) of a TALE DNA-binding domain to at least one nuclease (cleavage domain, cleavage half-domain). The cleavage domain portion of the fusion proteins disclosed herein can be obtained from any endonuclease or exonuclease.

Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

TALEs linked to nuclease (cleavage domains) to form nuclease hybrids (TALENs) have been used for genome editing in higher eukaryotes. See, e.g., U.S. Pat. No. 8,586,526; U.S. Patent Publication 20130196373; Christian et al. (2010) *Genetics* 186:757-76; Li et al. (2011) *Nucleic Acids Res* 39:359-372. With the development of a highly active TALEN architecture described in U.S. Pat. No. 8,586,526 (C-cap and/or N-caps), TALEN-mediated genome editing has been demonstrated in a wide range of cell types including human primary and stem cells, as well as in plants, nematodes, insects, fish, frogs, mice, rats, rabbits and pigs. See, e.g., Miller et al. (2011) *Nat Biotechnol* 29:143-148; Hockemeyer et al. (2011) *Nat Biotechnol* 29:731-734; Li et al. (2012) *Nat Biotechnol* 30:390-392; Wood et al. (2011) *cience* 333:307 (2011); Watanabe et al. (2012) *Nat Commun* 3:1017 (2012); Liu et al. (2012) *J Genet Genomics* 39:209-215; Ma et al. (2012)*PLoS One* 7: e45035; Huang et al. (2011) *Nat Biotechnol* 29:699-700; Lei et al. (2013) *Cell Biosci* 3: 2; Sung et al. (2013) *Nat Biotechnol* 31:23-24; Tesson et al. (2011) *Nat Biotechnol* 29:695-696.

Thus, any suitable cleavage domain can be operatively linked to a TALE DNA-binding domain as described herein to form a nuclease. For example, TALE DNA-binding domains have been fused to nuclease domains to create TALENs. See, e.g., U.S. Pat. No. 8,586,526 and U.S. Patent Publication No. 20130196373.

As noted above, the cleavage domain may be heterologous to the DNA-binding domain, for example a TALEN DNA-binding domain and a cleavage domain from any nuclease. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the TALEN comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et at (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. patents 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more TALE proteins as described herein.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using TALE-Fok I fusions, two fusion proteins, each comprising a FokI cleavage half-domain, can be used to reconstitute a catalytically active cleavage domain. Alternatively, a single polypeptide molecule containing a TALE DNA binding domain and two Fok I cleavage half-domains can also be used. Parameters for targeted cleavage and targeted sequence alteration using TALE-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. Nos. 7,888,121; 7,972,854 and 8,409,861. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 7,914,796; 8,034,598; 8,409,861 and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 20110201055). In other embodiments, the engineered cleavage half domain comprises the "Sharkey" and/or "Sharkey' " mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598; 8,623,618 and 8,409,861; and U.S. Patent Publication No. 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual TALE binding domains or domains of a meganuclease nucleic acid binding domain.

Nucleases can be screened for activity prior to use, for example in a yeast-based chromosomal system as described in U.S. Pat. No. 8,563,314. Nuclease expression constructs can be readily designed using methods known in the art. See, e.g., U.S. Pat. No. 8,586,526 and U.S. Patent Publication No. 20130196373. Expression of the nuclease may be under the control of a constitutive promoter or an inducible promoter, for example the galactokinase promoter which is activated (de-repressed) in the presence of raffinose and/or galactose and repressed in presence of glucose.

Artificial fusion proteins linking TALE DNA binding domains to zinc finger DNA binding domains may also be produced. These fusions may also be further linked to a desired functional domain.

Target Sites

As described in detail above, the TALEs described herein are engineered to bind to any sequence of choice and, therefore, can have a novel binding specificity, compared to a naturally-occurring DNA-binding domain. Engineering methods include, but are not limited to, rational design and various types of selection. See, e.g., U.S. Pat. No. 8,586,526 and U.S. Patent Publication No. 20130196373.

As noted above, the DNA-binding domains of the nucleases may be targeted to any gene. In certain embodiments, the nuclease (DNA-binding domain component) is targeted to a "safe harbor" locus, which includes, by way of example only, a CCR5 gene, an HPRT gene, a PPP1R12C (also known as AAVS1) gene, or a Rosa gene in mammalian cells, and the Zp15 locus in plants. See, e.g., U.S. Pat. Nos. 7,951,925; 8,110,379 and 8,329,986; U.S. Publication Nos. 20080159996; 201000218264; 20100291048; 20120017290; 20110265198; 20130137104; 20130122591; 20130177983 and 20130177960.

The target site may be of any length. Typically, the target site for an individual TALE protein is between about 5 and 35 base pairs in length (including any length therebetween) and more preferably between 10 and 25 base pairs (including 10, 11, 12, 13, 14, 15, 16, 17, 18, 19, 20, 21, 22, 23, 24, or 25 base pairs).

The target site can be of any sequence. In certain embodiments, the target site is selected such that it does not comprise 3 contiguous thymines (Ts) and/or the base recognized by the amino-terminal repeat is an adenine (A) and/or the base recognized by the carboxy-terminal half repeat is not an adenine (A) and the target site is chosen so that it does not contain 5'-GG-3' or 5'-GC-3' dinucleotides. In addition, depending on the target site selected, the TALE can be designed for enhanced binding specificity and/or activity.

Donors

The present disclosure includes TALEs and methods of using these TALEs for nuclease-mediated targeted integration of an exogenous sequence (also called a "donor sequence" or "donor" or "transgene"), into the genome of a cell, for example for correction of a mutant gene or for increased expression of a wild-type gene. It will be readily apparent that the donor sequence is typically not identical to the genomic sequence where it is placed. A donor sequence can include regions of homology (e.g., homology arms) for HDR-mediated integration or can be integrated via NHEJ donor capture. See, e.g., U.S. Patent Publication Nos. 20110207221 and 20110287545, The donor polynucleotide can be DNA or RNA, single-stranded and/or double-stranded and can be introduced into a cell in linear or circular form. See, e.g., U.S. Pat. No. 8,623,618 and U.S. Publication Nos. 20100047805 and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No.102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal or plant) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HcLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces* as well as plant cells from monocotyledonous or dicotyledonous plants In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the TALEN(s) as described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA or RNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, Science 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered TALEs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery for TALEs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)).

PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 20090117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, the nucleases and donors can be carried by the same or different vectors. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemophilias via nuclease-mediated integration of clotting factors such as Factor VIII (F8). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. See, also, U.S. Pat. No. 8,399,218; 8,329,986; 8,329,986 and U.S. Publication No. and 20110189775, incorporated herein by reference in their entireties.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming of oncogenes and the development and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti,* potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5, 591,616; Hernalsteen et al. (1984) *EMBO J* 3:3039-3041; Hooykass-Van Slogteren et al.(1984) *Nature* 311:763-764; Grimsley et al. (1987) *Nature* 325: 1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al.(1985) *Proc. Nat. Acad. Sci.* USA 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide (e.g., WHISKERS™) mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.*

The introduction of nucleic acids introduced into a plant cell can be used to confer desired traits on essentially any plant. In certain embodiments, the altered MDH expression/function in plant cells results in plants having increased amount of fruit yield, increased biomass of plant (or fruit of the plant), higher content of fruit flesh, concentrated fruit set, larger plants, increased fresh weight, increased dry weight, increased solids context, higher total weight at harvest, enhanced intensity and/or uniformity of color of the crop, altered chemical (e.g., oil, fatty acid, carbohydrate, protein) characteristics, etc.

One with skill in the art will recognize that an exogenous sequence can be transiently incorporated into a plant cell. The introduction of an exogenous polynucleotide sequence can utilize the cell machinery of the plant cell in which the sequence has been introduced. The expression of an exogenous polynucleotide sequence comprising a TALEN that is transiently incorporated into a plant cell can be assayed by analyzing the genomic DNA of the target sequence to identify and determine any indels, inversions, or insertions. These types of rearrangements result from the cleavage of the target site within the genomic DNA sequence, and the subsequent DNA repair. In addition, the expression of an exogenous polynucleotide sequence can be assayed using methods which allow for the testing of marker gene expression known to those of ordinary skill in the art. Transient expression of marker genes has been reported using a variety of plants, tissues, and DNA delivery systems. Transient analyses systems include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses the use of any transient expression system to evaluate a site specific endonuclease and to introduce mutations within an MDH target gene. Examples of plant tissues envisioned to test in transients via an appropriate delivery system would include but are not limited to leaf base tissues, callus, cotyledons, roots, endosperm, embryos, floral tissue, pollen, and epidermal tissue.

One of skill in the art will recognize that an exogenous polynucleotide sequence can be stably incorporated in transgenic plants. Once the exogenous polynucleotide sequence is confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing stably inserted gene constructs, or plant cell containing target gene altered genomic DNA which results from the transient expression of a site-specific endonuclease (e.g., TALEN). These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Pat. No. 7,838,733, which reference is hereby incorporated by reference in its entirety herein. A transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., TALENs) and expression vectors encoding fusion proteins can be administered directly to the plant for gene regulation, targeted cleavage, and/or recombination. In certain embodiments, the plant contains multiple paralogous MDH target genes. Thus, one or more different fusion proteins or expression vectors encoding fusion proteins may be administered to a plant in order to target one or more of these paralogous genes in the plant.

Administration of effective amounts is by any of the routes normally used for introducing fusion proteins into ultimate contact with the plant cell to be treated. The TALEs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

The following Examples relate to exemplary embodiments of the present disclosure only and are not to be construed as limiting.

EXAMPLES

Example 1

Materials and Methods

TALE Constructs

TALE proteins were generated essentially as described in U.S. Pat. No. 8,586,526; U.S. Publication No. 20130196373 and Miller et al. (2011) Nat Biotechnol 29: 143-148 using standard molecular biology methods. Details about the proteins used in the studies described herein are found in Miller et al. (2015) Nature Methods Mar 23. doi: 10.1038/nmeth.3330. For large scale RVD ELISA studies, each TALE construct was assembled by annealing two complementary oligonucleotides (5'-AATCGCGTCGxxxxxxGGGGGAAAG (SEQ ID NO:13) and 5'-CTTGCTTTCCCCC CGACGC (SEQ ID NO:14), where the varied region encodes each possible RVD) and ligating the resultant duplex into the vector pVAXt-TALE-TGAC-Bsa2-ATCC-C63-Fok, which had been linearized via digestion with BsaI.

An exemplary TALE protein sequence used for studies where one RVD was varied is provided below. Invariant RVDs are underlined, while the double underlined xx highlights the RVD that was varied between constructs:

(SEQ ID NO: 15)
MDYKDHDGDYKDHDIDYKDDDDKMAPKKKRKVGIHRGVPMVDLRTLGYSQ

QQQEKIKPKVRSTVAQHHEALVGHGFTHAHIVALSQHPAALGTVAVKYQD

MIAALPEATHEAIVGVGKQWSGARALEALLTVAGELRGPPLQLDTGQLLK

IAKRGGVTAVEAVHAWRNALTGAPLNLTPDQVVAIAS<u>N</u>GGGKQALETVQR

LLPVLCQDHGLTPDQVVAIAN<u>NN</u>GGKQALETVQRLLPVLCQAHGLTPDQV

VAIAS<u>N</u>IGGKQALETVQRLLPVLCQAHGLTPAQVVAIAS<u>HD</u>GGKQALETV

QRLLPVLCQDHGLTPDQVVAIAS<u>xx</u>GGKQALETVQRLLPVLCQDHGLTPD

QVVAIAS<u>N</u>IGGKQALETVQRLLPVLCQDHGLTPEQVVAIAS<u>N</u>GGGKQALE

TVQRLLPVLCQAHGLTPDQVVAIAS<u>HD</u>GGKQALETVQRLLPVLCQAHGLT

PAQVVAIAS<u>HD</u>GGKQALETVQRLLPVLCQDHGLTPEQVVAIAS<u>N</u>GGGRPA

LESIVAQLSRPDPALAALTNDHLVALACLGGRPALDAVKKGLPHAPALIK

RTNRRIPERTSHRVAGSQLVKSELEEKKSELRHKLKYVPHEYIELIEIAR

NSTQDRILEMKVMEFFMKVYGYRGKHLGGSRKPDGAIYTVGSPIDYGVIV

DTKAYSGGYNLPIGQADEMQRYVEENQTRNKHINPNEWWKVYPSSVTEFK

FLFVSGHFKGNYKAQLTRLNHITNCNGAVLSVEELLIGGEMIKAGTLTLE

EVRRKFNNGEINFRS

Constructs for tetramer ELISA studies were generated in two steps. First, TALE repeat monomer vectors, encoding the non-canonical RVDs were created by ligating the annealed oligonucleotides into the position-specific monomer hosting vectors, pTAL-Bsa-BsmBI -M1, -M2, -M3 or -M4, which had been linearized via digestion with BsmBI. Next, amplicons encoding each monomer repeat were amplified from these vectors using the primers TMF (5'-CGGCCTGCGTCGACGAATTCG, SEQ ID NO:16) and TMR (5'- CACAGCCTGAGCTCTCTAGAG, SEQ ID NO:17), pooled, digested with BsaI, and ligated into a linearized host vector. Tetramer pools corresponding to the TCAT and CTTC targets were ligated into their host vector as repeats 1-4 of a nine repeat TALE while tetramer pools corresponding to the TACA, CCTG, CAGC, CAGC, ATTG and ATAC targets were ligated into a different host vector as repeats 5-8 of a nine-repeat TALE. Ligations were transformed into TOP 10 E. coli competent cells (Life Technology), and individual clones were randomly picked, sequenced and archived for analysis in the tetramer ELISA studies.

To generate CCR5-targeted TALEN constructs bearing exclusively non-canonical RVDs, DNA fragments encoding high-affinity tetramers as identified in ELISA studies were PCR-amplified using primers specific to the ultimate tetramer position in the TALEN transgene as shown below:

Tetramer 1 (repeats 1-4):
T1F
(SEQ ID NO: 18)
(5'-GGATCCGGATGGTCTCAACCTGACCCCAGACCAG)

T1R
(SEQ ID NO: 19)
(5'-GAGGGATGCGGGTCTCTGAGTCCATGATCCTGGCACAGT)

Tetramer 2 (repeats 5-8):
T2F
(SEQ ID NO: 20)
(5'-GGATCCGGATGGGTCTCAACTCACCCCAGACCAGGTA)

```
T2R
                                          (SEQ ID NO: 21)
(5'-GAGGGATGCGGGTCTCTCAGCCCATGATCCTGGCACAGT)

Tetramer 3 (repeats 9-12):
T3F
                                          (SEQ ID NO: 22)
(5'-GGATCCGGATGGGTCTCAGCTGACCCCAGACCAG)

T3R
                                          (SEQ ID NO: 23)
(5'-GAGGGATGCGGGTCTCTCAAACCATGATCCTGGCACAGT)

Tetramer 4 (repeats 13-16):
T4F
                                          (SEQ ID NO: 24)
(5'-GGATCCGGATGGGTCTCATTTGACCCCAGACCAGGTA)

*T4R_HG-T-Bsa
                                          (SEQ ID NO: 25)
(5'-CTCGAGGGATGGTCTCCGTCCTCCGCCGTGGCTAGCAATGGCGACC

ACCTGTTCGGGTGTCAGGCCATGATCC)

*T4R_KG-T-Bsa
                                          (SEQ ID NO: 26)
(5'-CTCGAGGGATGGTCTCCGTCCTCCGCCCTTGCTAGCAATGGCGACC

ACCTGTTCGGGTGTCAGGCCATGATCC)

*equimolar mix used
```

PCR products were pooled as appropriate, digested with BsaI, and ligated into the TALEN expression vector, pVAXt-3Flag-NLS-TALE-Bsa3-C63-Fok, which had been linearized via digest with BsaI. Ligations were transformed into TOP10 E. coli competent cells (Life Technology), and single clones were randomly picked and sequenced.

A similar procedure was used to generate the discrete TALEN constructs except that (i) tetramers coding for unique TALENs were used instead of mixed pools, and (ii) a discrete reverse primer—which encodes the RVD of the final half-repeat—was used for the tetramer 4 PCR. Primer sequences and the resulting RVD encoded by the final half repeat are as follows:

```
T4R_NG-T-Bsa
                                          (SEQ ID NO: 27)
5'-CTCGAGggatggtctcCGTCCTCCCCCGTTGCTAGCAATGGCGACCA

CCTGTTCGGGTGTCAGGCCATGATCC

T4R_HG-T-Bsa
                                          (SEQ ID NO: 28)
5'-CTCGAGggatggtctcCGTCCTCCGCCGTGGCTAGCAATGGCGACCA

CCTGTTCGGGTGTCAGGCCATGATCC

T4R_KG-T-Bsa
                                          (SEQ ID NO: 29)
5'-CTCGAGggatggtctcCGTCCTCCGCCCTTGCTAGCAATGGCGACCA

CCTGTTCGGGTGTCAGGCCATGATCC

T4R_QG-T-Bsa
                                          (SEQ ID NO: 30)
5'-CTCGAGggatggtctcCGTCCTCCGCCCTGGCTAGCAATGGCGACCA

CCTGTTCGGGTGTCAGGCCATGATCC

T4R_SG-T-Bsa
                                          (SEQ ID NO: 31)
5'-CTCGAGggatggtctcCGTCCTCCGCCGCTGCTAGCAATGGCGACCA

CCTGTTCGGGTGTCAGGCCATGATCC

T4R_RG-T-Bsa
                                          (SEQ ID NO: 32)
5'-CTCGAGggatggtctcCGTCCTCCGCCCCTGCTAGCAATGGCGACCA

CCTGTTCGGGTGTCAGGCCATGATCC
```

SELEX Studies

Experimental conditions used to characterize the PitX3 TALENs (data in FIG. 3) were essentially as described in U.S. Pat. No. 8,586,526; U.S. Publication No. 20130196373 and Miller et al. (ibid).

Briefly, an oligonucleotide target library was synthesized bearing the sequence:

```
                                          (SEQ ID NO: 33)
5'-CAGGGATCCATGCACTGTACGCCCNNNNNNNNNNNNNNNNNNNNNNGG

GCCACTTGACTGCGGATCCTGG-3',
``` where "N" denotes a mixture of all four bases. The library was converted to double-stranded duplex by annealing 2 nmol of library oligo with 16 nmol of 3' library primer (5'-CCAGGATCCGCAGTCAAGTGG (SEQ ID NO:57) in 100 µl 1× PCR Master (Roche) supplemented to 2.5 mM of each dNTP and 5 mM $MgSO_4$, followed by incubation at 95° C. for 2 min, 94° C. for 5 min, 58° C. for 5 min, and 72° C. for 15 min.

DNA fragments encoding TALE proteins were amplified via PCR using a 5' primer bearing a T7 promoter: 5'-GCT-TACTGGCTTATCGAAATTAATACGACTCAC-TATAGGGAGACGAATTCAC CACCATGGTGGATC-TACGCACGCTCG-3' (SEQ ID NO:34) and a 3' primer encoding an in-frame HA-epitope tag: 5'-CACGTACTTCA-GCTTTTATTAGGCGTAGTCGGGCACGTCGTAGGGG-TAGCCCG CGACTCGATGGGAAGTTC-3' (SEQ ID NO:35).

Protein was then expressed by adding 2 µl of the PCR product to 10 µl TnT coupled transcription-translation system (Promega). After incubating at 30° C. for 80 minutes, the resulting reaction was mixed with 200 pmol of library duplex and SELEX buffer (0.01% BSA, 0.05% Tween 20, 0.5 mM $MgCl_2$, 20 µg/ml poly dIdC in calcium-free PBS) to a final volume of 90 µl and incubated for 30 minutes at room temperature. Next 3 µl Roche Anti-HA-Biotin Clone 3F10 (diluted in a total volume of 1 ml $H_2O$) and 7 µl SELEX buffer was added to each reaction. After an additional incubation for 20 minutes, protein-DNA-antibody complexes were captured on streptavidin coated magnetic beads (Invitrogen). Bound DNA target was then amplified via PCR using the 3' library primer and 5' library primer (5'-CA-GGGATCCATGCACTGTACG) (SEQ ID NO:36), and subjected to additional cycles of enrichment. A total of 3 rounds of enrichment were used prior to cloning and sequencing selected sequences.

Figure 6A:
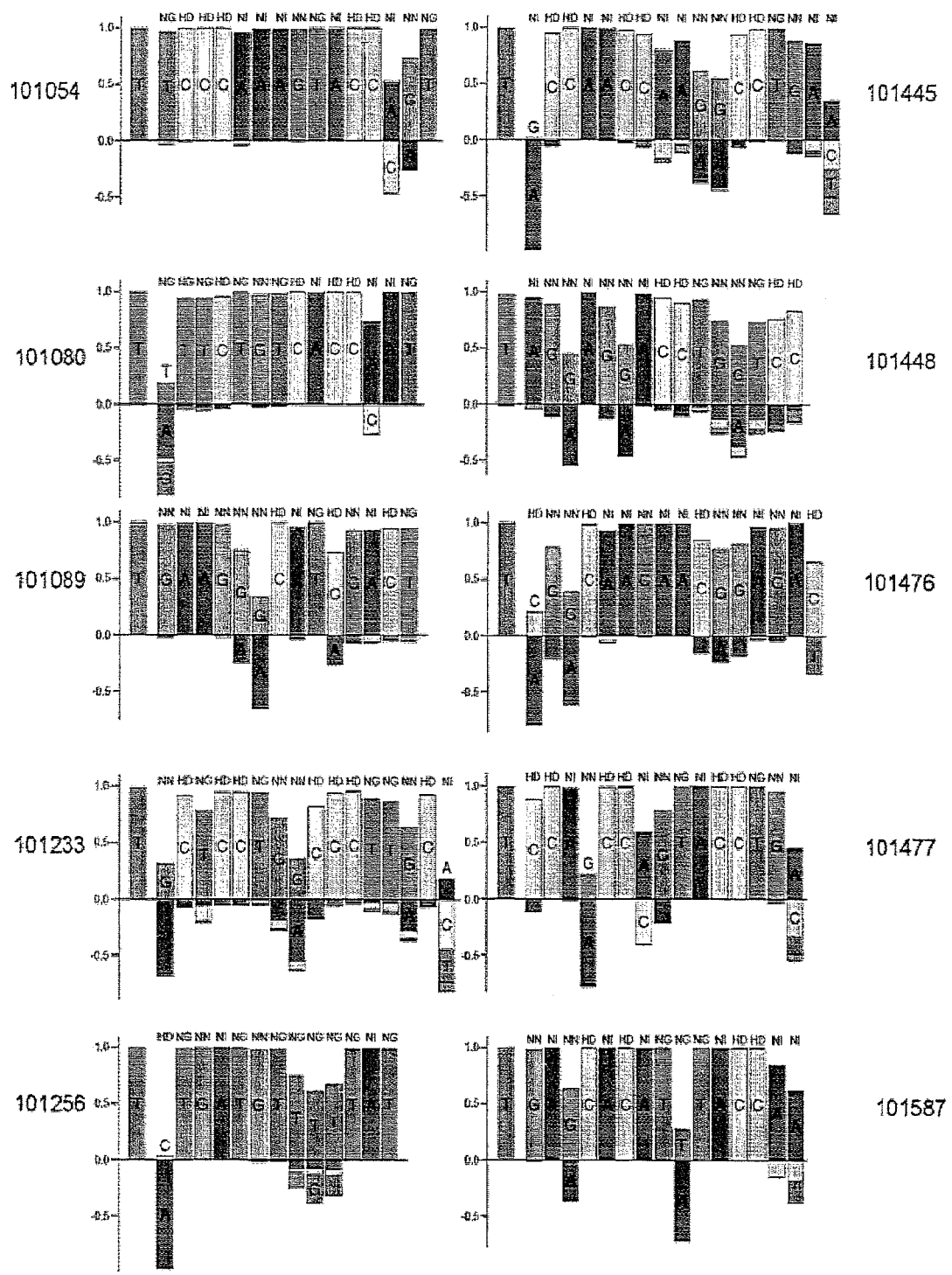
FIGS. 6A through 6C depict TALE binding characteristics.
Figure 6B:
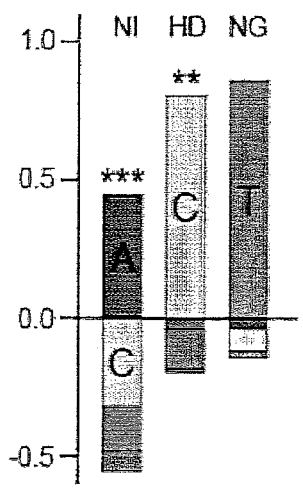
Figure 6C:
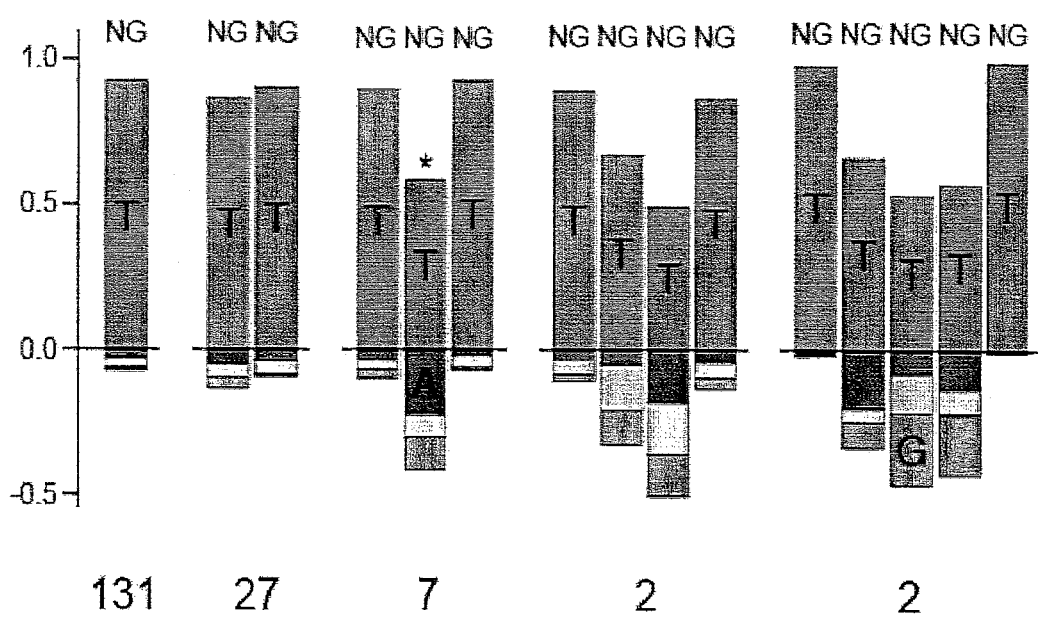

For characterization of certain TALENs (as shown in FIGS. 1 and 6), an alternative SELEX protocol was used that had been optimized for performance at the larger scale of these studies. The randomized duplex library was generated essentially as described above, except that 6 nmol of 3' library primer and 1.2 mM of each dNTP were used. For the first assay cycle, TALENs were expressed directly from plasmid templates using a TnT coupled transcription-translation system (Promega) and the manufacturer's recommended conditions with buffers supplemented to 10 mM $ZnCl_2$. Expressed TALENs contained a triple Flag tag fused to their N-terminus. 12 µl of TnT reaction mix was then mixed with 200 pmol of library duplex in a total volume of 100 µl of binding buffer (50 mM DTT, 10 µM $ZnCl_2$, 5 mM $MgCl_2$, 0.01% BSA Fraction V, 100 mM NaCl in PBS (calcium-free)).

After incubation for 50 min protein-DNA complexes were captured on anti-FLAG M2 magnetic beads (SIGMA) and washed five times with wash buffer (5 mM DTT, 10 µM $ZnCl_2$, 5 mM $MgCl_2$, 0.01% BSA Fraction V, 100 mM NaCl in PBS (calcium-free)). Bound target was PCR-amplified using the 3' library primer (above) and a 5' library primer (5'-CAGGGATCCATGCACTGTACG) (SEQ ID NO:37), and the resulting amplicon was used as input for additional cycles of enrichment. Protein expression and binding conditions for these subsequent cycles were identical to the conditions used in the first round. After three cycles, recovered DNA fragments were sequenced using an Illumina MiSeq system. The protocol for adding the Illumina sequencing primers and sequencing is as described in the section on off-target analysis. Identical conditions were used to characterize L, L*, R and R* TALENs except that 48 µl of TnT extract was used for each binding reaction.

SELEX FASTQ sequences from the MiSeq were adapter trimmed using SeqPrep (as available on the internet). SELEX library sequences were further filtered by custom python scripts for correct length and fixed flanking region composition (exact match). 1000 randomly sampled filtered sequences were used as input to the GADEM motif discovery program with options mask R=0 fullscan=0 gen=3. Position frequency matrices discovered by GADEM were then aligned to the intended sequence and reverse-complemented if necessary. Matrices longer than the intended sequence were trimmed to only those regions overlapping the intended sequence according to the highest-scoring alignment.

Large Scale ELISA Study

Full sequences of the DNA binding site duplexes used in this assay were as follows, wherein underlining indicates the base position recognized by the varied RVD:

A-BS:
(SEQ ID NO: 38)
5'-CATAGTCCCCTTGACAATCCTCCTCGGTGTAGTTTTCACAGTCAGTC

CACACGTC

C-BS:
(SEQ ID NO: 39)
5'-CATAGTCCCCTTGACCATCCTCCTCGGTGTAGTTTTCACAGTCAGTC

CACACGTC

G-BS:
(SEQ ID NO: 40)
5'-CATAGTCCCCTTGACGATCCTCCTCGGTGTAGTTTTCACAGTCAGTC

CACACGTC

T-BS:
(SEQ ID NO: 41)
5'-CATAGTCCCCTTGACTATCCTCCTCGGTGTAGTTTTCACAGTCAGTC

CACACGTC

To generate the binding site premix used in each ELISA reaction, 100 pmol of the corresponding oligonucleotide was annealed to a 12.5 pmol of 5' biotinylated primer (5'-Biotin-GACGTGTGGACTGACTGTGA (SEQ ID NO:42)) and then incubated under the following conditions: 25 µl 1× Accuprime™ Buffer (Invitrogen)/Accuprime™ Taq enzyme/94° C., 3 min; 94° C., 30 sec; 3× (55° C., 30 sec; 68° C., 2 min); 68° C., 3 min. Biotinylated binding sites (0.375 pmol) were combined with 165 ng salmon sperm (Invitrogen) and 2.28 mU of anti-HA-peroxidase high affinity (Roche) in a total volume of 55 ul of ELISA Binding Buffer (0.5 mM $MgCl_2$, 10 um $ZnCl_2$, 0.5% Tween 20 and 0.01% BSA).

To run the assay, fragments encoding TALE proteins were amplified by PCR using a 5'-primer sequence (5'-GCAGAGCTCTCTGGCTAACTAGAG-3') (SEQ ID NO:43) and a 3'-primer encoding an in frame hemagglutinin (HA)-epitope tag (5'-GCGTAAAGCTTAGGCGTAGTCGGGCACGTCGTAGGGGTAGCCGGGCACCAGC TGGGATCCCCGCAGGTG) (SEQ ID NO:44). Proteins were expressed by adding the PCR product to a TnT-coupled transcription-translation system (Promega) supplemented with methionine and $ZnCl_2$ (final concentrations of 20 µM and 330 µM, respectively) and incubating as specified by the manufacturer. The binding site premix was then combined with the TnT reaction and incubated for 40 min. Streptavidin coated high binding capacity black 96-well plates (Pierce) were washed with PBS solution (supplemented with $MgCl_2$ and $ZnCl_2$ to final concentrations of 0.5 mM and 10 µM, respectively) using a ELx405 automated plate washer. DNA-protein-antibody complexes were captured by transferring the TnT/binding site mixture to the plate, incubating for 40 min, and washing with ELISA Binding Buffer using the ELx405. Immediately following the wash, 45 ul of QuantaBlu Substrate Solution (Pierce) and 5 ul of QuantaBlu Stable Peroxidase Solution (Pierce) were added to each well and developed for 30 minutes. Plates were read using a Gemini XS plate reader following the QuantaBlu protocol. Data was exported from the plate reader and analyzed in Microsoft Excel.

TALE Tetramer ELISA Study

TALE tetramer constructs were screened via an identical set of procedures, except that the target sequences for each tetramer were:

TCAT:
(SEQ ID NO: 45)
5'-CATAGTCCCCTTCATATCCTCCTCGGTGTAGTTTTCACAGTCAGTCC

ACACGTC

CTTC:
(SEQ ID NO: 46)
5'-CATAGTCCCCTCTTCATCCTCCTCGGTGTAGTTTTCACAGTCAGTCC

ACACGTC

-continued

TACA:

(SEQ ID NO: 47)
5'-CATAGTCCCCTTGAC<u>TACA</u>TCCTCGGTGTAGTTTTCACAGTCAGTCC

ACACGTC

CCTG:

(SEQ ID NO: 48)
5'-CATAGTCCCCTTGAC<u>CCTG</u>TCCTCGGTGTAGTTTTCACAGTCAGTCC

ACACGTC

CAGC:

(SEQ ID NO: 49)
5'-CATAGTCCCCTTGAC<u>CAGC</u>TCCTCGGTGTAGTTTTCACAGTCAGTCC

ACACGTC

CAGA:

(SEQ ID NO: 50)
5'-CATAGTCCCCTTGAC<u>CAGA</u>TCCTCGGTGTAGTTTTCACAGTCAGTCC

ACACGTC

ATTG:

(SEQ ID NO: 51)
5'-CATAGTCCCCTTGAC<u>ATTG</u>TCCTCGGTGTAGTTTTCACAGTCAGTCC

ACACGTC

ATAC:

(SEQ ID NO: 52)
5'-CATAGTCCCCTTGAC<u>ATAC</u>TCCTCGGTGTAGTTTTCACAGTCAGTCC

ACACGTC

Gene Modification of Endogenous CCR5 and PitX3

In order to screen TALEN pairs for NHEJ-mediated gene modification, K562 cells were cultured in RPMI1640 media (Invitrogen) supplemented with 10% (v/v) FBS, 2 mM L-glutamine, 100 U/ml penicillin, and 100 mg/ml streptomycin. Cells (1-2×10$^5$) were nucleofected with TALEN expression plasmids (400 ng each) using the Amaxa 96-well shuttle system (Amaxa Biosystems/Lonza) according to manufacturers' instructions. Cells were collected 3 days post-transfection and genomic DNA was extracted using the QuickExtract DNA Extraction Solution (Epicentre Biotechnologies) according to suppliers' instructions. Frequency of gene modification by NHEJ was evaluated by the Surveyor™ Nuclease Assay as described previously (U.S. Pat. No. 8,586,526) as well as deep sequencing using an Illumina MiSeq®.

Off-Target Analysis

Off-target loci were determined computationally by identifying all genomic sites with up to 8 mismatches relative to the intended TALEN binding sites with spacing between TALEN binding sites of 10 to 24 nucleotides. PCR primers were then designed using Primer3 with the following optimal conditions: amplicon size of 200 nucleotides, a Tm of 60° C., primer length of 20 nucleotides, and GC content of 50%. Adapters were added for a second PCR reaction to add the Illumina library sequences (SEQ ID NO: 53)
(ACACGACGCTCTTCCGATCT forward primer and (SEQ ID NO: 54)
GACGTGTGCTCTTCCGAT reverse primer.

Genomic DNA was purified with the Qiagen DNeasy® Blood and Tissue Kit (Qiagen). Regions of interest were amplified in 50 μusing 250 ng of genomic DNA with Phusion (NEB) in Buffer GC with 200 μM dNTPs. Amplification of OT20 required the addition of DMSO to a final concentration of 3%. Primers were used at a final concentration of 0.5 μM and the following cycling conditions: Initial melt of 98° C. 30 sec, followed by 30 cycles of 98° C. 10 sec, 60° C. 30 sec, 72° C. 15 sec, followed by a final extension 72° C. 10 min. PCR products were diluted 1:200 in H$_2$O. 1 μL diluted PCR product was used in a 10 μL PCR reaction to add the Illumina library sequences with Phusion (NEB) in Buffer GC with 200 μM dNTPs. Primers were used at a final concentration of 0.5 μM and the following conditions: Initial melt of 98° C. 30 sec, followed by 12 cycles of 98° C. 10 sec, 60° C. 30 sec, 72° C. 15 sec, followed by a final extension 72° C. 10 min. PCR products were pooled and purified using the Qiagen Qiaquick® PCR Purification Kit (Qiagen). Samples were quantitated with the Qubit® dsDNA HS Assay Kit (Life Technologies). Samples were diluted to 2 nM and sequenced on an Illumina MiSeq® Instrument (Illumina) with a 300 cycle sequencing kit.

Example 2

Reliability of the Natural TALE Code

Although the natural TALE code is often depicted as a binary matching of each RVD to its base target, previous studies had suggested that these preferences were not quantitatively absolute (Miller et al. ibid; Mali et al. (ibid).; Bogdanove and Voytas (2011) *Science* 333:1843-1846.) and that they might vary with context (Stella et al. (2013) *Acta Crystallogr D Biol Crystallogr* 69:1707-1716) In order to characterize this behavior, we used a SELEX assay (as described above) to determine the consensus binding preferences for a large panel of synthetic TALEs designed using the natural code (76 proteins; >250 examples of each RVD).

We then examined these data for RVD:base fidelity. As shown in FIGS. 1 and 6), there was considerable variation in the ability of each RVD to discriminate target sequence. Base compositions selected by "NN", for example, spanned a wide quantitative range, from predominantly adenine to almost exclusively guanine See, e.g., FIG. 1C, underlined RVDs). Likewise, base preferences for the other RVDs also varied. See, e.g., FIG. 6A. Some of this variability can be attributed to identifiable elements of context. For example, the amino terminal repeat frequently selected adenine irrespective of its resident RVD (FIGS. 1C and 1D), whereas NI exhibited a reduced preference for this base in the context of the carboxy-terminal repeat (FIG. 6B). Neighboring bases and repeats substantially influenced the average specificity of NN (FIG. 1E), as well as NI and NG (FIG. 1C and Table 1 below).

TABLE 1

Neighbor influences on RVD specificity

| RVDs: | | NI-NI | | NI-HD | | NI-NN | | NI-NG | |
|---|---|---|---|---|---|---|---|---|---|
| Base Preference: | A | 0.9 | 0.95$^A$ | 0.92 | 0.03 | 0.9 | 0.19 | 0.88 | 0.02 |
| | C | 0.06 | 0.03 | 0.05 | 0.91 | 0.08 | 0.01 | 0.05 | 0.01 |
| | G | 0.04 | 0.01 | 0.03 | 0 | 0.02 | 0.78$^E$ | 0.07 | 0.01 |
| | T | 0.01 | 0 | 0 | 0.06 | 0 | 0.03 | 0 | 0.96$^{K,L,M}$ |
| N: | | 52 | | 65 | | 74 | | 54 | |

| RVDs: | | HD-NI | | HD-HD | | HD-NN | | HD-NG | |
|---|---|---|---|---|---|---|---|---|---|
| Base Preference: | A | 0.02 | 0.86$^A$ | 0.04 | 0.03 | 0.09 | 0.15 | 0.07 | 0.04 |
| | C | 0.95 | 0.11 | 0.95 | 0.96 | 0.91 | 0.05 | 0.92 | 0.05 |
| | G | 0 | 0.02 | 0 | 0 | 0 | 0.78$^F$ | 0 | 0.02 |
| | T | 0.03 | 0 | 0.01 | 0.01 | 0 | 0.02 | 0.01 | 0.89$^K$ |
| N: | | 106 | | 102 | | 15 | | 69 | |

| RVDs: | | NN-NI | | NN-HD | | NN-NN | | NN-NG | |
|---|---|---|---|---|---|---|---|---|---|
| Base Preference: | A | 0.15 | 0.92 | 0.34 | 0.06 | 0.21 | 0.43 | 0.19 | 0.06 |
| | C | 0 | 0.04 | 0.04 | 0.94 | 0.01 | 0.02 | 0.01 | 0.03 |
| | G | 0.85$^B$ | 0.04 | 0.60$^{B,C,D}$ | 0 | 0.77$^C$ | 0.55$^{E,F,G}$ | 0.79$^D$ | 0.01 |
| | T | 0 | 0 | 0.03 | 0 | 0.01 | 0.01 | 0 | 0.90$^L$ |
| N: | | 48 | | 68 | | 54 | | 36 | |

| RVDs: | | NG-NI | | NG-HD | | NG-NN | | NG-NG | |
|---|---|---|---|---|---|---|---|---|---|
| Base Preference: | A | 0.01 | 0.88 | 0.05 | 0.08 | 0.04 | 0.15 | 0.08 | 0.08 |
| | C | 0.01 | 0.02 | 0.06 | 0.92 | 0.02 | 0.02 | 0.06 | 0.06 |
| | G | 0.01 | 0.1 | 0.01 | 0 | 0.01 | 0.83$^G$ | 0.07 | 0.05 |
| | T | 0.96$^{H,I}$ | 0 | 0.89$^H$ | 0.01 | 0.93$^J$ | 0.01 | 0.79$^{I,J}$ | 0.81$^M$ |
| N: | | 36 | | 61 | | 72 | | 62 | |

Average base preferences for every possible two-repeat unit bearing canonical RVDs were calculated. Values were derived from the large scale SELEX study of 76 synthetic TALEs, and were calculated using the base preferences of every non-terminal repeat from that study. Grey highlights RVD:base correspondences from the natural code. "N" indicates the number of instances of the indicated two-repeat unit underlying each preference calculation. A superscript highlights a comparison between a target base preference in two different contexts that exhibits context dependent variation that is both highly significant (p<0.001) and substantial (defined as a change in the aggregate frequency of non-targeted bases of >2-fold or >0.1). F, K, L: p<0.001; all others: p<0.10$^{-5}$. P-values are Mann Whitney U test with FDR correction.

Thus, 6% of queried repeats selected a majority of one or more unintended bases. Moreover a further 7% of repeats exhibited relaxed specificity in that the aggregate preference for the intended base was less than 2:1.

These results demonstrated the limited predictability of TALEs built using only the natural code and underscored the need for additional design options. These results also highlighted sequence features of target sites that would enable optimal recognition by TALEs bearing exclusively canonical RVDs.

Example 3

A Comprehensive Survey of RVD Affinity and Specificity

As the foundation of our efforts to develop new TALE design strategies we first sought to map the base recognition properties of every possible RVD. By so doing, we hoped to identify new candidates for use in design, and to also discern patterns of affinity and specificity that might provide functional insights. To achieve this, each RVD (400 total) was assembled into the fifth repeat of a host TALE protein (Example 1), and then assayed for binding to all four bases at the corresponding sequence position within the host target. Binding studies were performed using a high-throughput ELISA procedure. In choosing this test system, we sought to maximize dynamic range while reducing context effects that might confound analysis. Accordingly we limited the length and affinity of the host TALE (10 repeats) and avoided flanking repeats that appeared likely to interact with the queried RVD based on our analysis of neighbor effects.

The resulting data set (FIG. 2) mapped the relative affinity for every combination of RVD and base (1600 total) onto a scale spanning a 100-fold dynamic range.

In addition, our results were the first comprehensive survey of RVD binding properties, and as such illuminated previously unappreciated features of TALE function. Importantly, they revealed an RVD landscape that was much more crowded with binding-competent residue combinations than might have been expected based on natural RVD frequencies (Cong et al. (2012) Nat Commun 3:968. See, FIG. 2D, in which binding signal is proportional to circle area). Many residue combinations that were rare or absent in nature match the activity and/or specificity of the canonical RVDs (FIG. 2D, boxed circles) suggesting that additional criteria determine natural prevalence.

Our results also illuminated distinct functional roles for each RVD position suggested by recent structural studies. See, e.g., Deng et al. (2012) Science 335:720-723; Mak et al.

(2012) *Science* 335:716-719; Stella et al. (2013) *Acta Crystallogr D Biol Crystallogr* 69:1707-1716. Position 13, for example, largely determined base preference. This was most evident for residues "G", "I", "D" and "N", which specify thymine, adenine, cytosine and guanine/adenine (respectively) throughout each of their respective RVD families (FIG. 2D, columns headed "G", "I", "D" and "N"). Residues "H" and "K" also tend to specify guanine, albeit with generally weaker affinities, while "A" and "P" exhibited a variable preference for thymine. Position 12, in contrast, tended to modulate binding strength, in some cases over a more than 50-fold range of relative ELISA signal, with modest or minimal effects on base preference.

Moreover 75% of the combinations shown in FIG. 2D have not been observed in natural TALEs. Accordingly, these RVDs provide useful alternatives for base recognition in contexts where canonical RVDs are insufficiently specific, including most well-recognized shortcoming of canonical RVDs: the context-dependent inability of NN to resolve G from A.

Overall, these results revealed an RVD landscape populated with residue combinations that exhibit a variety of binding properties that can be applied for designing new TALEs with tailored affinities and/or base preferences.

Example 4

Cellular Activity of Non-Canonical RVDs

Having identified new RVDs with encouraging biochemical properties, we next sought to verify function in a more relevant context for TALE design: a chromosomal locus in a human cell. We pursued this via two complementary studies. In the first, non-canonical RVDs were swapped into key repeats of a previously described TALEN (targeted to the human PitX3 gene, Hockemeyer et al. (2011) *Nat Biotechnol* 29:731-734) in an effort to improve activity and specificity. Substitutions focused on the two least specific guanine-targeted repeats as gauged by SELEX. As shown in FIGS. 3A and 3B, cellular screens identified 3 variants (of 5 tested) that substantially improved gene modification activities (by up to a factor of 2) as well as improved specificities relative to parent. This work verified cellular function of our new RVDs as well as their utility as a local patch for enhancing the binding properties of an otherwise canonical TALE.

Figures 7A, 7B:
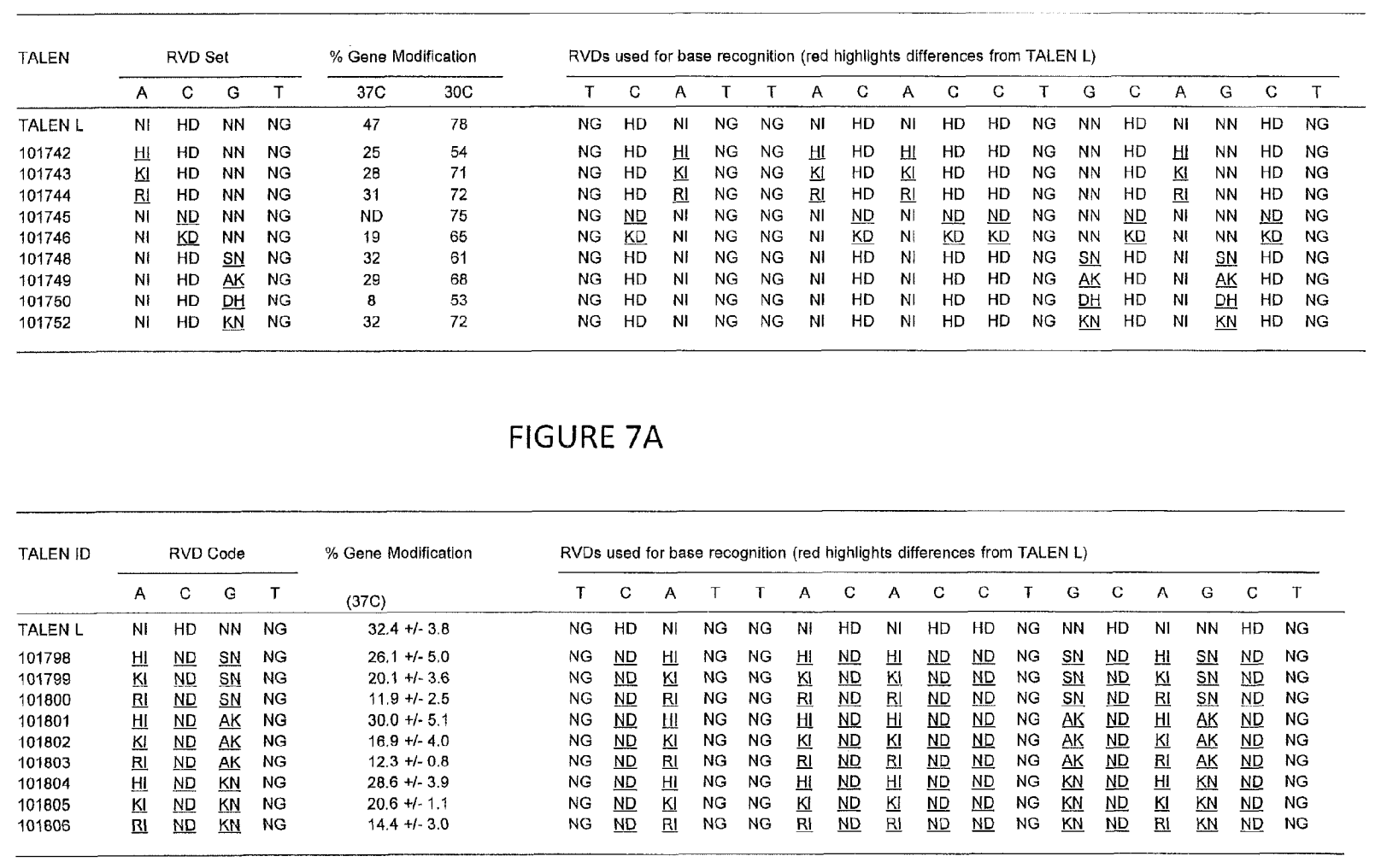

In a second study, we sought to gauge performance of the new RVDs when deployed as a more substantial fraction of a TALE-DNA interface. To this end, we redesigned a previously characterized TALEN using variations of the natural code that employed progressively more non-canonical RVDs, and tested the resultant proteins for cellular function. The host for this effort was the TALEN "L538" (hereafter referred to as "L"), which binds a sequence near the delta-32 locus of human CCR5. See, e.g., Miller et al. (2011) *Nat Biotechnol* 29:143-148. This study identified a diverse set of alternate codes that yield highly active TALENs including several that used exclusively novel RVDs. See, FIG. 7.

These results demonstrate that canonical RVDs, while highly represented in nature, were not obligate components of the TALE-DNA interface and that alternative RVDs could be deployed using code-based rules to generate highly active TALEs.

Example 5

Non-Code-Based Design of TALEs

While an RVD code—natural or otherwise—may provide a straightforward means for designing new TALEs, it will not necessarily yield the most active or specific TALE for a given target. This is because all codes inherently trade design complexity for ease of use, and there is no reason to expect that the best TALE for a target will belong to the minor fraction of possible designs that conform to a simple code. This point is underscored by our initial SELEX studies which revealed non-modular RVD behavior as well as unexpected base preferences in TALEs designed using the natural code. The availability of an expanded set of RVDs provides an opportunity to improve upon simple codes in the design of new TALEs. By using richer arrays of RVDs for target recognition, with choices optimized for context-specific performance, it should be possible to construct TALEs that exhibit improved binding properties relative to their code-derived counterparts.

To address this possibility, we assembled new versions of the "L" TALEN and its partener "R" (referred to as "R557") in a prior study Miller et. al. (ibid) using a more diverse set of RVDs for sequence recognition. We accomplished this via a two-stage process of library assemblies and screens. In the first stage, libraries of TALE tetramers (units comprising four repeats) were constructed and screened for binding to component DNA base quartets from each target (FIG. 4A). In constructing the libraries, we chose RVDs that had performed well in the ELISA studies but deliberately excluded the four canonical RVDs in order to maximize the compositional difference between our new TALENs and the original L/R pair. Tetramers were assembled into the framework of larger host TALEs that enabled screening via ELISA.

The full protein sequence of TALEs targeting the TCAT and CTTC tetramers is summarized below, where underlines highlight invariant RVDs, and the double underlined xx positions highlight RVDs that varied between constructs.

(SEQ ID NO: 58)
MDYKDHDGDYKDHDIDYKDDDDKMAPKKKRKVGIHGVPMVDLRTLGYSQQ

QQEKIKPKVRSTVAQHHEALVGHGFTHAHIVALSQHPAALGTVAVKYQDM

IAALPEATHEAIVGVGKQWSGARALEALLTVAGELRGPPLQLDTGQLLKI

AKRGGVTAVEAVHAWRNALTGAPLNLTPDQVVAIAS<u><u>xx</u></u>GGKQALETVQRL

LPVLCQDHGLTPEQVVAIAS<u><u>xx</u></u>GGKQALETVQRLLPVLCQAHGLTPDQVV

AIAS<u><u>xx</u></u>GGKQALETVQRLLPVLCQAHGLTPAQVVAIAS<u><u>xx</u></u>GGKQALETVQ

RLLPVLCQDHGLTPDQVVAIAS<u>NI</u>GGKQALETVQRLLPVLCQDHGLTPEQ

VVAIAS<u>NG</u>GGKQALETVQRLLPVLCQAHGLTPDQVVAIAS<u>HD</u>GGKQALET

VQRLLPVLCQAHGLTPAQVVAIAS<u>HD</u>GGKQALETVQRLLPVLCQDHGLTP

EQVVAIAS<u>NG</u>GGRPALESIVAQLSRPDPALAALTNDHLVALACLGGRPAL

DAVKKGLPHAPALIKRTNRRIPERTSHRVAGSGYPYDVPDYA

The full sequence of TALEs targeting the tetramers TACA, CCTG, CAGC, CAGA, ATTG and ATAC is summarized as follows. Underlines highlight invariant RVDs, and double underlined xx positions highlight RVDs that varied between constructs.

(SEQ ID NO: 55)
MDYKDHDGDYKDHDIDYKDDDDKMAPKKKRKVGIHGVPMVDLRTLGYSQQ

QQEKIKPKVRSTVAQHHEALVGHGFTHAHIVALSQHPAALGTVAVKYQDM

IAALPEATHEAIVGVGKQWSGARALEALLTVAGELRGPPLQLDTGQLLKI

AKRGGVTAVEAVHAWRNALTGAPLNLTPDQVVAIAS<u>NG</u>GGKQALETVQRL

LPVLCQDHGLTPDQVVAIAN<u>NN</u>GGKQALETVQRLLPVLCQAHGLTPDQVV

AIAS<u>NI</u>GGKQALETVQRLLPVLCQAHGLTPAQVVAIAS<u>HD</u>GGKQALETVQ

RLLPVLCQDHGLTPDQVVAIAS<u>xx</u>GGKQALETVQRLLPVLCQDHGLTPEQ

VVAIAS<u>xx</u>GGKQALETVQRLLPVLCQAHGLTPDQVVAIAS<u>xx</u>GGKQALET

VQRLLPVLCQAHGLTPAQVVAIAS<u>xx</u>GGKQALETVQRLLPVLCQDHGLTP

EQVVAIAS<u>NG</u>GGRPALESIVAQLSRPDPALAALTNDHLVALACLGGRPAL

DAVKKGLPHAPALIKRTNRRIPERTSHRVAGSGYPYDVPDYA

These screens identified dozens of binding-competent tetramers for the targeted quartets that moreover exhibit context-dependent RVD function (FIG. 4D—as shown, depending on the position and adjacent base pairs in the target site, the RVDs exhibited context-dependent binding characteristics). Average normalized DNA-binding score for clones from each of the 8 shotgun libraries is shown in Table 2 below. Each construct was normalized to the cognate control that uses RVDs from the standard code to recognize the 4 base pair subsite:

TABLE 2

Average normalized DNA-binding score for clones from each tetramer shotgun library

| library | N | mean | SE |
|---------|-----|------|------|
| TCAT | 44 | 1.03 | 0.22 |
| TACA | 85 | 0.50 | 0.06 |
| CCTG | 90 | 0.20 | 0.03 |
| CAGC | 137 | 0.03 | 0.02 |
| CTTC | 132 | 0.55 | 0.07 |
| CAGA | 146 | 0.18 | 0.02 |
| ATTG | 131 | 0.37 | 0.05 |
| ATAC | 43 | 0.56 | 0.06 |

Next, successful tetramers were linked into full-length L and R variants and the resulting candidates were screened for gene modification activity in K562 cells (FIG. 4B).

Gene modification activities of TALEN expression constructs screened during development of noncanonical variants of TALEN L and TALEN R are shown below in Tables 3, 4 and 5. To generate these data, each construct was randomly assembled from DNA segments encoding ELISA-validated tetramer repeat units as described above and then cotransfected into K562 cells with the corresponding TALEN R or TALEN L expression construct. Gene modification activity was quantified via deep sequencing.

TALENs were ranked according to activity in two series, corresponding to two distinct screens. RVD compositions of each tetramer and the carboxy terminal half repeat are shown. Tetramers and RVDs are listed in amino→carboxy orientation. The full amino acid sequence of each TALEN can be derived by replacing the xx motifs of the following template sequence shown below with the listed RVDs.

(SEQ ID NO: 56)
MDYKDHDGDYKDHDIDYKDDDDKMAPKKKRKVGIHRGVPMVDLRTLGYSQ

QQQEKIKPKVRSTVAQHHEALVGHGFTHAHIVALSQHPAALGTVAVKYQD

MIAALPEATHEAIVGVGKQWSGARALEALLTVAGELRGPPLQLDTGQLLK

IAKRGGVTAVEAVHAWRNALTGAPLNLTPDQVVAIASxxGGKQALETVQR

LLPVLCQDHGLTPEQVVAIASxxGGKQALETVQRLLPVLCQAHGLTPDQV

VAIASxxGGKQALETVQRLLPVLCQAHGLTPAQVVAIASxxGGKQALETV

QRLLPVLCQDHGLTPDQVVAIASxxGGKQALETVQRLLPVLCQDHGLTPE

QVVAIASxxGGKQALETVQRLLPVLCQAHGLTPDQVVAIASxxGGKQALE

TVQRLLPVLCQAHGLTPAQVVAIASxxGGKQALETVQRLLPVLCQDHGLT

PDQVVAIASxxGGKQALETVQRLLPVLCQDHGLTPEQVVAIASxxGGKQA

LETVQRLLPVLCQAHGLTPDQVVAIASxxGGKQALETVQRLLPVLCQAHG

LTPAQVVAIAxxNGGKQALETVQRLLPVLCQDHGLTPDQVVAIASxxGGK

QALETVQRLLPVLCQDHGLTPEQVVAIASxxGGKQALETVQRLLPVLCQA

HGLTPDQVVAIAxxNGGKQALETVQRLLPVLCQAHGLTPAQVVAIASxxG

GKQALETVQRLLPVLCQDHGLTPEQVVAIASxxGGRPALESIVAQLSRPD

PALAALTNDHLVALACLGGRPALDAVKKGLPHAPALIKRTNRRIPERTSH

RVAGSQLVKSELEEKKSELRHKLKYVPHEYIELIEIARNSTQDRILEMKV

MEFFMKVYGYRGKHLGGSRKPDGAIYTVGSPIDYGVIVDTKAYSGGYNLP

IGQADEMQRYVEENQTRNKHINPNEWWKVYPSSVTEFKFLFVSGHFKGNY

KAQLTRLNHITNCNGAVLSVEELLIGGEMIKAGTLTLEEVRRKFNNGEIN

FRS

TABLE 3

Gene modification by exemplary TALEN L constructs

| Name | tetramer1 | tetramer2 | tetramer3 | tetramer4 | half | % indels |
|------|-----------|-----------|-----------|-----------|------|----------|
| 102046 | HG-RD-HI-HG | VA-CI-ND-HI | KD-KD-QG-HN | RD-HI-HN-ND | HG | 33.6 |
| 102056 | QG-ND-KI-RG | VA-HI-ND-KI | AD-RD-HG-HN | RD-HI-HN-ND | HG | 30.9 |
| 102052 | QG-AD-HI-KG | RG-HI-RD-KI | ND-ND-HG-KN | RD-HI-HN-ND | HG | 30.1 |
| 102083 | QG-ND-KI-RG | VA-CI-ND-HI | ND-KD-HG-HN | KD-HI-CK-ND | HG | 27 |
| 102085 | QG-AD-HI-KG | HG-HI-ND-HI | AD-RD-HG-HN | KD-HI-CK-ND | HG | 26.1 |

TABLE 3-continued

Gene modification by exemplary TALEN L constructs

| Name | tetramer1 | tetramer2 | tetramer3 | tetramer4 | half | % indels |
|---|---|---|---|---|---|---|
| 102049 | QG-AD-HI-KG | RG-HI-RD-KI | KD-KD-QG-HN | RD-HI-HN-ND | HG | 25.9 |
| 102078 | HG-RD-HI-HG | HG-HI-ND-HI | AD-RD-HG-HN | RD-HI-GN-ND | HG | 25.1 |
| 102072 | QG-AD-HI-KG | VA-CI-ND-HI | ND-KD-HG-HN | RD-HI-HN-ND | HG | 24.5 |
| 102077 | HG-RD-HI-HG | RG-HI-RD-KI | ND-ND-HG-KN | RD-HI-HN-ND | HG | 23.8 |
| 102066 | QG-AD-HI-KG | HG-HI-ND-HI | AD-RD-HG-HN | RD-HI-HN-ND | HG | 22.9 |
| 102043 | QG-AD-HI-KG | VA-CI-ND-HI | AD-RD-HG-HN | RD-HI-HN-ND | HG | 22.4 |
| 102076 | QG-AD-HI-KG | RG-HI-RD-KI | AD-RD-HG-HN | KD-HI-CK-ND | HG | 21.6 |
| 102047 | QG-AD-HI-KG | HG-HI-ND-HI | ND-ND-HG-KN | RD-HI-HN-ND | HG | 21.3 |
| 102054 | QG-KD-KI-AA | VA-CI-ND-HI | ND-KD-HG-HN | RD-HI-HN-ND | HG | 21.1 |
| 102050 | QG-AD-HI-KG | VA-HI-ND-KI | AD-RD-HG-HN | RD-HI-HN-ND | HG | 20.4 |
| 102051 | QG-RD-HI-HG | VA-HI-ND-KI | ND-KD-HG-HN | RD-HI-GN-ND | HG | 20.3 |
| 102071 | QG-ND-KI-RG | VA-HI-ND-KI | ND-KD-HG-HN | RD-HI-GN-ND | HG | 19.8 |
| 102079 | HG-RD-HI-HG | VA-CI-ND-HI | ND-KD-HG-HN | RD-HI-HN-ND | HG | 19.6 |
| 102080 | QG-AD-HI-KG | HG-HI-ND-HI | ND-ND-HG-KN | KD-HI-CK-ND | HG | 19.3 |
| 102044 | QG-KD-KI-AA | VA-HI-ND-KI | AD-RD-HG-HN | RD-HI-HN-ND | HG | 19.1 |
| 102070 | QG-KD-KI-AA | HG-HI-ND-HI | ND-ND-HG-KN | KD-HI-CK-ND | HG | 18.3 |
| 102048 | QG-KD-KI-AA | RG-HI-RD-KI | KD-KD-QG-HN | RD-HI-GN-ND | HG | 17.8 |
| 102081 | QG-ND-KI-RG | VA-HI-ND-KI | KD-KD-QG-HN | KD-HI-CK-ND | HG | 17.5 |
| 102067 | QG-ND-KI-RG | VA-HI-ND-KI | KD-KD-QG-HN | RD-HI-GN-ND | HG | 17.2 |
| 102069 | HG-RD-HI-HG | VA-CI-ND-HI | AD-RD-HG-HN | KD-HI-CK-ND | HG | 17.1 |
| 102057 | QG-KD-KI-AA | HG-HI-ND-HI | ND-KD-HG-HN | KD-HI-CK-ND | HG | 16.8 |
| 102084 | QG-KD-KI-AA | RG-HI-RD-KI | AD-RD-HG-HN | RD-HI-GN-ND | HG | 16.8 |
| 102068 | QG-AD-HI-KG | RG-HI-RD-KI | ND-ND-HG-KN | KD-HI-CK-ND | HG | 15.9 |
| 102059 | QG-ND-KI-RG | VA-HI-ND-KI | ND-ND-HG-KN | RD-HI-HN-ND | HG | 14.8 |
| 102061 | QG-ND-KI-RG | VA-HI-ND-KI | AD-RD-HG-HN | RD-HI-GN-ND | HG | 13.4 |
| 102073 | QG-KD-KI-AA | VA-HI-ND-KI | KD-KD-QG-HN | KD-HI-CK-ND | HG | 12.8 |
| 102065 | QG-AD-HI-KG | VA-CI-ND-HI | ND-ND-HG-KN | RD-HI-HN-ND | HG | 12.7 |
| 102075 | HG-RD-HI-HG | HG-HI-ND-HI | AD-RD-HG-HN | RD-HI-HN-ND | HG | 10.7 |
| 102053 | QG-ND-KI-RG | RG-HI-RD-KI | ND-KD-HG-HN | RD-HI-HN-ND | HG | 0 |
| 102062 | QG-KD-KI-AA | RG-HI-RD-KI | KD-KD-QG-HN | RD-HI-GN-ND | HG | 0 |
| 102082 | QG-KD-KI-AA | HG-HI-ND-HI | AD-RD-HG-HN | KD-HI-CK-ND | HG | 0 |
| 102002 | QG-AD-HI-KG | VA-HI-RD-HI | KD-KD-RG-CN | RD-HI-CN-RD | KG | 20.3 |
| 102010 | QG-KD-KI-AA | VA-HI-RD-HI | KD-KD-RG-CN | KD-HI-CN-KD | KG | 17.3 |
| 102038 | QG-KD-KI-AA | KG-HI-KD-HI | KD-KD-KG-CN | KD-HI-AN-RD | KG | 17.2 |
| 102035 | QG-KD-KI-AA | VA-HI-RD-HI | KD-KD-KG-CN | KD-HI-CN-KD | KG | 16.8 |
| 102004 | QG-KD-KI-AA | KG-HI-KD-HI | KD-KD-RG-CN | KD-HI-AN-RD | KG | 16.4 |
| 102024 | QG-KD-KI-AA | KG-HI-KD-HI | KD-KD-KG-FN | RD-HI-CN-RD | KG | 15.7 |
| 102012 | QG-RD-HI-QG | VA-HI-RD-HI | KD-KD-KG-CN | KD-HI-AN-RD | KG | 15.5 |
| 102011 | KG-KD-KI-VA | VA-HI-RD-HI | KD-KD-KG-CN | KD-HI-AN-RD | KG | 14 |
| 102009 | QG-RD-HI-QG | VA-HI-RD-HI | KD-KD-KG-CN | KD-HI-CN-KD | KG | 13.7 |
| 102037 | QG-RD-HI-QG | KG-HI-KD-HI | AD-KD-RG-CN | RD-HI-CN-RD | KG | 13.2 |
| 102022 | QG-RD-HI-QG | KG-HI-KD-HI | KD-KD-RG-CN | RD-HI-CN-RD | KG | 12.9 |
| 102042 | QG-RD-HI-QG | AA-HI-RD-KI | KD-KD-RG-CN | KD-HI-AN-RD | KG | 12.6 |
| 102030 | QG-KD-KI-AA | AA-HI-RD-KI | KD-KD-KG-CN | RD-HI-CN-KD | KG | 12.3 |
| 102031 | QG-RD-HI-QG | RG-HI-RD-KI | KD-KD-RG-CN | KD-HI-CN-KD | KG | 12 |
| 102028 | QG-KD-KI-AA | VA-HI-RD-HI | KD-KD-RG-CN | RD-HI-CN-KD | KG | 11.9 |
| 102005 | QG-AD-HI-KG | VA-HI-RD-HI | KD-KD-KG-FN | RD-HI-CN-KD | KG | 11.6 |
| 102034 | QG-KD-KI-AA | VA-HI-RD-HI | KD-KD-KG-CN | RD-HI-CN-KD | KG | 10.8 |
| 102033 | QG-KD-KI-AA | KG-HI-KD-HI | KD-KD-KG-FN | KD-HI-CN-KD | KG | 10.7 |
| 102018 | KG-KD-KI-VA | VA-HI-RD-HI | KD-KD-RG-CN | KD-HI-AN-RD | KG | 10.6 |
| 102019 | KG-KD-KI-VA | RG-HI-RD-KI | KD-KD-RG-CN | RD-HI-CN-RD | KG | 10.3 |
| 102039 | KG-KD-KI-VA | KG-HI-KD-HI | KD-KD-KG-FN | KD-HI-CN-KD | KG | 10 |
| 102001 | KG-KD-KI-VA | KG-HI-KD-HI | KD-KD-RG-CN | KD-HI-AN-RD | KG | 9.3 |
| 102014 | QG-KD-KI-AA | RG-HI-RD-KI | KD-KD-KG-FN | RD-HI-CN-KD | KG | 9 |
| 102017 | QG-KD-KI-AA | VA-HI-RD-HI | AD-KD-RG-CN | KD-HI-CN-KD | KG | 8.7 |
| 102008 | QG-KD-KI-AA | RG-HI-RD-KI | KD-KD-KG-FN | KD-HI-CN-KD | KG | 7 |
| 102025 | KG-KD-KI-VA | VA-HI-RD-HI | KD-KD-KG-FN | RD-HI-CN-RD | KG | 6.7 |
| 102013 | QG-RD-HI-QG | AA-HI-RD-KI | AD-KD-RG-CN | KD-HI-CN-KD | KG | 6.5 |
| 102041 | QG-RD-HI-QG | RG-HI-RD-KI | KD-KD-KG-FN | RD-HI-CN-KD | KG | 4.2 |
| 102006 | QG-AD-HI-KG | VA-HI-RD-HI | AD-RD-RG-CN | KD-HI-CN-KD | KG | 1.3 |
| 102016 | KG-KD-KI-VA | RG-HI-RD-KI | AD-RD-RG-CN | RD-HI-CN-RD | KG | 0 |
| 102026 | KG-KD-KI-VA | VA-HI-RD-HI | AD-KD-RG-CN | KD-HI-AN-RD | KG | 0 |
| 102027 | KG-KD-KI-VA | AA-HI-RD-KI | AD-KD-RG-CN | KD-HI-CN-KD | KG | 0 |
| 102029 | KG-KD-KI-VA | AA-HI-RD-KI | AD-KD-RG-CN | KD-HI-CN-KD | KG | 0 |
| 102032 | QG-AD-HI-KG | VA-HI-RD-HI | KD-KD-KG-CN | RD-HI-CN-RD | KG | 0 |
| 102040 | KG-KD-KI-VA | KG-HI-KD-HI | KD-KD-KG-FN | KD-HI-AN-RD | KG | 0 |

Additional, variants of TALEN 102046 (shown in Table 3 above) were generated via substitution of the indicated tetramers or the 17th half repeat and then cotransfected into K562 cells with a TALEN R expression construct. Gene modification activity was then quantified via deep sequencing.

RVD compositions of each tetramer and the carboxy terminal half repeat are shown below in Table 4. Tetramers and RVDs are listed in amino→carboxy orientation. Substitutions relative to 102046 are underlined. The full amino acid sequence of each TALEN can be derived by replacing motifs of the template sequence provided in SEQ ID NO:56 with the listed RVDs.

TABLE 4

Gene modification by exemplary TALEN L constructs

| Name | tetramer1 | tetramer2 | tetramer3 | tetramer4 | half | % indels |
|---|---|---|---|---|---|---|
| 102202 | QG-AD-HI-KG | VA-CI-ND-HI | KD-KD-QG-HN | RD-HI-HN-ND | HG | 32.4 |
| 102203 | QG-KD-KI-AA | VA-CI-ND-HI | KD-KD-QG-HN | RD-HI-HN-ND | HG | 16.6 |
| 102204 | QG-ND-HI-KG | VA-CI-ND-HI | KD-KD-QG-HN | RD-HI-HN-ND | HG | 36.6 |
| 102205 | QG-ND-KI-RG | VA-CI-ND-HI | KD-KD-QG-HN | RD-HI-HN-ND | HG | 40.2 |
| 102206 | RG-ND-KI-QA | VA-CI-ND-HI | KD-KD-QG-HN | RD-HI-HN-ND | HG | 23.5 |
| 102208 | HG-RD-HI-HG | HG-HI-ND-HI | KD-KD-QG-HN | RD-HI-HN-ND | HG | 27.9 |
| 102209 | HG-RD-HI-HG | KG-HI-ND-HI | KD-KD-QG-HN | RD-HI-HN-ND | HG | 28.4 |
| 102210 | HG-RD-HI-HG | RG-CI-ND-HI | KD-KD-QG-HN | RD-HI-HN-ND | HG | 33.6 |
| 102211 | HG-RD-HI-HG | VA-HI-RD-HI | KD-KD-QG-HN | RD-HI-HN-ND | HG | 23.2 |
| 102213 | HG-RD-HI-HG | VA-CI-ND-HI | AD-KD-BG-CN | RD-HI-HN-ND | HG | 34.1 |
| 102214 | HG-RD-HI-HG | VA-CI-ND-HI | AD-RD-HG-HN | RD-HI-HN-ND | HG | 31.2 |
| 102215 | HG-RD-HI-HG | VA-CI-ND-HI | ND-KD-HG-HN | RD-HI-HN-ND | HG | 29.0 |
| 102216 | HG-RD-HI-HG | VA-CI-ND-HI | RD-HI-HN-ND | RD-HI-HN-ND | HG | 35.4 |
| 102217 | HG-RD-HI-HG | VA-CI-ND-HI | ND-ND-QA-HN | RD-HI-HN-ND | HG | 34.5 |
| 102219 | HG-RD-HI-HG | VA-CI-ND-HI | KD-KD-QG-HN | KD-HI-AN-RD | HG | 37.8 |
| 102224 | HG-RD-HI-HG | VA-CI-ND-HI | KD-KD-QG-HN | RD-HI-HN-ND | NG | 38.7 |
| 102046 | HG-RD-HI-HG | VA-CI-ND-HI | KD-KD-QG-HN | RD-HI-HN-ND | HG | 30.1 |

Table 5 shows gene modification results, as quantified via deep sequencing, by exemplary TALEN R expression constructs transfected into K562 cells. Gene modification activity was quantified via deep sequencing. TALENs were ranked according to activity in two series, corresponding to two distinct screens. RVD compositions of each tetramer and the carboxy terminal half repeat are shown. Tetramers and RVDs are listed in amino→carboxy orientation. The full amino acid sequence of each TALEN can be derived by replacing ▓ motifs of the template sequence provided in SEQ ID NO:56 with the listed RVDs. Two TALENs bear an additional amino acid substitution relative to the template, specifically G34R in their eighth repeat. These are highlighted with an asterisk.

TABLE 5

Gene modification by exemplary TALEN R constructs

| Name | tetramer1 | tetramer2 | tetramer3 | tetramer4 | half | % indels |
|---|---|---|---|---|---|---|
| 102148 | ND-HG-RG-ND | ND-HI-HN-KI | CI-MG-KG-HN | CI-VA-HI-ND | HG | 33.7 |
| 102146 | RD-HG-KG-ND | ND-HI-HN-KI | CI-HG-HG-CN | CI-KG-HI-AD | HG | 31.4 |
| 102150 | ND-HG-RG-ND | KD-HI-HN-KI | HI-AA-VA-HN | KI-HG-HI-ND | HG | 31.2 |
| 102156 | ND-HG-RG-ND | KD-HI-KN-CI | CI-MG-KG-HN | CI-KG-HI-AD | HG | 25.4 |
| 102159 | ND-HG-RG-ND | ND-HI-HN-KI | HI-AA-VA-HN | HI-VA-CI-ND | HG | 24.9 |
| 102151 | ND-HG-RG-ND | KD-HI-KN-CI | CI-HG-HG-CN | CI-VA-HI-ND | HG | 23.6 |
| 102158 | RD-HG-KG-ND | ND-HI-HN-KI | CI-HG-HG-CN | HI-VA-CI-ND | HG | 23.4 |
| 102162 | ND-HG-RG-ND | KD-HI-FN-HI | CI-HG-HG-CN | KI-HG-HI-ND | HG | 23.1 |
| 102177 | RD-HG-KN-ND | KD-HI-KN-CI | KI-HG-QA-HN | KI-HG-HI-ND | HG | 22.9 |
| 102173 | RD-RG-KG-AD | KD-HI-FN-HI | CI-MG-KG-HN | HI-VA-CI-ND | HG | 22.5 |
| 102149 | RD-RG-RG-KD | ND-HI-HN-KI | HI-AA-VA-HN | KI-HG-HI-ND | HG | 22.2 |
| 102187 | RD-RG-RG-KD | KD-HI-FN-HI | CI-MG-KG-HN | KI-HG-HI-ND | HG | 22.2 |
| 102172 | RD-RG-KG-AD | KD-HI-FN-HI | CI-MG-KG-HN | HI-VA-CI-ND | HG | 21.8 |
| 102183 | RD-HG-KG-ND | KD-HI-FN-HI | CI-HG-HG-CN | CI-VA-HI-ND | HG | 21.5 |
| 102179 | RD-HG-KG-ND | KD-HI-KN-CI | KI-HG-QA-HN | CI-VA-HI-ND | HG | 21.1 |
| 102180 | RD-RG-KG-AD | KD-HI-KN-CI | KI-HG-QA-HN | KI-HG-HI-ND | HG | 21.1 |
| 102167 | RD-HG-KG-ND | ND-HI-HN-KI | HI-AA-VA-HN | HI-VA-CI-ND | HG | 20.5 |
| 102178 | RD-HG-KG-ND | KD-HI-FN-HI | KI-HG-QA-HN | CI-KG-HI-AD | HG | 19.6 |
| 102145 | RD-HG-KG-ND | KD-HI-HN-KI | CI-HG-HG-CN | CI-KG-HI-AD | HG | 19.6 |
| 102166 | RD-RG-KG-AD | KD-HI-FN-HI | CI-HG-HG-CN | KI-HG-HI-ND | HG | 19.5 |
| 102152 | RD-HG-KG-ND | KD-HI-FN-HI | KI-HG-QA-HN | CI-VA-HI-ND | HG | 18.5 |
| 102153 | ND-HG-RG-ND | KD-HI-FN-HI | KI-HG-QA-HN | HI-VA-CI-ND | HG | 18.3 |
| 102157 | RD-HG-KG-ND | KD-HI-FN-HI | HI-AA-VA-HN | HI-VA-CI-ND | HG | 18.1 |
| 102181 | RD-RG-RG-KD | ND-HI-HN-KI | CI-MG-KG-HN | HI-VA-CI-ND | HG | 17.7 |
| 102147 | RD-RG-KG-AD | KD-HI-KN-CI | CI-MG-KG-HN | KI-HG-HI-ND | HG | 17.1 |
| 102188 | RD-RG-KG-AD | KD-HI-KN-CI | CI-MG-KG-HN | HI-VA-CI-ND | HG | 16.3 |
| 102174 | RD-RG-RG-KD | ND-HI-HN-KI | HI-AA-VA-HN | CI-VA-HI-ND | HG | 15.8 |
| 102143 | RD-RG-RG-KD | KD-HI-KN-CI | CI-HG-HG-CN | CI-VA-HI-ND | HG | 15.5 |
| 102160 | ND-HG-RG-ND | KD-HI-KN-CI | CI-MG-KG-HN | HI-VA-CI-ND | HG | 15.4 |
| 102182 | RD-RG-KG-AD | KD-HI-HN-KI | KI-HG-QA-HN | CI-VA-HI-ND | HG | 14.6 |
| 102175 | RD-RG-RG-KD | KD-HI-HN-KI | HI-AA-VA-HN | KI-HG-HI-ND | HG | 13.9 |
| 102163 | ND-HG-RG-ND | KD-HI-FN-HI | KI-HG-QA-HN | CI-VA-HI-ND | HG | 12.9 |
| 102176 | RD-RG-RG-KD | KD-HI-HN-KI | HI-AA-VA-HN | HI-VA-CI-ND | HG | 12.8 |
| 102165 | RD-RG-RG-KD | KD-HI-KN-CI | HI-AA-VA-HN | HI-VA-CI-ND | HG | 11.9 |
| 102186 | RD-RG-RG-KD | KD-HI-HN-KI | KI-HG-QA-HN | CI-KG-HI-AD | HG | 11.6 |
| 102185 | RD-HG-KG-ND | KD-HI-HN-KI | CI-HG-HG-CN | CI-KG-HI-AD | HG | 9.9 |
| 102144 | RD-RG-RG-KD | ND-HI-HN-KI | CI-HG-HG-CN | CI-KG-HI-AD | HG | 9.7 |
| 102161 | RD-RG-RG-KD | KD-HI-FN-HI | CI-MG-KG-HN | CI-KG-HI-AD | HG | 9.3 |
| 102164 | RD-RG-KG-AD | KD-HI-HN-KI | CI-HG-HG-CN | KI-HG-HI-ND | HG | 0.0 |
| 102123 | RD-RG-KG-AD | KD-HI-AN-KI | KI-KG-MG-AN | KI-RG-CI-KD | KG | 32.8 |

TABLE 5-continued

Gene modification by exemplary TALEN R constructs

| Name | tetramer1 | tetramer2 | tetramer3 | tetramer4 | half | % indels |
|---|---|---|---|---|---|---|
| 102109* | RD-AA-QG-AD | KD-HI-AN-KI | KI-RG-RG-FN | CI-KG-HI-AD | KG | 29.7 |
| 102124 | RD-VA-RG-RD | KD-HI-AN-CI | KI-RG-RG-FN | CI-KG-HI-AD | KG | 29.1 |
| 102102 | RD-VA-RG-RD | KD-HI-AN-CI | KI-RG-RG-FN | CI-KG-HI-RD | KG | 27.8 |
| 102115 | RD-VA-RG-RD | KD-HI-FN-HI | KI-RG-QG-AN | HI-KG-HI-KD | KG | 27.7 |
| 102105 | RD-AA-QG-AD | KD-HI-FN-HI | KI-RG-RG-FN | KI-RG-CI-KD | KG | 24.9 |
| 102126 | RD-RG-RG-KD | KD-HI-FN-HI | KI-RG-QG-AN | HI-KG-HI-KD | KG | 24.6 |
| 102113 | RD-AA-QG-AD | KD-HI-AN-CI | KI-RG-RG-FN | CI-KG-HI-AD | KG | 24.4 |
| 102114 | RD-VA-RG-RD | KD-HI-FN-HI | KI-KG-MG-AN | HI-KG-HI-KD | KG | 22.8 |
| 102138* | RD-AA-QG-AD | KD-HI-AN-KI | KI-KG-MG-AN | HI-KG-HI-KD | KG | 22.7 |
| 102103 | RD-RG-KG-AD | KD-HI-FN-HI | KI-KG-MG-AN | CI-KG-HI-RD | KG | 22.0 |
| 102107 | RD-RG-KG-AD | KD-HI-AN-KI | KI-RG-QG-AN | KI-RG-CI-KD | KG | 21.4 |
| 102104 | RD-RG-RG-KD | KD-HI-AN-KI | KI-RG-QG-AN | CI-KG-HI-AD | KG | 20.1 |
| 102137 | RD-VA-RG-RD | KD-HI-AN-KI | KI-RG-RG-FN | KI-RG-CI-KD | KG | 19.8 |
| 102142 | RD-RG-KG-AD | KD-HI-AN-CI | KI-KG-MG-AN | CI-KG-HI-AD | KG | 19.7 |
| 102101 | RD-AA-QG-AD | KD-HI-FN-HI | KI-KG-MG-AN | KI-RG-CI-KD | KG | 19.6 |
| 102120 | RD-AA-QG-AD | KD-HI-AN-CI | KI-RG-QG-AN | CI-KG-HI-RD | KG | 19.2 |
| 102132 | RD-VA-RG-RD | KD-HI-AN-CI | KI-KG-MG-AN | HI-KG-HI-KD | KG | 19.0 |
| 102117 | RD-RG-RG-KD | KD-HI-AN-CI | KI-RG-RG-FN | CI-KG-HI-AD | KG | 18.8 |
| 102116 | RD-RG-RG-KD | KD-HI-FN-HI | KI-RG-RG-FN | CI-KG-HI-RD | KG | 18.5 |
| 102141 | RD-VA-RG-RD | KD-HI-AN-CI | KI-RG-RG-FN | KI-RG-CI-KD | KG | 18.3 |
| 102121 | RD-AA-QG-AD | KD-HI-AN-CI | KI-RG-RG-FN | KI-RG-CI-KD | KG | 18.1 |
| 102125 | RD-VA-RG-RD | KD-HI-AN-CI | HI-KG-VA-AK | KI-RG-CI-KD | KG | 18.0 |
| 102140 | RD-RG-RG-KD | KD-HI-AN-CI | KI-RG-QG-AN | CI-KG-HI-RD | KG | 17.6 |
| 102122 | RD-RG-KG-AD | KD-HI-AN-CI | KI-RG-RG-FN | CI-KG-HI-RD | KG | 17.5 |
| 102134 | RD-RG-RG-KD | KD-HI-FN-HI | KI-KG-MG-AN | KI-RG-CI-KD | KG | 16.0 |
| 102136 | RD-AA-QG-AD | KD-HI-AN-CI | KI-KG-MG-AN | KI-RG-CI-KD | KG | 15.4 |
| 102139 | RD-VA-RG-RD | KD-HI-AN-KI | KI-KG-MG-AN | CI-KG-HI-AD | KG | 15.4 |
| 102111 | RD-RG-KG-AD | KD-HI-AN-KI | KI-RG-RG-FN | KI-RG-CI-KD | KG | 14.6 |
| 102131 | RD-VA-RG-RD | KD-HI-FN-HI | KI-RG-QG-AN | CI-KG-HI-AD | KG | 14.5 |
| 102119 | RD-VA-RG-RD | KD-HI-AN-CI | HI-KG-VA-AK | KI-RG-CI-KD | KG | 14.0 |
| 102110 | RD-RG-KG-AD | KD-HI-FN-HI | KI-RG-RG-FN | CI-KG-HI-AD | KG | 13.6 |
| 102130 | RD-RG-RG-KD | KD-HI-AN-KI | KI-RG-RG-FN | HI-KG-HI-KD | KG | 11.5 |
| 102133 | RD-VA-RG-RD | KD-HI-AN-KI | HI-KG-VA-AK | CI-KG-HI-AD | KG | 10.8 |
| 102127 | RD-AA-QG-AD | KD-HI-AN-CI | HI-KG-VA-AK | CI-KG-HI-RD | KG | 8.0 |
| 102128 | RD-VA-RG-RD | KD-HI-AN-KI | HI-KG-VA-AK | KI-RG-CI-KD | KG | 7.6 |
| 102118 | RD-VA-RG-RD | KD-HI-FN-HI | HI-KG-VA-AK | KI-RG-CI-KD | KG | 6.9 |
| 102112 | RD-RG-RG-KD | KD-HI-FN-HI | KI-KG-MG-AN | CI-KG-HI-RD | KG | 6.1 |
| 102129 | RD-VA-RG-RD | KD-HI-AN-CI | KI-RG-QG-AN | CI-KG-HI-AD | KG | 4.7 |
| 102108 | RD-RG-RG-KD | KD-HI-AN-KI | KI-KG-MG-AN | CI-KG-HI-RD | KG | 0.0 |

This effort identified two novel TALENs (referred to as "L*" and "R*"; FIG. 4B-C) that induce high levels of target modification (FIG. 4E) and that collectively recognize DNA using a set of 16 distinct non-canonical RVDs.

We then evaluated the cellular specificity of these new TALENs and their canonical parents via deep sequencing of 23 candidate off-target sites from K562 cells exposed to L*/R* or L/R. Properties of these 23 candidate off-target (OT) sites are shown in Table 6 below and the % indels induced by the different constructs at each of these sites are shown in Table 7 below:

TABLE 6

Characteristics of off-target loci

| locus | coordinates | gene | mismatch | type | spacer (bp) |
|---|---|---|---|---|---|
| CCR5 | chr3 46414913 | CCR5 | 0 | LR | 18 |
| OT1 | chr12 1809633 | ADIPOR2 | 8 | RL | 19 |
| OT2 | chr17 62935934 | | 8 | LL | 22 |
| OT3 | chr17 62800602 | PLEKHM1P^ | 8 | LL | 22 |
| OT4 | chr17 43535189 | PLEKHM1 | 8 | LL | 22 |
| OT5 | chr8 32812474 | | 8 | LL | 20 |
| OT6 | chrX 18391882 | | 8 | RR | 14 |
| OT7 | chr8 19021419 | | 8 | RR | 21 |
| OT8 | chr11 61216536 | | 8 | LL | 18 |
| OT9 | chr7 80598455 | | 8 | RR | 23 |
| OT10 | chr11 50734723 | | 8 | RR | 23 |
| OT11 | chr4 11272080 | | 8 | LR | 17 |
| OT12 | chr4 170741272 | | 8 | LL | 10 |
| OT13 | chr3 182808963 | MCCC1 | 8 | RL | 14 |
| OT14 | chr19 3205606 | NCLN | 7 | RR | 21 |
| OT15 | chr8 58466850 | | 8 | RL | 20 |
| OT16 | chr2 157803806 | | 8 | RL | 21 |
| OT17 | chr18 36664563 | | 8 | LR | 24 |
| OT18 | chr6 45459930 | RUNX2 | 8 | LR | 20 |
| OT19 | chr7 87334898 | ABCB1 | 8 | LL | 12 |
| OT20 | chr20 4746578 | | 8 | LL | 13 |
| OT21 | chr8 59307544 | | 8 | LL | 11 |
| OT22 | chr9 9767785 | PTPRD | 8 | RR | 13 |
| OT23 | chr19 24130374 | LTR^ | 8 | RL | 23 |

^OT3 targets a pseudo gene homologous to PLEKHM1. OT23 targets a HERV17-int LTR

TABLE 7

Cleavage at off-target loci

| Locus | L/R % indels | L/R* % indels | L*/R % indels | L*/R* % indels |
|---|---|---|---|---|
| CCR5 | 50.65 | 55.53 | 58.66 | 65.23 |
| OT1 | 3.175 | 0.663 | 1.967 | 0.32 |
| OT2 | 3.181 | 3.541 | 0.022 | 0.017 |

TABLE 7-continued

Cleavage at off-target loci

| Locus | L/R % indels | L/R* % indels | L*/R % indels | L*/R* % indels |
|---|---|---|---|---|
| OT3 | 1.053 | 1.466 | 0.003 | 0.005 |
| OT4 | 0.817 | 1.184 | 0.005 | 0.005 |
| OT5 | 0.806 | 0.874 | 0.028 | 0.011 |
| OT6 | 0.629 | 0.007 | 0.764 | 0.024 |
| OT7 | 0.462 | 0.044 | 0.591 | 0.048 |
| OT8 | 0.665 | 0.624 | 0.126 | 0.045 |
| OT9 | 0.182 | 0.051 | 0.124 | 0 |
| OT10 | 0.16 | 0 | 0.107 | 0.016 |
| OT11 | 0.082 | 0.004 | 0.057 | 0.001 |
| OT12 | 0.039 | 0.033 | 0 | 0 |
| OT13 | 0.029 | 0.054 | 0.047 | 0.055 |
| OT14 | 0.066 | 0.019 | 0 | 0 |
| OT15 | 0 | 0.003 | 0.003 | 0 |
| OT16 | 0.016 | 0.022 | 0.007 | 0.004 |
| OT17 | 0.019 | 0.02 | 0.018 | 0.03 |
| OT18 | 0 | 0 | 0.003 | 0 |
| OT19 | 0 | 0.006 | 0 | 0 |
| OT20 | 0.024 | 0.006 | 0.006 | 0.009 |
| OT21 | 0 | 0.013 | 0.006 | 0 |
| OT22 | 0 | 0.018 | 0 | 0.005 |
| OT23 | 0 | 0.003 | 0.003 | 0.01 |

Figure 5E:
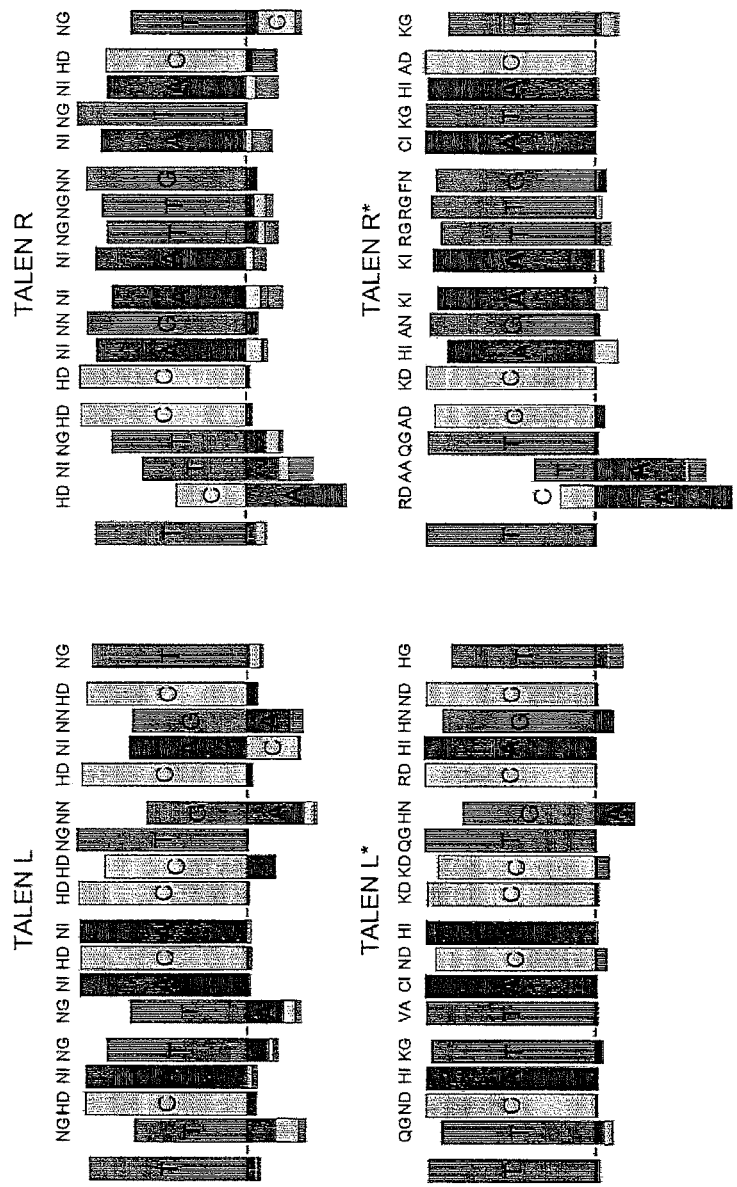

This study included a post-transfection cold shock (U.S. Pat. No. 8,772,008) in order to drive higher levels of cleavage for analysis. Under these conditions both nuclease pairs modified CCR5 to similarly high levels (FIG. 5A). However the new TALENs manifested substantially reduced off-target cleavage (FIGS. 5B and 5C), with aggregate levels of off-target cleavage reduced by a factor of 17. While the canonical L/R pair detectably modified 13 off-target loci with an aggregate frequency of 11%, the new L*/R* TALENs modified fewer loci (no more than seven) with an aggregate frequency of 0.55%. Individual loci exhibited up to 180-fold reduced cleavage by L*/R* (FIG. 5B, OT2). Moreover, mixed dimers (L/R* and L*/R) yielded intermediate behaviors (FIG. 5D) indicating that both L* and R* contributed to the reduction in off-target cleavage.

Finally, as an additional test of specificity all TALENs were submitted for SELEX analysis. This assay revealed specific binding for all four proteins, but with L* and R* exhibiting an improved aggregate percent match to their intended targets Importantly, these results (FIG. 5E) were achieved despite deliberate exclusion of canonical RVDs as well as substantial under sampling of the diversity of TALE candidates.

Insights from this and previous examples include the information displayed in Table 8 for a subset of non-canonical RVDs. This information is useful for designing TALEs with improved binding and/or specificity relative to their canonical counterparts.

TABLE 8

Summary of TALE design enhancements

| Target Base | RVDs exhibiting enhanced properties |
|---|---|
| guanine | $GN^b$, $SN^b$, $VN^b$, $LN^b$, $DN^b$, $QN^b$, $EN^b$, $HN^{c,d}$, $RH^{b,c}$, $NK^{b,c}$ $AN^{a,d}$ |
| thymine | $VG^b$, $IG^b$, $EG^b$, $MG^b$, $YG^b$, $HG^b$, $EP^b$, $VA^a$, $QG^d$, $KG^d$, $RG^d$ |

TABLE 8-continued

Summary of TALE design enhancements

| Target Base | RVDs exhibiting enhanced properties |
|---|---|
| adenine | $CI^d$, $HI^d$, $KI^d$ |
| cytosine | $RD^d$, $KD^d$, $ND^{b,d}$, $AD^{b,d}$ |

[a]ELISA study indicated enhanced affinity
[b]ELISA study indicated enhanced target base preference
[c]PitX study showed enhanced target preference and cellular activity
[d]CCR5 study showed enhanced cellular specificity and SELEX consensus These studies underscore the capabilities of our new RVDs and also demonstrate their potential for enabling improved TALE function via the use of more complex designs.

Example 6

Activity and Specificity of the L and L* TALEN Designs in Combination with the "+17" C-Cap The development of improved TALENs should benefit from combining RVD substitutions with other, mechanistically distinct strategies for enhancing performance. As a test of this possibility, we sought to deploy our new RVDs in the context of a TALEN architecture bearing a shorter C-terminal region. C-terminal truncations can improve gene editing activity and increase cleavage specificity for a more limited range of dimer configurations. For this study we reduced the C-terminal region to 17 residues (a "+17 C-cap"), since this length supported peak activity in a prior truncation scan. Accordingly, we combined the L* and L repeat arrays with the "+17" architecture and then tested the resulting TALENs ("L+*17" and "L+17") for cellular activity and specificity when paired with a partner (R2+17) that enables maximal activity.

Figure 8A:
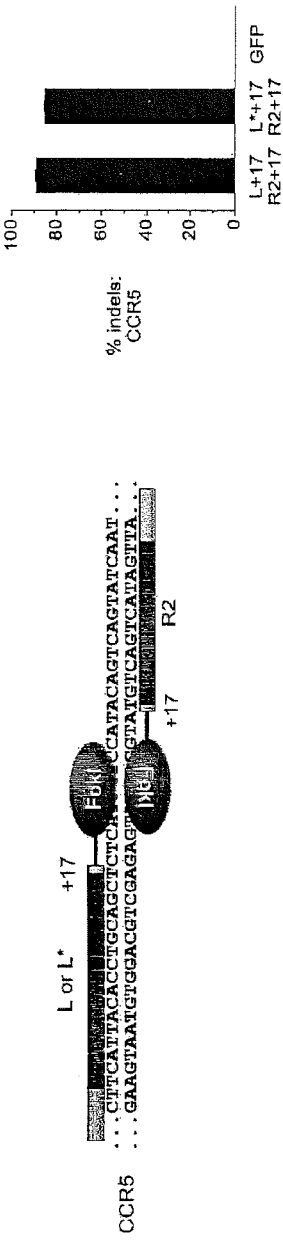
FIGS. 8A and 8B depict exemplary TALENs described herein.
Figure 8B:
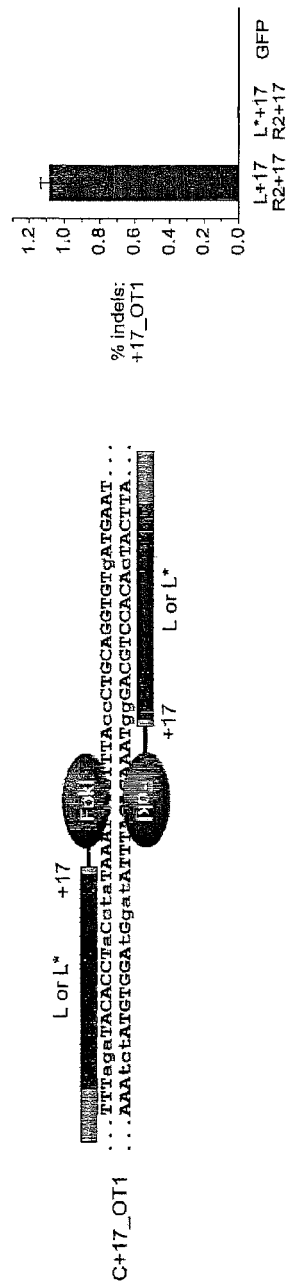

As shown in FIG. 8, we observed that L*+17 exhibited comparable levels of on-target activity to L+17 (>85% indels), but with a >100 fold reduction in cleavage at the sole active L+17 off-target site.

This study underscores the potential for combining new RVDs with other strategies to improve TALEN performance.

Example 7

Activity and Specificity of the L, R, L* and R* TALEN Designs in Combination with the Q3 Mutations A second, mechanistically distinct strategy for enhancing the specificity of TALENs was described by Guilinger et al. (2014) Nat Methods 11(4):429-35 and involves mutating certain positively charged residues in the C-cap. In this study, we compared the performance of our non-canonical RVD TALENs L* and R* to canonical RVD TALENs bearing the mutations described in the "Q3" mutants in Guilinger et al., infra.

Figures 9A, 9B:
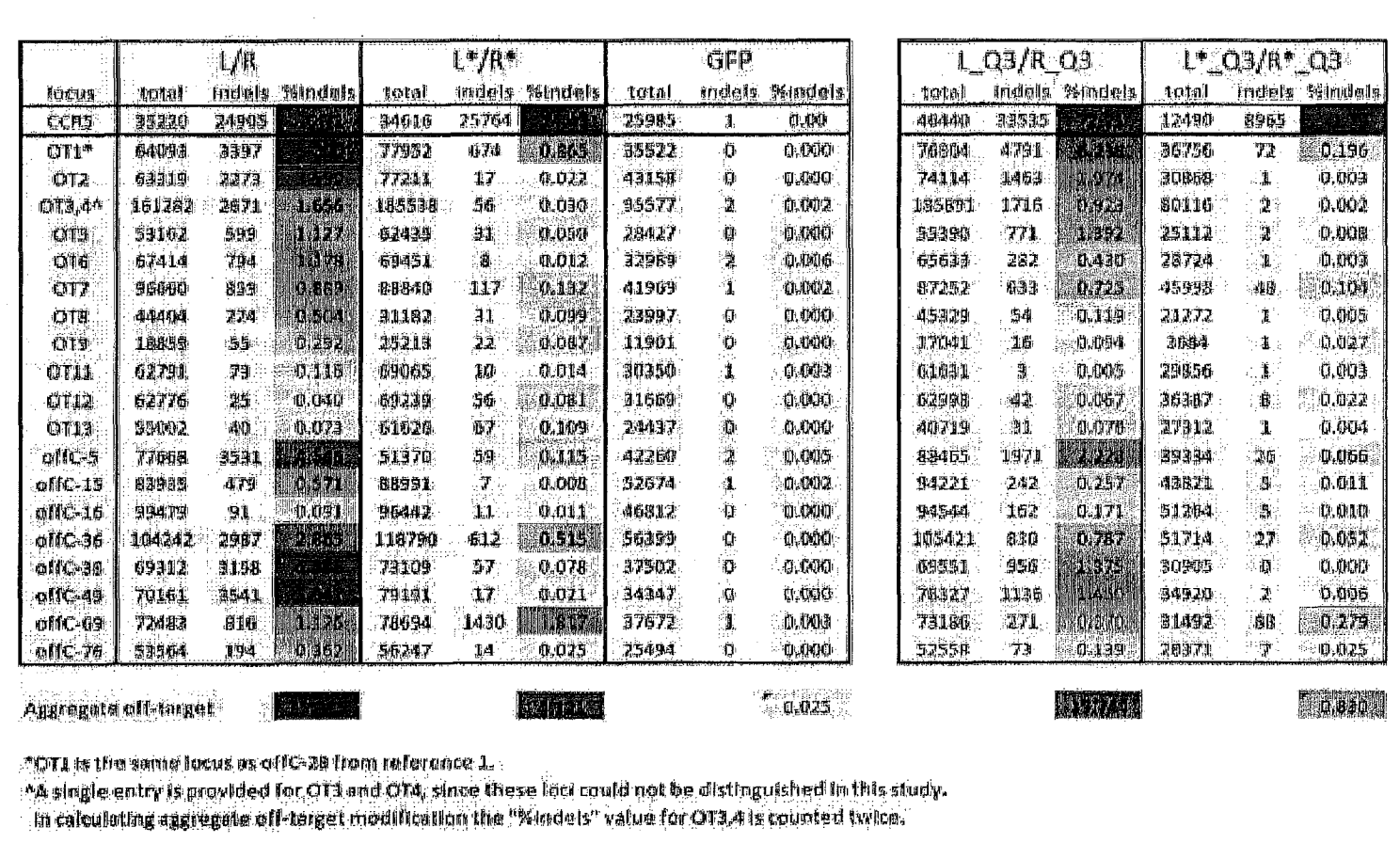

As shown in FIG. 9, the Q3 mutations (L_Q3/R_Q3) did lower aggregate off-target activity from 35.6% to 19.7%, but the Q3 mutations did not outperform the 4.1% aggregate off-target activity observed with the non-canonical RVD variants L* and R*. However, a combination of the Q3 mutations and the non-canonical RVD variants (L*_Q3/R*_Q3) did yield additional improvements in aggregate off-target activity relative to either the Q3 mutations or non-canonical RVD variants alone.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed:

1. An isolated cell comprising a target site and a non-naturally occurring TALE DNA-binding protein that binds to the target site, the TALE DNA-binding protein comprising a plurality of TALE-repeat units, each TALE-repeat unit comprising a repeat variable di-residue region (RVD), and wherein
   (i) the RVD in the first repeat recognizes adenine (A) at the 5' end of the target site;
   (ii) the target site does not comprise a 3' adenine (A);
   (iii) the target site comprises 2 or fewer consecutive thymines (Ts); and
   (iv) the target site does not contain GG or GC dinucleotides.

2. The cell of claim 1, comprising a fusion protein comprising the TALE DNA-binding protein and a functional domain.

3. The cell of claim 2, wherein the functional domain is selected from the group consisting of a transcriptional activator, a transcriptional repressor, methyltransferase and a nuclease cleavage domain.

4. The cell of claim 1, wherein the TALE DNA-binding domain is introduced into the cell as a polynucleotide.

5. The cell of claim 3, wherein the fusion protein is introduced into the cell as a polynucleotide.

6. The cell of claim 1, wherein the cell is a eukaryotic cell.

7. The cell of claim 6, wherein the cell is a fungal cell.

8. The cell of claim 6, wherein the cell is a mammalian or plant cell.

9. The cell of claim 8, wherein the mammalian cell is a stem cell.

10. The cell of claim 3, wherein the nuclease cleavage domain comprises a FokI cleavage domain.

11. A method of making a cell according to claim 1, the method comprising:
    providing a cell;
    contacting the cell with a first TALE DNA-binding protein comprising a plurality of TALE-repeat units, each TALE-repeat unit comprising a repeat variable di-residue region (RVD) that binds to a first target DNA wherein the first TALE DNA binding protein and the first target sequence comprise the following features:

(i) the RVD in the first repeat recognizes adenine (A); and
(ii) the target site does not comprise a 3' adenine (A); and
(iii) the target site comprises 2 or fewer consecutive thymines (Ts); and
(iv) the target site does not contain GG or GC dinucleotides, wherein said first TALE DNA binding protein exhibits enhanced specificity or activity for the first target DNA as compared to a second TALE DNA binding protein that binds to a second target DNA wherein the second TALE DNA binding protein and the second target DNA do not comprise features (i) to (iv).

12. A method of modulating expression of an endogenous gene in a cell, the method comprising:
providing a cell according to claim 3, wherein the target site is in the endogenous gene and further wherein expression of the endogenous gene is modulated.

13. The method of claim 12, wherein the modulation is selected from the group consisting of gene activation, gene repression and gene inactivation.

14. The method of claim 13, wherein the fusion protein comprises a cleavage domain or cleavage half-domain and the endogenous gene is inactivated by cleavage.

15. The method of claim 12, wherein the fusion protein is introduced as a polynucleotide encoding the fusion protein.

16. A method of modifying a region of interest in the genome of a cell, the method comprising:
providing a cell according to claim 10, wherein the TALE DNA-binding protein binds to a target site in the genome of the cell and the fusion protein cleaves the genome in the region of interest.

17. The method of claim 16, wherein the modifying comprises introducing a deletion in the region of interest.

18. The method of claim 16, wherein the modifying comprises introducing an exogenous nucleic acid into the region of interest, the method further comprising introducing the exogenous nucleic acid into the cell, wherein the exogenous nucleic acid is integrated into the region of interest.

19. The method of claim 16, wherein the cell is a eukaryotic cell selected from the selected from the group consisting of a plant cell, an animal cell, a fish cell and a yeast cell.

20. The method of claim 16, wherein the fusion protein is introduced as a polynucleotide encoding the fusion protein.

21. A kit comprising a cell according to claim 1.

* * * * *

SEQUENCE LISTING

```
<160> NUMBER OF SEQ ID NOS: 63

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t or g

<400> SEQUENCE: 2
ttgacnatcc t                                                          11

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttcattacac ctgcagct                                                   18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcttccagaa ttgatact                                                   18

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 5
cttcattaca cctgcagctc tcatttt                                              27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tacagtcagt atcaattctg gaagaat                                              27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttttattaca cttccagatc ttttatt                                              27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gttaccagat atcctttctg gaagaaa                                              27

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cttgattcca cctgtagctc cgagcaaa                                             28

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cccgatgaag ccccaggtgt tttaaat                                              27

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (1)..(13)
<223> OTHER INFORMATION: Any amino acid
<220> FEATURE:
<221> NAME/KEY: MISC_FEATURE
<222> LOCATION: (12)..(13)
<223> OTHER INFORMATION: Repeat variable di-residue region
<220> FEATURE:
<221> NAME/KEY: MISC_FEATURE
<222> LOCATION: (14)..(35)
<223> OTHER INFORMATION: Any amino acid and this region may encompass
      20-22 residues
<220> FEATURE:
<223> OTHER INFORMATION: See specification as filed for detailed
      description of substitutions and preferred embodiments

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(13)
<223> OTHER INFORMATION: Any amino acid
<220> FEATURE:
<221> NAME/KEY: MISC_FEATURE
<222> LOCATION: (12)..(13)
<223> OTHER INFORMATION: Repeat variable di-residue region
<220> FEATURE:
<221> NAME/KEY: MISC_FEATURE
<222> LOCATION: (14)..(35)
<223> OTHER INFORMATION: Any amino acid and this region may encompass
      20-22 residues
<220> FEATURE:
<223> OTHER INFORMATION: See specification as filed for detailed
      description of substitutions and preferred embodiments

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 13
aatcgcgtcg nnnnnngggg gaaag                                       25
```

```
<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(19)
<223> OTHER INFORMATION: a, c, t, g, unknown or other

<400> SEQUENCE: 14
cttgctttcc cccnnnnnnc gacgc                                              25

<210> SEQ ID NO 15
<211> LENGTH: 765
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (324)..(325)
<223> OTHER INFORMATION: Any amino acid

<400> SEQUENCE: 15

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Gly Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Asn Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
```

```
                245                 250                 255
Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
            275                 280                 285

Ser His Asp Gly Gly Lys Gln Ala Leu Glu Thr Val Gln Arg Leu Leu
            290                 295                 300

Pro Val Leu Cys Gln Asp His Gly Leu Thr Pro Asp Gln Val Val Ala
305                 310                 315                 320

Ile Ala Ser Xaa Xaa Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Ile Gly Gly Lys Gln Ala Leu Glu Thr Val
            355                 360                 365

Gln Arg Leu Leu Pro Val Leu Cys Gln Asp His Gly Leu Thr Pro Glu
            370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
            435                 440                 445

Leu Thr Pro Ala Gln Val Val Ala Ile Ala Ser His Asp Gly Gly Lys
            450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Asn Gly Gly
                485                 490                 495

Gly Arg Pro Ala Leu Glu Ser Ile Val Ala Gln Leu Ser Arg Pro Asp
            500                 505                 510

Pro Ala Leu Ala Ala Leu Thr Asn Asp His Leu Val Ala Leu Ala Cys
            515                 520                 525

Leu Gly Gly Arg Pro Ala Leu Asp Ala Val Lys Lys Gly Leu Pro His
            530                 535                 540

Ala Pro Ala Leu Ile Lys Arg Thr Asn Arg Arg Ile Pro Glu Arg Thr
545                 550                 555                 560

Ser His Arg Val Ala Gly Ser Gln Leu Val Lys Ser Glu Leu Glu Glu
                565                 570                 575

Lys Lys Ser Glu Leu Arg His Lys Leu Lys Tyr Val Pro His Glu Tyr
            580                 585                 590

Ile Glu Leu Ile Glu Ile Ala Arg Asn Ser Thr Gln Asp Arg Ile Leu
            595                 600                 605

Glu Met Lys Val Met Glu Phe Phe Met Lys Val Tyr Gly Tyr Arg Gly
            610                 615                 620

Lys His Leu Gly Gly Ser Arg Lys Pro Asp Gly Ala Ile Tyr Thr Val
625                 630                 635                 640

Gly Ser Pro Ile Asp Tyr Gly Val Ile Val Asp Thr Lys Ala Tyr Ser
                645                 650                 655

Gly Gly Tyr Asn Leu Pro Ile Gly Gln Ala Asp Glu Met Gln Arg Tyr
            660                 665                 670
```

```
Val Glu Glu Asn Gln Thr Arg Asn Lys His Ile Asn Pro Asn Glu Trp
        675                 680                 685

Trp Lys Val Tyr Pro Ser Ser Val Thr Glu Phe Lys Phe Leu Phe Val
        690                 695                 700

Ser Gly His Phe Lys Gly Asn Tyr Lys Ala Gln Leu Thr Arg Leu Asn
705                 710                 715                 720

His Ile Thr Asn Cys Asn Gly Ala Val Leu Ser Val Glu Glu Leu Leu
                725                 730                 735

Ile Gly Gly Glu Met Ile Lys Ala Gly Thr Leu Thr Leu Glu Glu Val
            740                 745                 750

Arg Arg Lys Phe Asn Asn Gly Glu Ile Asn Phe Arg Ser
            755                 760                 765

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggcctgcgt cgacgaattc g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacagcctga gctctctaga g                                              21

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggatccggat ggtctcaacc tgacccaga ccag                                 34

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagggatgcg ggtctctgag tccatgatcc tggcacagt                           39

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 20
ggatccggat gggtctcaac tcaccccaga ccaggta                             37

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gagggatgcg ggtctctcag cccatgatcc tggcacagt                           39

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggatccggat gggtctcagc tgaccccaga ccag                                34

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagggatgcg ggtctctcaa accatgatcc tggcacagt                           39

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggatccggat gggtctcatt tgaccccaga ccaggta                             37

<210> SEQ ID NO 25
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctcgagggat ggtctccgtc ctccgccgtg gctagcaatg gcgaccacct gttcgggtgt    60
caggccatga tcc                                                       73

<210> SEQ ID NO 26
<211> LENGTH: 73
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 26
ctcgagggat ggtctccgtc ctccgccctt gctagcaatg gcgaccacct gttcgggtgt    60
caggccatga tcc                                                        73

<210> SEQ ID NO 27
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctcgagggat ggtctccgtc ctcccccgtt gctagcaatg gcgaccacct gttcgggtgt    60
caggccatga tcc                                                        73

<210> SEQ ID NO 28
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctcgagggat ggtctccgtc ctccgccgtg gctagcaatg gcgaccacct gttcgggtgt    60
caggccatga tcc                                                        73

<210> SEQ ID NO 29
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcgagggat ggtctccgtc ctccgcccTt gctagcaatg gcgaccacct gttcgggtgt    60
caggccatga tcc                                                        73

<210> SEQ ID NO 30
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcgagggat ggtctccgtc ctccgccctg gctagcaatg gcgaccacct gttcgggtgt    60
caggccatga tcc                                                        73

<210> SEQ ID NO 31
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctcgagggat ggtctccgtc ctccgccgct gctagcaatg gcgaccacct gttcgggtgt    60
caggccatga tcc    73

<210> SEQ ID NO 32
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctcgagggat ggtctccgtc ctccgcccct gctagcaatg gcgaccacct gttcgggtgt    60
caggccatga tcc    73

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(46)
<223> OTHER INFORMATION: a, c, t or g

<400> SEQUENCE: 33
cagggatcca tgcactgtac gcccnnnnnn nnnnnnnnnn nnnnnnggggc cacttgactg    60 cggatcctgg    70

<210> SEQ ID NO 34
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcttactggc ttatcgaaat taatacgact cactataggg agacgaattc accaccatgg    60
tggatctacg cacgctcg    78

<210> SEQ ID NO 35
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cacgtacttc agcttttatt aggcgtagtc gggcacgtcg taggggtagc ccgcgactcg    60
atgggaagtt c    71

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagggatcca tgcactgtac g                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagggatcca tgcactgtac g                                              21

<210> SEQ ID NO 38
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
catagtcccc ttgacaatcc tcctcggtgt agttttcaca gtcagtccac acgtc         55

<210> SEQ ID NO 39
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
catagtcccc ttgaccatcc tcctcggtgt agttttcaca gtcagtccac acgtc         55

<210> SEQ ID NO 40
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
catagtcccc ttgacgatcc tcctcggtgt agttttcaca gtcagtccac acgtc         55

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
catagtcccc ttgactatcc tcctcggtgt agttttcaca gtcagtccac acgtc         55

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Biotin

<400> SEQUENCE: 42

```
gacgtgtgga ctgactgtga                                               20
```

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
gcagagctct ctggctaact agag                                          24
```

<210> SEQ ID NO 44
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
gcgtaaagct taggcgtagt cgggcacgtc gtaggggtag ccgggcacca gctgggatcc    60
ccgcaggtg                                                           69
```

<210> SEQ ID NO 45
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
catagtcccc ttcatatcct cctcggtgta gttttcacag tcagtccaca cgtc          54
```

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
catagtcccc tcttcatcct cctcggtgta gttttcacag tcagtccaca cgtc          54
```

<210> SEQ ID NO 47
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
catagtcccc ttgactacat cctcggtgta gttttcacag tcagtccaca cgtc          54
```

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 48
catagtcccc ttgaccctgt cctcggtgta gttttcacag tcagtccaca cgtc         54

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
catagtcccc ttgaccagct cctcggtgta gttttcacag tcagtccaca cgtc         54

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
catagtcccc ttgaccagat cctcggtgta gttttcacag tcagtccaca cgtc         54

<210> SEQ ID NO 51
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
catagtcccc ttgacattgt cctcggtgta gttttcacag tcagtccaca cgtc         54

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
catagtcccc ttgacatact cctcggtgta gttttcacag tcagtccaca cgtc         54

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acacgacgct cttccgatct                                               20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
```
gacgtgtgct cttccgat                                                        18

<210> SEQ ID NO 55
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (323)..(324)
<223> OTHER INFORMATION: Any amino acid
<220> FEATURE:
<221> NAME/KEY: MOD_RES
<222> LOCATION: (357)..(358)
<223> OTHER INFORMATION: Any amino acid
<220> FEATURE:
<221> NAME/KEY: MOD_RES
<222> LOCATION: (391)..(392)
<223> OTHER INFORMATION: Any amino acid
<220> FEATURE:
<221> NAME/KEY: MOD_RES
<222> LOCATION: (425)..(426)
<223> OTHER INFORMATION: Any amino acid

<400> SEQUENCE: 55

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Met Val Asp Leu Arg Thr Leu Gly Tyr Ser
            35                  40                  45

Gln Gln Gln Gln Glu Lys Ile Lys Pro Lys Val Arg Ser Thr Val Ala
        50                  55                  60

Gln His His Glu Ala Leu Val Gly His Gly Phe Thr His Ala His Ile
65                  70                  75                  80

Val Ala Leu Ser Gln His Pro Ala Ala Leu Gly Thr Val Ala Val Lys
                85                  90                  95

Tyr Gln Asp Met Ile Ala Ala Leu Pro Glu Ala Thr His Glu Ala Ile
            100                 105                 110

Val Gly Val Gly Lys Gln Trp Ser Gly Ala Arg Ala Leu Glu Ala Leu
        115                 120                 125

Leu Thr Val Ala Gly Glu Leu Arg Gly Pro Pro Leu Gln Leu Asp Thr
130                 135                 140

Gly Gln Leu Leu Lys Ile Ala Lys Arg Gly Gly Val Thr Ala Val Glu
145                 150                 155                 160

Ala Val His Ala Trp Arg Asn Ala Leu Thr Gly Ala Pro Leu Asn Leu
                165                 170                 175

Thr Pro Asp Gln Val Val Ala Ile Ala Ser Asn Gly Gly Lys Gln
            180                 185                 190

Ala Leu Glu Thr Val Gln Arg Leu Leu Pro Val Leu Cys Gln Asp His
        195                 200                 205

Gly Leu Thr Pro Asp Gln Val Val Ala Ile Ala Asn Asn Asn Gly Gly
    210                 215                 220

Lys Gln Ala Leu Glu Thr Val Gln Arg Leu Leu Pro Val Leu Cys Gln
225                 230                 235                 240

Ala His Gly Leu Thr Pro Asp Gln Val Val Ala Ile Ala Ser Asn Ile
                245                 250                 255

Gly Gly Lys Gln Ala Leu Glu Thr Val Gln Arg Leu Leu Pro Val Leu

```
              260                 265                 270
Cys Gln Ala His Gly Leu Thr Pro Ala Gln Val Val Ala Ile Ala Ser
            275                 280                 285

His Asp Gly Gly Lys Gln Ala Leu Glu Thr Val Gln Arg Leu Leu Pro
        290                 295                 300

Val Leu Cys Gln Asp His Gly Leu Thr Pro Asp Gln Val Val Ala Ile
305                 310                 315                 320

Ala Ser Xaa Xaa Gly Gly Lys Gln Ala Leu Glu Thr Val Gln Arg Leu
                325                 330                 335

Leu Pro Val Leu Cys Gln Asp His Gly Leu Thr Pro Glu Gln Val Val
            340                 345                 350

Ala Ile Ala Ser Xaa Xaa Gly Gly Lys Gln Ala Leu Glu Thr Val Gln
        355                 360                 365

Arg Leu Leu Pro Val Leu Cys Gln Ala His Gly Leu Thr Pro Asp Gln
    370                 375                 380

Val Val Ala Ile Ala Ser Xaa Xaa Gly Gly Lys Gln Ala Leu Glu Thr
385                 390                 395                 400

Val Gln Arg Leu Leu Pro Val Leu Cys Gln Ala His Gly Leu Thr Pro
                405                 410                 415

Ala Gln Val Val Ala Ile Ala Ser Xaa Xaa Gly Gly Lys Gln Ala Leu
            420                 425                 430

Glu Thr Val Gln Arg Leu Leu Pro Val Leu Cys Gln Asp His Gly Leu
        435                 440                 445

Thr Pro Glu Gln Val Val Ala Ile Ala Ser Asn Gly Gly Arg Pro
    450                 455                 460

Ala Leu Glu Ser Ile Val Ala Gln Leu Ser Arg Pro Asp Pro Ala Leu
465                 470                 475                 480

Ala Ala Leu Thr Asn Asp His Leu Val Ala Leu Ala Cys Leu Gly Gly
                485                 490                 495

Arg Pro Ala Leu Asp Ala Val Lys Lys Gly Leu Pro His Ala Pro Ala
            500                 505                 510

Leu Ile Lys Arg Thr Asn Arg Arg Ile Pro Glu Arg Thr Ser His Arg
        515                 520                 525

Val Ala Gly Ser Gly Tyr Pro Tyr Asp Val Pro Asp Tyr Ala
    530                 535                 540

<210> SEQ ID NO 56
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (188)..(189)
<223> OTHER INFORMATION: Any amino acid
<220> FEATURE:
<221> NAME/KEY: MOD_RES
<222> LOCATION: (222)..(223)
<223> OTHER INFORMATION: Any amino acid
<220> FEATURE:
<221> NAME/KEY: MOD_RES
<222> LOCATION: (256)..(257)
<223> OTHER INFORMATION: Any amino acid
<220> FEATURE:
<221> NAME/KEY: MOD_RES
<222> LOCATION: (290)..(291)
<223> OTHER INFORMATION: Any amino acid
<220> FEATURE:
<221> NAME/KEY: MOD_RES
```

```
<222> LOCATION: (324)..(325)
<223> OTHER INFORMATION: Any amino acid
<220> FEATURE:
<221> NAME/KEY: MOD_RES
<222> LOCATION: (358)..(359)
<223> OTHER INFORMATION: Any amino acid
<220> FEATURE:
<221> NAME/KEY: MOD_RES
<222> LOCATION: (392)..(393)
<223> OTHER INFORMATION: Any amino acid
<220> FEATURE:
<221> NAME/KEY: MOD_RES
<222> LOCATION: (426)..(427)
<223> OTHER INFORMATION: Any amino acid
<220> FEATURE:
<221> NAME/KEY: MOD_RES
<222> LOCATION: (460)..(461)
<223> OTHER INFORMATION: Any amino acid
<220> FEATURE:
<221> NAME/KEY: MOD_RES
<222> LOCATION: (494)..(495)
<223> OTHER INFORMATION: Any amino acid
<220> FEATURE:
<221> NAME/KEY: MOD_RES
<222> LOCATION: (528)..(529)
<223> OTHER INFORMATION: Any amino acid
<220> FEATURE:
<221> NAME/KEY: MOD_RES
<222> LOCATION: (561)..(562)
<223> OTHER INFORMATION: Any amino acid
<220> FEATURE:
<221> NAME/KEY: MOD_RES
<222> LOCATION: (596)..(597)
<223> OTHER INFORMATION: Any amino acid
<220> FEATURE:
<221> NAME/KEY: MOD_RES
<222> LOCATION: (630)..(631)
<223> OTHER INFORMATION: Any amino acid
<220> FEATURE:
<221> NAME/KEY: MOD_RES
<222> LOCATION: (663)..(664)
<223> OTHER INFORMATION: Any amino acid
<220> FEATURE:
<221> NAME/KEY: MOD_RES
<222> LOCATION: (698)..(699)
<223> OTHER INFORMATION: Any amino acid
<220> FEATURE:
<221> NAME/KEY: MOD_RES
<222> LOCATION: (732)..(733)
<223> OTHER INFORMATION: Any amino acid

<400> SEQUENCE: 56

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140
```

```
Thr Gly Gln Leu Leu Lys Ile Ala Lys Arg Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Xaa Xaa Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Ser Xaa Xaa Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Xaa
                245                 250                 255

Xaa Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Ser Xaa Xaa Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Xaa Xaa Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser Xaa Xaa Gly Gly Lys Gln Ala Leu Glu Thr Val
        355                 360                 365

Gln Arg Leu Leu Pro Val Leu Cys Gln Ala His Gly Leu Thr Pro Asp
    370                 375                 380

Gln Val Val Ala Ile Ala Ser Xaa Xaa Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser Xaa Xaa Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Xaa Xaa Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Xaa Xaa Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Xaa
        515                 520                 525

Xaa Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560
```

```
Xaa Xaa Asn Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
        580                 585                 590

Ile Ala Ser Xaa Xaa Gly Gly Lys Gln Ala Leu Glu Thr Val Gln Arg
    595                 600                 605

Leu Leu Pro Val Leu Cys Gln Asp His Gly Leu Thr Pro Glu Gln Val
610                 615                 620

Val Ala Ile Ala Ser Xaa Xaa Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Xaa Xaa Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Ala Gln Val Val Ala Ile Ala Ser Xaa Xaa Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser Xaa Xaa Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
        755                 760                 765

Gly Arg Pro Ala Leu Asp Ala Val Lys Lys Gly Leu Pro His Ala Pro
    770                 775                 780

Ala Leu Ile Lys Arg Thr Asn Arg Arg Ile Pro Glu Arg Thr Ser His
785                 790                 795                 800

Arg Val Ala Gly Ser Gln Leu Val Lys Ser Glu Leu Glu Glu Lys Lys
                805                 810                 815

Ser Glu Leu Arg His Lys Leu Lys Tyr Val Pro His Glu Tyr Ile Glu
            820                 825                 830

Leu Ile Glu Ile Ala Arg Asn Ser Thr Gln Asp Arg Ile Leu Glu Met
        835                 840                 845

Lys Val Met Glu Phe Phe Met Lys Val Tyr Gly Tyr Arg Gly Lys His
    850                 855                 860

Leu Gly Gly Ser Arg Lys Pro Asp Gly Ala Ile Tyr Thr Val Gly Ser
865                 870                 875                 880

Pro Ile Asp Tyr Gly Val Ile Val Asp Thr Lys Ala Tyr Ser Gly Gly
                885                 890                 895

Tyr Asn Leu Pro Ile Gly Gln Ala Asp Glu Met Gln Arg Tyr Val Glu
            900                 905                 910

Glu Asn Gln Thr Arg Asn Lys His Ile Asn Pro Asn Glu Trp Trp Lys
        915                 920                 925

Val Tyr Pro Ser Ser Val Thr Glu Phe Lys Phe Leu Phe Val Ser Gly
    930                 935                 940

His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
                965                 970                 975

Gly Glu Met Ile Lys Ala Gly Thr Leu Thr Leu Glu Glu Val Arg Arg
```

```
                     980                 985                 990
Lys Phe Asn Asn Gly Glu Ile Asn  Phe Arg Ser
        995                1000

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccaggatccg cagtcaagtg g                                                   21

<210> SEQ ID NO 58
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (187)..(188)
<223> OTHER INFORMATION: Any amino acid
<220> FEATURE:
<221> NAME/KEY: MOD_RES
<222> LOCATION: (221)..(222)
<223> OTHER INFORMATION: Any amino acid
<220> FEATURE:
<221> NAME/KEY: MOD_RES
<222> LOCATION: (255)..(256)
<223> OTHER INFORMATION: Any amino acid
<220> FEATURE:
<221> NAME/KEY: MOD_RES
<222> LOCATION: (289)..(290)
<223> OTHER INFORMATION: Any amino acid

<400> SEQUENCE: 58

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Met Val Asp Leu Arg Thr Leu Gly Tyr Ser
        35                  40                  45

Gln Gln Gln Gln Glu Lys Ile Lys Pro Lys Val Arg Ser Thr Val Ala
    50                  55                  60

Gln His His Glu Ala Leu Val Gly His Gly Phe Thr His Ala His Ile
65                  70                  75                  80

Val Ala Leu Ser Gln His Pro Ala Ala Leu Gly Thr Val Ala Val Lys
                85                  90                  95

Tyr Gln Asp Met Ile Ala Ala Leu Pro Glu Ala Thr His Glu Ala Ile
            100                 105                 110

Val Gly Val Gly Lys Gln Trp Ser Gly Ala Arg Ala Leu Glu Ala Leu
        115                 120                 125

Leu Thr Val Ala Gly Glu Leu Arg Gly Pro Pro Leu Gln Leu Asp Thr
    130                 135                 140

Gly Gln Leu Leu Lys Ile Ala Lys Arg Gly Gly Val Thr Ala Val Glu
145                 150                 155                 160

Ala Val His Ala Trp Arg Asn Ala Leu Thr Gly Ala Pro Leu Asn Leu
                165                 170                 175

Thr Pro Asp Gln Val Val Ala Ile Ala Ser Xaa Xaa Gly Gly Lys Gln
```

180                 185                 190
Ala Leu Glu Thr Val Gln Arg Leu Leu Pro Val Leu Cys Gln Asp His
            195                 200                 205
Gly Leu Thr Pro Glu Gln Val Val Ala Ile Ala Ser Xaa Xaa Gly Gly
        210                 215                 220
Lys Gln Ala Leu Glu Thr Val Gln Arg Leu Leu Pro Val Leu Cys Gln
225                 230                 235                 240
Ala His Gly Leu Thr Pro Asp Gln Val Val Ala Ile Ala Ser Xaa Xaa
                245                 250                 255
Gly Gly Lys Gln Ala Leu Glu Thr Val Gln Arg Leu Leu Pro Val Leu
            260                 265                 270
Cys Gln Ala His Gly Leu Thr Pro Ala Gln Val Val Ala Ile Ala Ser
            275                 280                 285
Xaa Xaa Gly Gly Lys Gln Ala Leu Glu Thr Val Gln Arg Leu Leu Pro
        290                 295                 300
Val Leu Cys Gln Asp His Gly Leu Thr Pro Asp Gln Val Val Ala Ile
305                 310                 315                 320
Ala Ser Asn Ile Gly Gly Lys Gln Ala Leu Glu Thr Val Gln Arg Leu
                325                 330                 335
Leu Pro Val Leu Cys Gln Asp His Gly Leu Thr Pro Glu Gln Val Val
            340                 345                 350
Ala Ile Ala Ser Asn Gly Gly Lys Gln Ala Leu Glu Thr Val Gln
            355                 360                 365
Arg Leu Leu Pro Val Leu Cys Gln Ala His Gly Leu Thr Pro Asp Gln
        370                 375                 380
Val Val Ala Ile Ala Ser His Asp Gly Gly Lys Gln Ala Leu Glu Thr
385                 390                 395                 400
Val Gln Arg Leu Leu Pro Val Leu Cys Gln Ala His Gly Leu Thr Pro
                405                 410                 415
Ala Gln Val Val Ala Ile Ala Ser His Asp Gly Gly Lys Gln Ala Leu
            420                 425                 430
Glu Thr Val Gln Arg Leu Leu Pro Val Leu Cys Gln Asp His Gly Leu
            435                 440                 445
Thr Pro Glu Gln Val Val Ala Ile Ala Ser Asn Gly Gly Gly Arg Pro
        450                 455                 460
Ala Leu Glu Ser Ile Val Ala Gln Leu Ser Arg Pro Asp Pro Ala Leu
465                 470                 475                 480
Ala Ala Leu Thr Asn Asp His Leu Val Ala Leu Ala Cys Leu Gly Gly
                485                 490                 495
Arg Pro Ala Leu Asp Ala Val Lys Lys Gly Leu Pro His Ala Pro Ala
            500                 505                 510
Leu Ile Lys Arg Thr Asn Arg Arg Ile Pro Glu Arg Thr Ser His Arg
            515                 520                 525
Val Ala Gly Ser Gly Tyr Pro Tyr Asp Val Pro Asp Tyr Ala
        530                 535                 540

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
tcattacacc tgcagct                                                    17

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cttcattaca cctgcagctc tca                                             23

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccatacagtc agtatcaat                                                  19

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tttagataca cctacctata aat                                             23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tttaccctgc aggtgtgatg aat                                             23
```